US009410208B2

(12) United States Patent
Tanaka et al.

(10) Patent No.: US 9,410,208 B2
(45) **Date of Patent: *Aug. 9, 2016**

(54) MARKER AND REAGENT FOR DETECTION OF HUMAN IL-17-PRODUCING HELPER T CELLS, AND METHOD FOR DETECTION OF HUMAN IL-17-PRODUCING HELPER T CELLS

(71) Applicant: SYSMEX CORPORATION, Kobe-shi, Hyogo (JP)

(72) Inventors: Satoshi Tanaka, Kobe (JP); Hitoshi Uga, Kobe (JP); Masafumi Ikeda, Kobe (JP); Yoshiaki Miyamoto, Kobe (JP); Masatoshi Yanagida, Kobe (JP); Masakazu Kadowaki, Kobe (JP); Takahiro Okazawa, Kobe (JP); Hirokazu Kurata, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/868,638

(22) Filed: Apr. 23, 2013

(65) Prior Publication Data

US 2013/0267435 A1 Oct. 10, 2013

Related U.S. Application Data

(60) Division of application No. 13/360,324, filed on Jan. 27, 2012, now abandoned, which is a continuation of application No. PCT/JP2010/062807, filed on Jul. 29, 2010.

(30) Foreign Application Priority Data

Jul. 29, 2009 (JP) ................................ 2009-176755

(51) Int. Cl.

| | |
|---|---|
| ***G01N 33/537*** | (2006.01) |
| ***C12Q 1/68*** | (2006.01) |
| ***C07K 14/54*** | (2006.01) |
| ***G01N 33/50*** | (2006.01) |
| ***G01N 33/68*** | (2006.01) |

(52) U.S. Cl.

CPC .............. *C12Q 1/6888* (2013.01); *C07K 14/54* (2013.01); *C12Q 1/6881* (2013.01); *G01N 33/505* (2013.01); *G01N 33/68* (2013.01); *C12Q 2600/158* (2013.01); *G01N 2333/54* (2013.01)

(58) Field of Classification Search

None

See application file for complete search history.

(56) References Cited

FOREIGN PATENT DOCUMENTS

| | | | |
|---|---|---|---|
| JP | 2000-186046 | A | 7/2000 |
| JP | 2007-506100 | A | 3/2007 |
| WO | 2005/029091 | A2 | 3/2005 |
| WO | 2008104608 | A1 | 9/2008 |
| WO | 2009002515 | A1 | 12/2008 |
| WO | 2009092087 | A2 | 7/2009 |
| WO | 2009/107785 | A1 | 9/2009 |
| WO | 2010/024289 | A1 | 3/2010 |

OTHER PUBLICATIONS

Harrington et al., Nature Immunology, 2005, vol. 6, pp. 1123-1132.*

Ormerod, Cell Separation a Practical Approach, 1998, pp. 169-189.*

Sui et al., American Jounral of PAthology, 2005, vol. 166, pp. 1247-1258.*

Korn et al., Annu. Rev. Immunol., 2009, vol. 27, pp. 485-517.*

Aricescu et al., The EMBO Journal, 2006, vol. 25, pp. 701-712.*

Bianchi et al., Experimental Cell Research, 1999, vol. 248, pp. 329-338.*

Mochizuki et al., Cancer Science, 2007, vol. 98, pp. 621-628.*

Engemaier et al., Genomics, 2006, vol. 87, pp. 254-264.*

Miyahara et al., Journal of Surgical Oncology, 2001, vol. 77, pp. 49-54.*

Kristiansen et al., Analytical Cellular Pathology, 203, vol. 25, pp. 77-81.*

Miyagawa et al., Immunology, 2009, vol. 128, pp. 405-419.*

Marchese et al., GEnomics, 1999, vol. 56, pp. 12-21.*

Maddaluno et al., JEM, 2009, vol. 206 pp. 623-635.*

Appay et al., Journal of Immunology, 2007; 179:7406-7414.*

Affimetrix GeneChip Human Genome U133 Arrays Data Sheet, 2003-2007, downloaded from http://media.affymetrix.com/support/technical/datasheets/hgu133arrays_datasheet.pdf on Oct. 5, 2012.

Affimetrix GeneChip Human Genome U133 Plus 2.0 Array Probe Sheet, FASTA format, Aug. 20, 2008, downloaded from http://www.affymetrix.com/Auth/analysis/downloads/data/HG-U133_Plus_2.probe_fasta.zip on Oct. 5, 2012, Only pp. 7813-7814.

Affimetrix GeneChip Human Genome U133 Plus 2.0 Array Target Sheet, FASTA format, Aug. 20, 2008, downloaded from http://www.affymetrix.com/Auth/analysis/downloads/data/HG-U133_Plus_2.targetzip on Oct. 5, 2012. Only p. 2953.

Eva V. Acosta-Rodriguez et al., "Surface phenotype and antigenic specificity of human interleukin 17-Producing T helper memory cells", *Nature Immunology*, 2007, 8(6): 639-646.

(Continued)

*Primary Examiner* — Anne Gussow
*Assistant Examiner* — Mindy G Brown
(74) *Attorney, Agent, or Firm* — Sughrue Mion, PLLC

(57) ABSTRACT

The present invention relates to a marker allowing specific detection of human IL-17-producing helper T-cells (human Th17 cells), a method for specifically detecting human Th17 cells and a reagent for detecting human Th17 cells.

6 Claims, 3 Drawing Sheets

(56) References Cited

OTHER PUBLICATIONS

Francesco Annunziato et al., "Phenotypic and functional features of human Th17 cells", *The Journal of Experimental Medicine*, 2007, 204(8): 1849-1861.
S. Homs et al., "Predominant TH1 and Cytotoxic Phenotype in Biopsies from Renal Transplant Recipients with Transplant Glomerulopathy", *American Journal of Transplantation*, 2009, 9: 1230-1236.
Ivaylo I. Ivanov et al., "The Orphan Nuclear Receptor RORγT Directs the Differentiation Program of Proinflammatory IL-17$^+$ T Helper Cells", *Cell*, 2006, 126: 1121-1133.
Weihong Liu et al., CD127 expression inversely correlates with foxP3 and suppressive function of human CD4$^+$ T reg cells, *Journal of Experimental Medicine*, 2006, 203(7): 1701-1711.
Jason S. Stumhofer et al., "Interleukin 27 negatively regulates the development of interleukin 17-producing T helper cells during chronic inflammation of the central nervous system", *Nature Immunology*, 2006, 7(9): 937-945.
Nicholas J. Wilson et al., "Development, cytokine profile and function of human interleukin 17-producing helper T cells", *Nature Immunology*, 2007, 7: 1-8.
Lorenzo Cosmi et al., "Human interleukin 17-producing cells originate from a CD161+CD4+ T cell precursor", The Journal of Experimental Medicine, Jul. 28, 2008, pp. 1903-1918, vol. 205, No. 8.
Hendrik Streeck et al., "Rapid ex vivo isolation and long-term culture of human Th17 cells", Journal of Immunological Methods, 2008, pp. 115-125, vol. 333.
Weizmann Institute, "Query results for probes for PTPRM gene", retrieved from URL/http://genecards.weizmann.ac.il.cgi-bin/geneannot/GA_search.pl on Jan. 18, 2013.
Gebbink et al., "Cloning, Expression and chromosomal localization of a new putative receptor-like protein tyrosine phosphatase", Febs Letters, 1991: 290(1 & 2):123-130.
Wagner et al., "Physical Mapping of Receptor Type Protein Tyrosine Phosphatase Sigma (PTPRS) to Human Chromosome 19p13.3", Genomics, 1996, 38:76-78.
Aricescu et al., "Structure of a Tyrosine Phosphatase Adhesive Interaction Reveals a Spacer-Clamp Mechanism", Science, 2007, 317:1217-1220.
Aricescu et al., "*Homo sapiens* protein tyrosine phosphatase, receptor type, M (PTPRM), transcript variant 1, mRNA", GenBank Accession No. NM_001105244, The National Center for Biotechnology, Sep. 21, 2007, retrieved from http://www.ncbi.nlm.nih.gov/nuccore/NM_001105244 on Jul. 4, 2013, pp. 1-9.

* cited by examiner

MARKER AND REAGENT FOR DETECTION OF HUMAN IL-17-PRODUCING HELPER T CELLS, AND METHOD FOR DETECTION OF HUMAN IL-17-PRODUCING HELPER T CELLS

CROSS REFERENCE TO RELATED APPLICATIONS

This is a divisional of U.S. patent application Ser. No. 13/360,324, filed Jan. 27, 2012, which is a continuation of International Application PCT/JP2010/062807 filed Jul. 29, 2010, which claims benefit of JP 2009-176755, filed Jul. 29, 2009, all of which are incorporated herein by reference in their entirety.

BACKGROUND OF THE INVENTION

1. Field of the Invention

The present invention relates to a marker and reagent for detecting human IL-17-producing helper T-cells (hereinafter also referred to as "Th17 cells") and a method for detecting human Th17 cells.

2. Description of the Related Art

Rheumatoid arthritis (hereinafter referred to as "RA") is the systemic inflammatory autoimmune disease whose main clinical symptom is arthritis. The state of RA is diagnosed by rational symptoms such as joint pain or by visual procedures such as the observations on the extent of swelling or bone X-ray. However, no quantitative index has been established. Thus, no quantitative method for continuously monitoring the treatment effects has been established under the current state of the art.

The pathogenesis of RA has not been elucidated. It is considered that bacterial infections and the like trigger an inflammation in joint tissues via complicated networks of immunocytes and cytokines.

Helper T-cells play a central role in immune reactions. Immature helper T-cells (naïve T-cells) are differentiated into helper T-cells when an antigen is presented by antigen-presenting cells. When specific cytokines are present at this time, naïve T-cells are differentiated into four types of the cells, which are helper T-cells producing interferon (IFN)-γ (Th1 cells), helper T-cells producing interleukin (IL)-4 (Th2 cells), helper T-cells producing IL-17 (Th17 cells) and regulatory T-cells having immunosuppressive effects (Treg cells).

It has been shown that among these helper T-cells, Th17 cells can be involved in the onset of RA.

It has been suggested that IL-17 is deeply involved in the formation of pathological conditions and in particular joint and bone deformities because the level of IL-17 is significantly higher in synovial fluid of RA patients than in that of the patients of osteoarthritis and T-cells in synovial tissue from RA patients include IL-17 positive cells (see Japanese Unexamined Patent Publication No. 2000-186046). Japanese Unexamined Patent Publication No. 2000-186046 also discloses that IL-17 can be used as a diagnostic marker of RA.

Japanese Unexamined Patent Publication No. 2007-506100 discloses that the analysis of cytokines in peripheral blood serum of RA patients revealed that the levels of IFN-γ, IL-1β, TNF-α, G-CSF, GM-CSF, IL-6, IL-4, IL-10, IL-13, IL-5 and IL-7 were significantly high and the levels of IL-2, CXCL8/IL-8, IL-12 and CCL2/MCP-1 were not high in RA patients.

According to the studies by Ivanov et al. ("The Orphan Nuclear Receptor RORγt Directs the Differentiation Program of Proinflammatory IL-17+ T Helper Cells", Cell, 2006, 126, p. 1121-1133), Stumhofer et al. ("Interleukin 27 negatively regulates the development of interleukin 17-producing T helper cells during chronic inflammation of the central nervous system", Nature Immunology, 2006, vol. 7, p. 937-945), and Wilson et al. ("Development, cytokine profile and function of human interleukin 17-producing helper T cells", Nature Immunology, 2007, vol. 8, p. 950-95'7), the following facts have been shown about Th17 cells:

- a nuclear receptor called RORγt has an important role in the differentiation of Th17 cells;
- IL-6, IL-23 and TGF-β induce the differentiation of immature helper T-cells (naïve T-cells) to Th17 cells;
- they express IL-17A, IL-17F, IL-6, IL-22, IL-26, TNF, IFN-γ and CCL20; and
- IL-23 receptor and IL-12 receptor β are located on the surface of Th17 cells.

SUMMARY OF THE INVENTION

In the above documents by Ivanov et al., Stumhofer et al. and Wilson et al., the amount of IL-17 is measured by enzyme linked immunosorbent assay (ELISA) using antibodies specific to IL-17.

The relations between Th17 cells and autoimmune diseases, preferably RA may be more deeply understood by establishing a method which allows not only measurement of the amount of IL-17 but also detection of Th17 cells per se.

The present inventors aimed to find molecular markers that allows specific detection of human Th17 cells.

The present inventors isolated Th17 cells from peripheral blood of a healthy adult and identified the genes which are specifically expressed in the obtained Th17 cells, thereby completing the present invention.

Thus, the present invention provides a polynucleotide marker for detecting human Th17 cells which is a polynucleotide having a nucleic acid sequence of at least one gene selected from the group consisting of:

- genes encoding membrane proteins consisting of: ADAM12 (ADAM metallopeptidase domain 12), ANKS1B (ankyrin repeat and sterile alpha motif domain containing 1B), ATP6V0A4 (ATPase, H+ transporting, lysosomal V0 subunit a4), ATP9A (ATPase, class II, type 9A), BVES (blood vessel epicardial substance), C5orf40 (chromosome 5 open reading frame 40), CDH4 (cadherin 4, type 1, R-cadherin (retinal)), DIO2 (deiodinase, iodothyronine, type II), DMD (dystrophin), GPR34 (G protein-coupled receptor 34), IRS2 (insulin receptor substrate 2), KCNE3 (potassium voltage-gated channel, Isk-related family, member 3), L1CAM (L1 cell adhesion molecule), MCAM (melanoma cell adhesion molecule), MFAP3L (microfibrillar-associated protein 3-like), MYO7A (myosin VIIA), PTPRM (protein tyrosine phosphatase, receptor type, M), SHROOM2 (shroom family member 2), SLC16A4 (solute carrier family 16, member 4 (monocarboxylic acid transporter 5)), SLCO2B1 (solute carrier organic anion transporter family, member 2B1), TANC2 (tetratricopeptide repeat, ankyrin repeat and coiled-coil containing 2), TJP1 (tight junction protein 1 (zona occludens 1)), TMEM163 (transmembrane protein 163), TNS3 (tensin 3), UPK1B (uroplakin 1B), WDFY3 (WD repeat and FYVE domain containing 3), DRD2 (dopamine receptor D2), GJC1 (gap junction protein, gamma 1, 45 kDa), PGBD5 (LOC100134440) (piggyBac transposable element derived 5 (similar to PGBD5 protein)), MS4A 7 (membrane-spanning 4-domains, subfamily A, member 7), ODZ4 (odz, odd Oz/ten-m homolog 4), PHKA1 (phosphorylase kinase, alpha 1), RGS1 (regulator of G-protein signaling 1), SHB (Src homology 2 domain containing adaptor protein B), SLC44A3 (solute carrier family 44, member 3), SLC6A15 (solute carrier family 6 (neutral amino acid transporter), member 15), SYNGR3 (synaptogyrin 3), AKAP12 (A kinase (PRKA) anchor protein 12), C9orf125 (chromosome 9 open reading frame 125), DPY19L2 (dpy-19-like 2), HRH4 (histamine receptor H4), MUC20 (mucin 20, cell surface associated), POPDC3 (popeye domain containing 3), SORBS1 (sorbin and SH3 domain containing 1), TANC1 (tetratricopeptide repeat, ankyrin repeat and coiled-coil containing 1), TMEM44 (transmembrane protein 44) and UNC13C (unc-13 homolog C);

genes encoding secretory proteins consisting of: CXCL13 (chemokine (C—X—C motif) ligand 13), PCOLCE2 (procollagen C-endopeptidase enhancer 2), PNOC (prepronociceptin), SMPDL3A (sphingomyelin phosphodiesterase, acid-like 3A), TGFBI (transforming growth factor, beta-induced), C17orf99 (chromosome 17 open reading frame 99), EBI3 (Epstein-Barr virus induced 3), IL1A (interleukin 1, alpha) and WNT3 (wingless-type MMTV integration site family, member 3);

genes encoding intracellular proteins consisting of: BCAT1 (branched chain aminotransferase 1, cytosolic), BHLHE22 (basic helix-loop-helix family, member e22), C13orf18 (LOC728970) (chromosome 13 open reading frame 18 (hypothetical LOC728970)), CA2 (carbonic anhydrase II), CCDC3 (coiled-coil domain containing 3), CDS1 (CDP-diacylglycerol synthase (phosphatidate cytidylyltransferase) 1), CHN1 (chimerin (chimaerin) 1), CLIC5 (LOC100131610) (chloride intracellular channel 5 (similar to chloride intracellular channel 5)), CTSH (cathepsin H), CYP7B1 (cytochrome P450, family 7, subfamily B, polypeptide 1), DAPK2 (death-associated protein kinase 2), DMRT1 (doublesex and mab-3 related transcription factor 1), DSE (dermatan sulfate epimerase), FBXL17 (F-box and leucine-rich repeat protein 17), FBXL21 (F-box and leucine-rich repeat protein 21), FHOD3 (formin homology 2 domain containing 3), H2AFY2 (H2A histone family, member Y2), HLX (H2.0-like homeobox), IRAK3 (interleukin-1 receptor-associated kinase 3), MACC1 (metastasis associated in colon cancer 1), MAML3 (mastermind-like 3), MYO10 (myosin X), OTUB2 (OTU domain, ubiquitin aldehyde binding 2), PAPSS2 (3'-phosphoadenosine 5'-phosphosulfate synthase 2), PCBP3 (Poly (rC) binding protein 3 (PCBP3), transcript variant 2), PDE4DIP (phosphodiesterase 4D interacting protein), PLD1 (phospholipase D1, phosphatidylcholine-specific), PPARG (peroxisome proliferator-activated receptor gamma), PTPN13 (Protein tyrosine phosphatase, non-receptor type 13 (APO-1/CD95 (Fas)-associated phosphatase)), RGS18 (regulator of G-protein signaling 18), SIM1 (single-minded homolog 1), SNAI2 (snail homolog 2), SOX2 (SRY (sex determining region Y)-box 2), SPIRE1 (spire homolog 1), TBC1D12 (TBC1 domain family, member 12), TGM5 (transglutaminase 5), TMOD1 (tropomodulin 1), TUBB6 (tubulin, beta 6), DDIT4L (DNA-damage-inducible transcript 4-like), DHRS9 (dehydrogenase/reductase (SDR family) member 9), ERC2 (ELKS/RAB6-interacting/CAST family member 2), FERMT2 (fermitin family homolog 2), HHEX (hematopoietically expressed homeobox), HS3ST1 (heparan sulfate (glucosamine) 3-O-sulfotransferase 1), NR5A2 (nuclear receptor subfamily 5, group A, member 2), PHLDA1 (pleckstrin homology-like domain, family A, member 1), RBM20 (RNA binding motif protein 20), NINL (ninein-like), RTN2 (reticulon 2), SH3RF2 (SH3 domain containing ring finger 2), TSHZ2 (teashirt zinc finger homeobox 2), EML1 (echinoderm microtubule associated protein like 1), HIST1H2BC (histone cluster 1, H2bc), MAP3K4 (mitogen-activated protein kinase kinase kinase 4), PDK4 (pyruvate dehydrogenase kinase, isozyme 4), RGS2 (regulator of G-protein signaling 2) and RGS20 (regulator of G-protein signaling 20);

genes consisting of: C1orf106 (chromosome 1 open reading frame 106), C6orf145 (chromosome 6 open reading frame 145), LOC401097 (Similar to LOC166075), MAMLD1 (mastermind-like domain containing 1), ZC3H12C (zinc finger CCCH-type containing 12C), C12orf64 (chromosome 12 open reading frame 64), C6orf168 (chromosome 6 open reading frame 168), CAMSAP1L1 (calmodulin regulated spectrin-associated protein 1-like 1) and MAGED4 (MAGED4B) (melanoma antigen family D, 4, (melanoma antigen family D, 4B)); and genes comprising at least one nucleic acid sequence selected from SEQ ID NOs:147 to 151, 157 to 162 and 167 to 174;

or a variant and fragment thereof.

The present invention also provides a protein marker for detecting human Th17 cells which is a protein encoded by at least one of the above genes or a functionally equivalent variant and fragment thereof.

The present invention further provides a method for detecting human Th17 cells comprising detecting the presence of at least one polynucleotide marker for detecting human Th17 cells or at least one protein marker for detecting human Th17 cells in a sample containing cells derived from human.

In addition, the present invention provides a reagent for detecting human Th17 cells comprising at least one substance selected from a nucleic acid probe which specifically hybridizes to the above polynucleotide marker; and a nucleic acid aptamer, antibody, ligand or receptor which specifically binds to the above protein marker.

Human Th17 cells can be specifically detected by detecting at least one polynucleotide marker or protein marker for detecting human Th17 cells of the present invention. It may also allow detection of the possibility that a patient has a disease in which Th17 cells may be involved such as autoimmune diseases, e.g. RA.

DETAILED DESCRIPTION OF THE EMBODIMENTS

Figure 1:
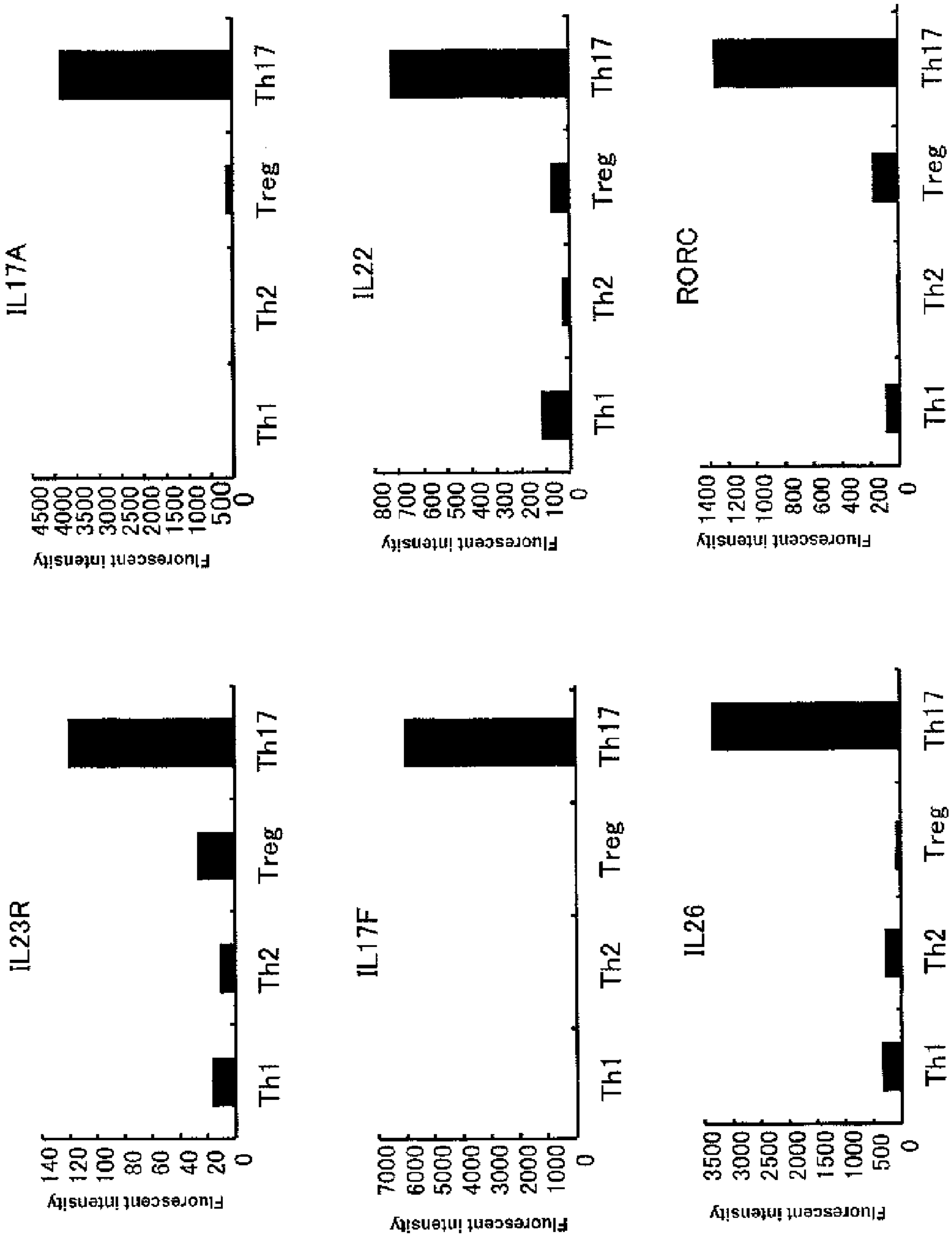
FIG. 1 shows graphs of the expression levels of the genes which are known to be specifically expressed in Th17 cells (IL23R, IL17A, IL17F, IL22, IL26 and RORC) in Th1, Th2, Treg and Th17 cells.

The polynucleotide marker for detecting human Th17 cells of the present invention is the polynucleotide having a nucleic acid sequence of at least one gene selected from the group consisting of the above genes, or a variant and fragment thereof.

Preferably, the polynucleotide has a nucleic acid sequence of at least one gene selected from the group consisting of:

genes encoding membrane proteins consisting of: ADAM12, ATP6V0A4, ATP9A, BVES, C5orf40, CDH4, DIO2, GPR34, L1CAM, MCAM, PTPRM, SHROOM2, TMEM163, UPK1B, DRD2, PGBD5 (LOC100134440), ODZ4, SLC6A15, AKAP12, C9orf125, POPDC3 and UNC13C;

genes encoding secretory proteins consisting of: PCOLCE2, PNOC, TGFBI and IL1A; and genes encoding intracellular proteins consisting of: BHLHE22, PPARG, SIM1 and SNAI2.

The present polynucleotide marker for detecting human Th17 cells is the polynucleotide, variant or fragment thereof which has been found to be specifically present in Th17 cells rather than in other helper T-cells derived from human peripheral blood (Th1, Th2 and Treg cells).

Therefore, by detecting at least one of the above polynucleotide markers, Th17 cells can be distinguished from Th1, Th2 and Treg cells and specifically identified, and an index for activity of diseases in vivo can be studied in which Th17 cells may be involved.

As used herein, the term "gene" has the same meaning as that is commonly recognized in the art, and refers to a part of a genome which is transcribed into mRNA and translated into a protein.

In the present specification, genes containing at least one nucleic acid sequence selected from SEQ ID NOs: 147 to 151, 157 to 162 and 167 to 174 are the genes to be transcribed into mRNAs containing at least one of these nucleic acid sequences or a complementary sequence thereof. Thus, genes containing at least one nucleic acid sequence selected from SEQ ID NOs: 147 to 151, 157 to 162 and 167 to 174 comprise genes containing a nucleic acid sequence complementary to at least one nucleic acid sequence selected from SEQ ID NOs: 147 to 151, 157 to 162 and 167 to 174.

As used herein, a membrane protein means a protein existing in a cell membrane and being contained in a membrane fraction of cells. A secretory protein means a protein synthesized in cells and secreted to the outside of the cell membrane. An intracellular protein means a protein which is mainly present in cells.

As used herein, the phrase that a polynucleotide is "specifically expressed" in Th17 cells means that the expression level of the polynucleotide in Th17 cells is significantly higher than the expression level of the polynucleotide in cells other than Th17 cells.

Specifically, it means that the expression level of the polynucleotide in Th17 cells is about two times or more of the expression level of the polynucleotide in cells other than Th17 cells. Preferably, the expression level of the polynucleotide in Th17 cells is about two times or more of the expression level of the polynucleotide in helper T-cells other than Th17 cells (Th1, Th2 and Treg cells).

The nucleotide sequences of the present polynucleotide markers are already known. They can be obtained from, for example, Unigene (a database provided by National Center for Biotechnology Information (NCBI) of National Library of Medicine). Unigene codes for the nucleic acid sequences of the present polynucleotide markers are specified in Table 9.

As used herein, "variant" of a polynucleotide means a polynucleotide into which a mutation has been introduced that does not alter the nature of the protein encoded by the above gene. Such mutation includes a deletion, substitution or addition of one or more nucleotides to the nucleic acid sequence of the above gene.

As used herein, "fragment" of a polynucleotide means a polynucleotide having a contiguous part of the nucleic acid sequence of the above gene and having a length which allows its specific hybridization with a nucleic acid probe for detecting human Th17 cells described hereinafter.

The variant of the polynucleotide as the present polynucleotide marker for detecting human Th17 cells has generally at least 80%, more preferably at least 85%, further preferably at least 90% and particularly preferably at least 95% homology with the nucleic acid sequence of the above gene.

As used herein, the homology of nucleic acid and amino acid sequences is calculated in BLASTN, BLASTP, BLASTX or TBLASTN (e.g. available from http://www.ncbi.nlm.nih.gov) with default settings.

The polynucleotide marker may be any of DNA or RNA, and may be the gene per se (DNA), mRNA, cDNA or cRNA.

Human Th17 cells can also be detected by detecting at least one protein encoded by the above gene. Thus, the present invention also provides the protein marker for detecting human Th17 cells consisting of the protein encoded by at least one of the above genes or a functionally equivalent variant and fragment thereof.

Preferably, the above protein is encoded by at least one gene selected from the group consisting of:

genes encoding membrane proteins consisting of: ADAM12, ATP6V0A4, ATP9A, BVES, C5orf40, CDH4, DIO2, GPR34, L1CAM, MCAM, PTPRM, SHROOM2, TMEM163, UPK1B, DRD2, PGBD5 (LOC100134440), ODZ4, SLC6A15, AKAP12, C9orf125, POPDC3 and UNC13C;

genes encoding secretory proteins consisting of: PCOLCE2, PNOC, TGFBI and IL1A; and genes encoding intracellular proteins consisting of: BHLHE22, PPARG, SIM1 and SNAI2.

More preferably, the above protein is a membrane protein encoded by at least one gene selected from the group consisting of GPR34, MCAM and PTPRM.

The amino acid sequence of such protein marker can be obtained based on the nucleic acid sequence of the polynucleotide marker obtained from Unigene and the like. It can also be obtained from databases provided by NCBI and the like. NCBI code numbers for the amino acid sequences of the present protein markers for detecting human Th17 cells are specified in Table 9.

The protein marker for detecting human Th17 cells is the protein encoded by the above gene, a functionally equivalent variant or fragment thereof.

As used herein, "functionally equivalent variant" of a protein means a protein into which a mutation has been introduced that does not alter functions of the protein. Such mutation includes a deletion, substitution or addition of one or more amino acids to the known amino acid sequence of the protein.

As used herein, "fragment" of a protein means a protein having a contiguous amino acid sequence of the protein encoded by the above gene or a functionally equivalent variant thereof and being able to specifically bind to a nucleic acid aptamer, antibody, ligand or receptor for detecting human Th17 cells described hereinafter.

The functionally equivalent variant of the protein corresponding to the present protein marker for detecting human Th17 cells has generally at least 80%, preferably at least 85%, more preferably at least about 90% and particularly preferably at least 95% homology with the known amino acid sequence of the protein encoded by the above gene.

A molecule that can specifically hybridize to the present polynucleotide marker can be used for detection of the marker, making it useful as a probe for detecting human Th17 cells. The probe may be a nucleic acid probe such as DNA or RNA, or a peptide probe that can specifically hybridize to the polynucleotide marker. The probe for detecting human Th17 cells is preferably a nucleic acid probe, particularly a DNA probe for detecting the polynucleotide marker.

As used herein, the phrase "can specifically hybridize" means that it can hybridize to a target nucleic acid molecule (the polynucleotide marker) under a stringent condition.

As used herein, "stringent condition" means a condition under which the probe for detecting human Th17 cells can hybridize to the target polynucleotide marker with a detectably higher extent than it does to a polynucleotide other than the target polynucleotide marker (e.g. more than at least two times of the background).

The stringent condition generally depends on the sequences and varies depending on various circumstances. Generally, the stringent condition is selected so that it is about 5° C. lower than a thermal melting point of the specific sequence under a certain ionic strength and pH. This Tm is a temperature at which 50% of the complementary probe hybridizes to the target sequence in equilibrium (under a certain ionic strength, pH and nucleic acid composition).

Such condition may be those which are used in conventional hybridization techniques between polynucleotides such as PCR, microarray or Southern blotting.

Specifically, it may be a condition of pH 7.0 to 9.0, a salt concentration of lower than about 1.5M Na-ion, more specifically about 0.01 to 1.0 M Na-ion concentration (or other salt) and a temperature of at least about 30° C. More specifically, the stringent condition in microarray technique includes the hybridization at 37° C. in 50% formamide, 1M NaCl and 1% SDS and washing at 60 to 65° C. in 0.1×SSC.

The stringent condition in PCR technique includes a condition of pH 7 to 9, 0.01 to 0.1 M Tris-HCl, 0.05 to 0.15 M potassium ion concentration (or other salt) and at least about 55° C.

The sequence of the nucleic acid probe for detecting human Th17 cells can be appropriately selected by a person skilled in the art based on the common technical knowledge in the art and the sequence of the polynucleotide marker so that it can specifically hybridize to the polynucleotide marker.

The nucleic acid probe for detecting human Th17 cells can be designed by using, for example, a commonly available primer designing software (e.g. Primer3 (available from frodo.wi.mit.edu/cgi-bin/primer3/primer3.cgi) or DNASIS Pro (Hitachi Software Engineering Co., Ltd.)).

The nucleic acid probe for detecting human Th17 cells can be prepared according to polynucleotide synthesis methods which are well-known in the art.

The nucleic acid probe for detecting human Th17 cells may be labeled with a labeling substance normally used in the art. The labeled nucleic acid probe allows an easy detection of the polynucleotide marker for detecting human Th17 cells, namely of human Th17 cells.

The labeling substance may be a labeling substance generally used in the art including radioisotopes such as $^{32}P$, fluorescent substances such as fluorescein, enzymes such as alkaline phosphatase and horseradish peroxidase, and biotin.

Human Th17 cells can be specifically detected by using one or more nucleic acid probes for detecting human Th17 cells. For example, a DNA chip or microarray for detecting the polynucleotide marker for detecting human Th17 cells can be obtained by immobilizing one or more probes on a substrate according to a method well-known in the art.

The nucleic acid probe for detecting human Th17 cells may include a set of two or more primers for amplifying the polynucleotide marker by nucleic acid amplification methods such as PCR technique, for example.

A molecule that can specifically bind to the present protein marker can be used for the detection of the marker, making it useful in the detection of human Th17 cells. Such molecule may be a nucleic acid aptamer such as DNA or RNA, an antibody, a ligand or a receptor that can specifically bind to the present protein marker, and preferably an antibody.

When the protein marker for detecting human Th17 cells is an enzyme, it can be detected by applying a substrate for the enzyme to develop color or emit light or fluorescent.

The antibody for detecting human Th17 cells can be prepared by the following well-known procedure, for example. A DNA molecule encoding a protein having an amino acid sequence of the present protein marker is prepared based on the nucleic acid sequence of the present polynucleotide marker or the amino acid sequence of the present protein marker, and is introduced into an appropriate expression vector. The obtained expression vector is introduced into an appropriate host cells, and the obtained transformed cells are cultured to obtain a desired protein. The obtained protein is purified and used as an immunogen optionally with an adjuvant to immunize an appropriate mammal such as rat or mouse. Spleen cells of the immunized animals are screened for antibody producing cells that produce an antibody directed to the target immunogen. The selected antibody producing cells are fused with myeloma cells to obtain hybridomas. These hybridomas are screened for antibody producing hybridomas that produce an antibody having specific binding property to the protein encoded by the gene. The desired antibody can be obtained by culturing the obtained antibody producing hybridomas.

The nucleic acid aptamer that can be used for detecting human Th17 cells can be prepared by the following well-known procedure, for example. A nucleic acid library including random nucleic acid sequences is prepared according to the known technique, and an aptamer that specifically binds to the target protein (the protein marker) can be selected by the systematic evolution of ligands by exponential enrichment method (SELEX method) or the like.

The molecule which can specifically bind to the protein marker for detecting human Th17 cells may be labeled with a labeling substance normally used in the art. The labeled antibody for detecting human Th17 cells allows an easy detection of the protein marker for detecting human Th17 cells, namely of human Th17 cells.

The labeling substance may be a labeling substance generally used in the art including radioisotopes such as $^{32}P$, fluorescent substances such as fluorescein, enzymes such as alkaline phosphatase and horseradish peroxidase, and biotin.

A method for detecting human Th17 cells by detecting the presence of at least one polynucleotide or protein marker for detecting human Th17 cells in a sample containing cells derived from human is also within the scope of the present invention.

In the method, it is preferred that two or more polynucleotide markers or protein markers for detecting human Th17 cells are detected in order to improve the detection sensitivity.

In the present method, the sample containing cells derived from human includes a biological sample obtained from human or a sample containing cultured human cells. The biological sample includes blood, tissue, synovial fluid, cerebrospinal fluid, pleural fluid, ascitic fluid and the like.

An embodiment of the method for detecting the presence of the polynucleotide marker for detecting human Th17 cells is described.

Nucleic acid (DNA or RNA) is extracted from a sample containing cells derived from human by a well-known method in the art such as the one using a phenolic extraction and ethanol precipitation or a commercial DNA extraction kit.

Then, the presence of the polynucleotide marker in the obtained nucleic acid sample is detected, preferably using the nucleic acid probe for detecting human Th17 cells. When the presence of the polynucleotide marker is detected by nucleic acid amplification method such as PCR, RT-PCR, real-time PCR, LAMP (Loop-mediated isothermal amplification) and the like, the nucleic acid probe for detecting human Th17 cells is preferably a primer set for amplifying the polynucleotide marker by a nucleic acid amplification method.

The presence of the polynucleotide marker for detecting human Th17 cells may also be detected by well-known methods in the art, for example hybridization methods such as Southern hybridization, Northern hybridization, fluorescence in situ hybridization (FISH), or DNA chip or microarray. Such methods are carried out under the stringent condition, and the hybridization of the nucleic acid probe for detecting human Th17 cells is detected by detecting the labeling substance and the like to detect the presence of the polynucleotide marker.

An embodiment of the method for detecting the presence of the protein marker for detecting human Th17 cells is described.

When the target protein marker is an intracellular protein, proteins are extracted from a sample containing cells derived from human by using well-known methods in the art. The extraction of proteins from a sample can be accomplished by known methods such as disruption of the cells by ultrasonic, lysis of the cells with a cell lysis solution. The protein marker in the obtained protein extract can be detected by using the molecule which specifically binds to the protein marker. Specifically, the protein marker for detecting human Th17 cells can be detected by well-known methods in the art such as ELISA or Western blotting. The molecule which specifically binds to the protein marker in the detection is preferably the above nucleic acid aptamer, antibody, ligand or receptor, and more preferably the antibody for detecting human Th17 cells.

When the target protein marker is a secretory protein, the protein marker secreted in the sample containing the cells can be detected by using the molecule which specifically binds to the protein marker.

Alternatively, the cells (lymphocytes) are recovered from the sample containing the cells from human and the obtained cells are stimulated with anti-CD3 antibody, anti-CD28 antibody, concanavalin A, phytohemagglutinin (PHA), phorbol myristate acetate (PMA), ionomycin or the like. Then, the secreted protein marker can be detected by using the molecule which specifically binds to the protein marker.

Specifically, the protein marker can be detected by well-known methods in the art such as ELISA or Western blotting. The molecule which specifically binds to the protein marker in the detection is preferably the above nucleic acid aptamer, antibody, ligand or receptor, and more preferably the antibody for detecting human Th17 cells.

When the target protein marker is a protein located on the cell surface, the protein marker located on the cell surface in the sample containing the cells derived from human can be detected by using the molecule which specifically binds to the protein marker.

Alternatively, a membrane fraction of the cells is obtained from the sample containing the cells derived from human and the protein marker in the membrane fraction can be detected by using the molecule which specifically binds to the protein marker. Specifically, the protein marker can be detected by well-known methods in the art such as ELISA, Western blotting or a method based on flow cytometry (FCM). The molecule which specifically binds to the protein marker in the detection is preferably the above nucleic acid aptamer, antibody, ligand or receptor, and more preferably the antibody for detecting human Th17 cells.

For example, the protein marker for detecting human Th17 cells can be detected by FCM as follows.

First, the sample containing the cells derived from human is brought into contact with the antibody for detecting human Th17 cells labeled with an appropriate labeling substance. Human Th17 cells, when exist, bind to the labeled antibody on their surfaces. Then, the sample containing the cells bound to the labeling substance can be applied to a flow cytometer to detect human Th17 cells. Human Th17 cells that have bound to the labeling substance can optionally be classified and fractionated by using a cell sorter.

Such method of FCM is well-known to a person skilled in the art and he can appropriately select the reaction conditions.

The present invention also provides a reagent for detecting human Th17 cells which can be used in the present method for detecting human Th17 cells The reagent comprises at least one substance selected from a nucleic acid probe which specifically hybridizes to the polynucleotide marker for detecting human Th17 cells, and a nucleic acid aptamer, antibody, ligand and receptor which specifically binds to the protein marker for detecting human Th17 cells.

The present invention is now described in detail by way of Examples, which do not limit the present invention.

EXAMPLE 1

Analysis of Highly Expressed Genes in Cultured Th17 Cells Derived from Human Peripheral Blood 1. Isolation of Th1, Th2, Treg and Th17 Cells from Human Peripheral Blood (1) Isolation of Th1, Th2 and Th17 Cells from Human Peripheral Blood Buffy coat obtained from peripheral blood of a healthy adult was overlaid on Ficoll-paque plus solution (GE Healthcare Bioscience) and centrifuged to obtain a monocyte fraction. Crude CD4 positive cells were purified from the fraction by using magnetic beads bound to anti-CD4 antibody (Miltenyi Biotec).

The obtained CD4 positive cells were stained with the fluorescence labeled antibodies shown in Table 1 and then Th1, Th2 and Th17 cells were separated by a cell sorter (FACS Aria: Becton Dickinson). The separation was carried out with the gating shown in Table 2.

TABLE 1

| Antigen | Fluorescence labeling substance | Clone | Manufacturer |
|---|---|---|---|
| CD4 | APC-Cy7 | RPA-T4 | BD Biosciences |
| CD25 | PE-Cy7 | BC96 | eBioscience |
| CXCR3 | Alexa Fluor ™ 488 | 1C6/CXCR3 | BD Biosciences |
| CCR4 | APC | FAB1567A | R&D systems |
| CCR6 | PE | 11A9 | BD Biosciences |

TABLE 2

| Cell | Gating |
|---|---|
| Th1 | $CD4^{high}$ $CD25^{low\text{-}negative}$ $CXCR3^{+}$ $CCR6^{-}$ $CCR4^{-}$ |
| Th2 | $CD4^{high}$ $CD25^{low\text{-}negative}$ $CXCR3^{-}$ $CCR6^{-}$ $CCR4^{+}$ |
| Th17 | $CD4^{high}$ $CD25^{low\text{-}negative}$ $CXCR3^{-}$ $CCR6^{+}$ $CCR4^{+}$ |

The above gating is described in detail in the reference by Acosta-Rodriguez E V et al. (Surface phenotype and antigenic specificity of human interleukin 17-producing T helper memory cells, Nat Immunol., 2007, vol. 8, p. 639-646).

(2) Isolation of Treg Cells from Human Peripheral Blood

CD4 positive cells obtained in the same manner as the above (1) were stained with the fluorescence labeled antibodies shown in Table 3, and CD4high CD25high CD127internal-negative cells were purified as Treg cells by using the above cell sorter.

TABLE 3

| Antigen | Fluorescence Labeling substance | Clone | Manufacturer |
|---|---|---|---|
| CD4 | FITC | OKT4 | eBioscience |
| CD25 | PE-Cy7 | BC96 | eBioscience |
| GD45RO | PE | UCHL1 | BioLegend |
| CD127 | Alexa Fluor ™ 647 | HIL-7R-M21 | BD Biosciences |

The above gating is described in detail in the reference by Weihong Liu et al. (CD 127 expression inversely correlates with FoxP3 and suppressive function of human CD4+ T reg cells, J Exp Med. 2006, vol. 203, p. 1701-1711).

2. Cell Culture (1) Th1, Th2 and Th17 Cell Cultures

Th1, Th2 and Th17 cells derived from adult peripheral blood obtained in the above step 1. (1) were respectively plated in a 96-well plate at the density of $1.5\times10^5$ cells/0.3 ml/well. The medium used was Yssel medium (IMDM, 1% human serum of AB-type, 0.25% BSA, 1.8 mg/l 2-aminomethanol, 40 mg/l transferrin, 5 mg/l insulin, 2 mg/l linoleic acid, 2 mg/l oleic acid, 2 mg/l palmitic acid, 1% penicillin/streptomycin).

For activation and proliferation of the above cells, magnetic beads coated with anti-CD2/3/28 antibody (Miltenyi Biotec) (hereinafter also referred to as “antibody beads”) were added at $0.75\times10^5$ per well. After addition of cytokines and neutralizing antibody(s) suitable for differentiation culture of respective Th1, Th2 and Th17 cells, cells were incubated in an incubator at 37° C. with 5% $CO_2$. Cytokines and neutralizing antibodies used are shown in Table 4.

TABLE 4

| Cell | Cytokine | Neutralizing antibody (Clone) |
|---|---|---|
| Th1 | IL-12, IL-2 | Anti-IL-4 antibody (MP4-25D2) |
| Th2 | IL-4, IL-2 | Anti-IFN-γ antibody (R4-6A2) |
| Th17 | TGF-β1, IL-6, IL-23, IL-21, IL-1β, TNFα, IL-2 | Anti-IL-4 antlbody (MP4-25D2), Anti-IFN-γ antibody (R4-6A2) |

The concentrations of the above cytokines were 50 ng/ml for IL-6 and 10 ng/ml for other than IL-6.

The concentrations of antibodies were 10 μg/ml for anti-IFN-γ antibody and 2.5 μg/ml for anti-IL-4 antibody. The cytokines and neutralizing antibodies were obtained from R&D systems and eBioscience, respectively.

After three days from the start of culture, cells were diluted three-fold with the medium containing the above cytokines and antibody(s) and cultured for further seven days (10 days in total).

After ten days from the start of culture, the obtained Th1, Th2 and Th17 cells were respectively divided into two equal parts, and one was washed with Yssel medium and PBS before centrifugation to collect cells, which were stored at −80° C. until the subsequent RNA extraction step. These cells were designated as Th1, Th2 and Th17 cells “without activation stimulation”. The other half was added with the antibody beads and cultured for three more hours to re-activate the cells. The cells were collected by centrifugation and similarly stored at −80° C. These cells were designated as Th1, Th2 and Th17 cells “with activation stimulation”.

(2) Treg Cell Culture

Treg cells obtained in the above step 1. (2) were cultured in the same manner in Yssel medium as the above step 2. (1) and activated with the antibody beads. To the medium were added cytokines IL-2 and TGF-β1 (R&D systems), and neutralizing antibodies anti-IFN-γ antibody, anti-IL-4 antibody (eBioscience) and anti-IL-6 antibody (BD Bioscience).

These cytokines and neutralizing antibodies were used at the concentrations of 10 ng/ml and 5 μg/ml, respectively.

After three days from the start of culture, cells were added with the cytokines and neutralizing antibodies at the same amounts as those at the start of the culture. After culturing for three more days, cells were divided into two equal parts, one half was not added with the antibody beads used for activation and the other half was added with the antibody beads before culturing further three hours, thereby obtaining Treg cells “without activation stimulation” and Treg cells “with activation stimulation”, respectively. The cells were then collected by centrifugation and stored at −80° C. until the subsequent RNA extraction step.

3. Extraction of Total RNA

The cells obtained as the above step 2. were subjected to extraction of total RNAs using RNeasy Plus Mini kit and RNeasy micro kit (QIAGEN).

The specific procedures were according to the attached instructions of the kits.

4. Expression Analysis by Microarray

Total RNAs (10 to 100 ng) extracted from the cells as the above step 3. were reverse-transcribed to cDNAs with Two-Cycle Target Labeling and Control Reagents (Affymetrix), and further transcribed to biotinylated-cRNAs. The amplified biotinylated-cRNAs (20 μg) were fragmented. The specific procedures were according to the attached instruction of the kit.

The biotinylated-cRNAs derived from the cells as obtained above (15 μg) were applied to GeneChip Human Genome U-133 Plus 2.0 Array (Affymetrix) as samples, transferred to GeneChip Hybridization Oven 640 (Affymetrix) and hybridized under the conditions of 45° C. and 60 rpm for 16 hours.

After completion of the hybridization, the microarray was washed and fluorescence-labeled in GeneChip Fluidic Station 450 (Affymetrix), and scanned in GeneChip Scanner 3000 7G (Affymetrix) to obtain fluorescent intensity data.

5. Selection of Genes Specifically Expressed in Human Th17 Cells

The fluorescent data obtained in the above step 4. was standardized with the expression analysis software GeneSpring Ver. 10 (Agilent Technologies) based on MAS5 algorithm. Relative fluorescent intensities of the genes from Th17 cells were compared with those from Th1, Th2 and Treg cells.

The genes whose relative fluorescent intensities in Th17 cells were three or more times higher than any of those of Th1, Th2 and Treg cells and which were significantly expressed (which showed “p value <0.05” after ANOVA test between four groups of relative fluorescent intensities in Th1, Th2, Treg and Th17 cells) were identified as the genes which were specifically expressed in Th17 cells.

The number of samples used in the above selection step is shown in Table 5.

TABLE 5

| | Th1 | Th2 | Th17 | Treg |
|---|---|---|---|---|
| w/ activation stimulation | 5 | 5 | 5 | 4 |
| w/o activation stimulation | 5 | 5 | 5 | 3 |

The genes specifically expressed in Th17 cells “without activation stimulation” and “with activation stimulation” are shown in Tables 6 and 7, respectively.

TABLE 6

| Without activation stimulation | | | | | | | | | |
|---|---|---|---|---|---|---|---|---|---|
| | | | | | | | Expression ratio | | |
| Location of encoded protein | Gene symbol | Entrez Gene ID | Protein ID | Transcript ID | UniGene ID | Probe Set ID | Th17/ Th1 | Th17/Th2 | Th17/Treg |
| Membrane | ADAM12 | 8038 | NP_003465, NP_067673 | NM_003474, NM_021641 | Hs.594537 | 202952_s_at | 21.8 | 80.1 | 3.2 |
| | ANKS1B | 56899 | NP_064525, NP_690001, NP_858056 | NM_020140, NM_152788, NM_181670 | Hs.506458 | 227439_at<br>240292_x_at | 6.9<br>7.8 | 11.7<br>10.3 | 4.3<br>4.6 |
| | ATP6V0A4 | 50617 | NP_065683, NP_570855, NP_570856 | NM_020632, NM_130840, NM_130841 | Hs.98967 | 220197_at | 22.8 | 244.1 | 153.8 |
| | ATP9A | 10079 | NP_006036 | NM_006045 | Hs.714307 | 212062_at | 5.7 | 53.5 | 44.3 |
| | BVES | 11149 | NP_009004, NP_671488 | NM_007073, NM_147147 | Hs.221660 | 228783_at | 3.0 | 6.5 | 16.2 |
| | C5orf40 | 408263 | NP_001001343 | NM_001001343 | Hs.437066 | 1554801_at | 9.4 | 12.8 | 3.1 |
| | CDH4 | 1002 | NP_001785 | NM_001794 | Hs.473231 | 206866_at | 19.2 | 16.0 | 7.6 |
| | DIO2 | 1734 | NP_000784, NP_001007024, NP_054644 | NM_000793, NM_001007023, NM_013989 | Hs.202354 | 203700_s_at | 9.2 | 3.4 | 17.1 |
| | DMD | 1756 | NP_000100, NP_003997, NP_003998, NP_004000, NP_004001, NP_004002, NP_004003, NP_004004, NP_004005, NP_004006, NP_004007, NP_004008, NP_004009, NP_004010, NP_004011, NP_004012, NP_004013, NP_004014 | NM_000109, NM_004006, NM_004007, NM_004009, NM_004010, NM_004011, NM_004012, NM_004013, NM_004014, NM_004015, NM_004016, NM_004017, NM_004018, NM_004019, NM_004020, NM_004021, NM_004022, NM_004023 | Hs.495912 | 203881_s_at | 10.3 | 3.2 | 10.0 |
| | DRD2 | 1813 | NP_000786, NP_057658 | NM_000795, NM_016574 | Hs.73893 | 216938_x_at | 5.3 | 5.6 | 5.4 |
| | GJC1 | 10052 | NP_001073852, NP_005488 | NM_001080383, NM_005497 | Hs.532593 | 228776_at<br>243502_at | 7.0<br>3.8 | 10.7<br>10.5 | 4.9<br>8.3 |
| | GPR34 | 2857 | NP_001091048, NP_005291 | NM_001097579, NM_005300 | Hs.495989 | 223620_at | 4.2 | 7.9 | 7.0 |
| | IL23R | 149233 | NP_653302 | NM_144701 | Hs.677426 | 1552912_a_at | 8.2 | 15.3 | 4.1 |
| | IRS2 | 8660 | NP_003740 | NM_003749 | Hs.442344 | 209184_s_at<br>209185_s_at | 3.5<br>6.0 | 4.0<br>5.9 | 3.3<br>4.3 |
| | KCNE3 | 10008 | NP_005463 | NM_005472 | Hs.523899 | 227647_at | 9.8 | 8.3 | 5.9 |
| | L1CAM | 3897 | NP_000416, NP_076493 | NM_000425, NM_024003 | Hs.522818 | 204584_at | 8.5 | 9.4 | 5.1 |
| | PGBD5, LOC100134440 | 79605, 100134440 | NP_078830, XP_001716155 | NM_024554, XM_001716103 | Hs.520463 | 219225_at | 9.9 | 17.3 | 11.3 |
| | MCAM | 4162 | NP_006491 | NM_006500 | Hs.599039 | 210869_s_at | 9.5 | 18.0 | 5.6 |
| | MFAP3L | 9848 | NP_001009554, NP_067679 | NM_001009554, NM_021647 | Hs.593942 | 205442_at | 11.5 | 29.9 | 7.1 |
| | MS4A7 | 58475 | NP_067024, NP_996821, NP_996822, NP_996823 | NM_021201, NM_206938, NM_206939, NM_206940 | Hs.530735 | 223343_at | 16.6 | 11.7 | 3.2 |
| | MYO7A | 4647 | NP_000251, NP_001120651, NP_001120652 | NM_000260, NM_001127179, NM_001127180 | Hs.370421 | 208189_s_at | 19.4 | 22.9 | 6.5 |
| | ODZ4 | 26011 | NP_001092286 | NM_001098816 | Hs.213087 | 213273_at | 9.8 | 13.1 | 7.0 |
| | PHKA1 | 5255 | NP_001116142, NP_002628 | NM_001122670, NM_002637 | Hs.201379 | 229876_at | 4.2 | 3.7 | 15.8 |
| | PTPRM | 5797 | NP_001098714, NP_002836 | NM_001105244, NM_002845 | Hs.49774 | 1555579_s_at | 3.6 | 76.0 | 3.7 |
| | RGS1 | 5996 | NP_002913 | NM_002922 | Hs.75256 | 202988_s_at | 3.3 | 3.6 | 3.9 |
| | SHB | 6461 | NP_003019 | NM_003028 | Hs.521482 | 1557458_s_at | 14.9 | 27.8 | 7.4 |
| | SHROOM2 | 357 | NP_001640 | NM_001649 | Hs.567236 | 204967_at | 3.4 | 3.4 | 3.4 |
| | SLC16A4 | 9122 | NP_004687 | NM_004696 | Hs.351306 | 205234_at | 66.3 | 20.4 | 3.4 |
| | SLC44A3 | 126969 | NP_001107578, NP_689582 | NM_001114106, NM_152369 | Hs.483423 | 228221_at | 3.1 | 9.3 | 3.5 |
| | SLC6A15 | 55117 | NP_060527, NP_877499 | NM_018057, NM_182767 | Hs.44424 | 206376_at | 10.7 | 11.9 | 15.2 |
| | SLCO2B1 | 11309 | NP_009187 | NM_007256 | Hs.7884 | 203473_at | 9.7 | 6.0 | 6.8 |
| | SYNGR3 | 9143 | NP_004200 | NM_004209 | Hs.435277 | 205691_at | 4.7 | 7.9 | 5.5 |

TABLE 6-continued

| Without activation stimulation | | | | | | | | | |
|---|---|---|---|---|---|---|---|---|---|
| | | | | | | | Expression ratio | | |
| Location of encoded protein | Gene symbol | Entrez Gene ID | Protein ID | Transcript ID | UniGene ID | Probe Set ID | Th17/Th1 | Th17/Th2 | Th17/Treg |
| | TANC2 | 26115 | NP_079461 | NM_025185 | Hs.410889 | 208425_s_at | 4.7 | 9.0 | 7.3 |
| | | | | | | 224952_at | 6.1 | 5.8 | 7.5 |
| | TJP1 | 7082 | NP_003248, | NM_003257, | Hs.716406 | 202011_at | 15.3 | 19.2 | 4.3 |
| | | | NP_783297 | NM_175610 | | | | | |
| | TMEM163 | 81615 | NP_112185 | NM_030923 | Hs.369471 | 1552626_a_at | 16.1 | 32.5 | 16.4 |
| | | | | | | 223503_at | 28.8 | 47.9 | 29.7 |
| | TNS3 | 64759 | NP_073585 | NM_022748 | Hs.520814 | 217853_at | 7.6 | 158.8 | 4.5 |
| | UPK1B | 7348 | NP_008883 | NM_006952 | Hs.271580 | 210065_s_at | 5.8 | 7.5 | 4.6 |
| | WDFY3 | 23001 | NP_055806, | NM_014991, | Hs.480116 | 212598_at | 14.2 | 18.4 | 45.6 |
| | | | NP_848698, | NM_178583, | | 212602_at | 18.7 | 56.1 | 29.3 |
| | | | NP_848700 | NM_178585 | | 212606_at | 23.0 | 82.7 | 71.7 |
| Extracellular/ | C17orf99 | 100141515 | NP_001156547 | NM_001163075 | Hs.633034 | 236981_at | 29.1 | 10.9 | 4.1 |
| secreted | CXCL13 | 10563 | NP_006410 | NM_006419 | Hs.100431 | 205242_at | 57.7 | 20.1 | 4.6 |
| | EBI3 | 10148 | NP_005746 | NM_005755 | Hs.501452 | 219424_at | 3.6 | 43.8 | 3.7 |
| | IL17A | 3605 | NP_002181 | NM_002190 | Hs.41724 | 216876_s_at | 340.3 | 618.9 | 21.8 |
| | IL17F | 112744 | NP_443104 | NM_052872 | Hs.272295 | 234408_at | 559.0 | 778.4 | 525.7 |
| | IL1A | 3552 | NP_000566 | NM_000575 | Hs.1722 | 210118_s_at | 38.1 | 13.8 | 6.5 |
| | IL22 | 50616 | NP_065386 | NM_020525 | Hs.287369 | 222974_at | 7.5 | 26.0 | 13.6 |
| | IL26 | 55801 | NP_060872 | NM_018402 | Hs.272350 | 221111_at | 11.6 | 13.5 | 53.7 |
| | IL9 | 3578 | NP_000581 | NM_000590 | Hs.960 | 208193_at | 103.8 | 193.5 | 24.1 |
| | PCOLCE2 | 26577 | NP_037495 | NM_013363 | Hs.8944 | 219295_s_at | 10.6 | 16.8 | 25.3 |
| | PNOC | 5368 | NP_006219 | NM_006228 | Hs.88218 | 205901_at | 36.8 | 27.3 | 69.3 |
| | SMPDL3A | 10924 | NP_006705 | NM_006714 | Hs.486357 | 213624_at | 4.0 | 3.8 | 7.9 |
| | TGFBI | 7045 | NP_000349 | NM_000358 | Hs.369397 | 201506_at | 54.7 | 476.7 | 33.8 |
| | WNT3 | 7473 | NP_110380 | NM_030753 | Hs.445884 | 229103_at | 6.6 | 5.9 | 6.2 |
| Intracellular | BCAT1 | 586 | NP_005495 | NM_005504 | Hs.438993 | 214390_s_at | 3.1 | 4.1 | 18.9 |
| | | | | | | 214452_at | 3.5 | 6.4 | 24.8 |
| | | | | | | 225285_at | 3.0 | 3.5 | 31.5 |
| | | | | | | 226517_at | 3.1 | 3.5 | 38.3 |
| | BHLHE22 | 27319 | NP_689627 | NM_152414 | Hs.591870 | 228636_at | 18.9 | 24.7 | 40.5 |
| | C13orf18, | 80183, | NP_079389, | NM_025113, | Hs.98117 | 44790_s_at | 3.2 | 11.2 | 32.0 |
| | LOC728970 | 728970 | XP_001132115, | XM_001132115, | | | | | |
| | | | XP_001133896, | XM_001133896, | | | | | |
| | | | XP_001720207 | XM_001720155 | | | | | |
| | CA2 | 760 | NP_000058 | NM_000067 | Hs.155097 | 209301_at | 6.3 | 452.7 | 103.6 |
| | CCDC3 | 83643 | NP_113643 | NM_031455 | Hs.498720 | 223316_at | 16.3 | 106.1 | 42.1 |
| | CDS1 | 1040 | NP_001254 | NM_001263 | Hs.654899 | 205709_s_at | 13.9 | 26.7 | 3.8 |
| | CHN1 | 1123 | NP_001020372, | NM_001025201, | Hs.654534 | 212624_s_at | 6.9 | 12.3 | 6.4 |
| | | | NP_001813 | NM_001822 | | | | | |
| | CLIC5, | 53405, | NP_001107558, | NM_001114086, | Hs.485489 | 213317_at | 6.7 | 53.5 | 13.3 |
| | LOC100131610 | 100131610 | NP_058625, | NM_016929, | | 217628_at | 3.1 | 9.1 | 4.2 |
| | | | XP_001723610 | XM_001723558 | | 243917_at | 13.9 | 56.8 | 16.7 |
| | | | | | | 219866_at | 7.1 | 28.2 | 17.8 |
| | CTSH | 1512 | NP_004381, | NM_004390, | Hs.148641 | 202295_s_at | 4.7 | 10.4 | 5.6 |
| | | | NP_683880 | NM_148979 | | | | | |
| | CYP7B1 | 9420 | NP_004811 | NM_004820 | Hs.667720 | 207386_at | 12.3 | 10.2 | 4.1 |
| | DAPK2 | 23604 | NP_055141 | NM_014326 | Hs.237886 | 206324_s_at | 7.3 | 9.9 | 8.3 |
| | | | | | | 215184_at | 6.3 | 11.0 | 7.1 |
| | DDIT4L | 115265 | NP_660287 | NM_145244 | Hs.480378 | 228057_at | 3.1 | 5.2 | 106.8 |
| | DHRS9 | 10170 | NP_001135742, | NM_001142270, | Hs.179608 | 219799_s_at | 8.3 | 14.6 | 11.9 |
| | | | NP_001135743, | NM_001142271, | | 223952_x_at | 5.3 | 7.8 | 7.7 |
| | | | NP_005762, | NM_005771, | | 224009_x_at | 6.3 | 7.9 | 7.0 |
| | | | NP_954674 | NM_199204 | | | | | |
| | DMRT1 | 1761 | NP_068770 | NM_021951 | Hs.98586 | 220493_at | 3.6 | 16.6 | 6.4 |
| | DSE | 29940 | NP_001074445, | NM_001080976, | Hs.486292 | 218854_at | 13.9 | 41.8 | 26.2 |
| | | | NP_037484 | NM_013352 | | | | | |
| | ERC2 | 26059 | NP_056391 | NM_015576 | Hs.476389 | 213938_at | 3.5 | 6.1 | 6.1 |
| | FBXL17 | 64839 | NP_073735 | NM_022824 | Hs.657225 | 227203_at | 8.9 | 7.7 | 4.7 |
| | FBXL21 | 26223 | NP_036291 | NM_012159 | Hs.591275 | 1555412_at | 22.9 | 29.2 | 13.0 |
| | FERMT2 | 10979 | NP_001128471, | NM_001134999, | Hs.509343 | 209210_s_at | 3.1 | 9.5 | 5.8 |
| | | | NP_001128472, | NM_001135000, | | | | | |
| | | | NP_006823 | NM_006832 | | | | | |
| | FHOD3 | 80206 | NP_079411 | NM_025135 | Hs.436636 | 218980_at | 7.2 | 10.3 | 7.8 |
| | H2AFY2 | 55506 | NP_061119 | NM_018649 | Hs.499953 | 218445_at | 5.2 | 6.5 | 6.4 |
| | HHEX | 3087 | NP_002720 | NM_002729 | Hs.118651 | 204689_at | 3.6 | 5.9 | 6.4 |
| | HLX | 3142 | NP_068777 | NM_021958 | Hs.74870 | 214438_at | 4.1 | 8.4 | 26.3 |
| | HS3ST1 | 9957 | NP_005105 | NM_005114 | Hs.507348 | 205466_s_at | 21.2 | 6.0 | 3.2 |
| | IRAK3 | 11213 | NP_001135995, | NM_001142523, | Hs.369265 | 213817_at | 14.5 | 16.5 | 6.0 |
| | | | NP_009130 | NM_007199 | | 220034_at | 5.5 | 10.3 | 3.4 |

TABLE 6-continued

Without activation stimulation

| Location of encoded protein | Gene symbol | Entrez Gene ID | Protein ID | Transcript ID | UniGene ID | Probe Set ID | Expression ratio Th17/Th1 | Th17/Th2 | Th17/Treg |
|---|---|---|---|---|---|---|---|---|---|
| | MACC1 | 346389 | NP_877439 | NM_182762 | Hs.598388 | 1566766_a_at | 5.9 | 15.7 | 3.5 |
| | MAML3 | 55534 | NP_061187 | NM_018717 | Hs.586165 | 242794_at | 5.4 | 5.7 | 4.1 |
| | MYO10 | 4651 | NP_036466 | NM_012334 | Hs.481720 | 201976_s_at | 39.5 | 17.2 | 7.1 |
| | NR5A2 | 2494 | NP_003813, NP_995582 | NM_003822, NM_205860 | Hs.33446 | 208343_s_at | 5.5 | 17.9 | 39.5 |
| | OTUB2 | 78990 | NP_075601 | NM_023112 | Hs.278815 | 219369_s_at | 3.4 | 3.7 | 6.3 |
| | | | | | | 222878_s_at | 3.2 | 3.2 | 6.6 |
| | PAPSS2 | 9060 | NP_001015880, NP_004661 | NM_001015880, NM_004670 | Hs.524491 | 203058_s_at | 4.4 | 5.1 | 19.5 |
| | | | | | | 203060_s_at | 6.6 | 17.0 | 14.3 |
| | PCBP3 | 54039 | NP_001123613, NP_065389 | NM_001130141, NM_020528 | Hs.474049 | 230486_at | 4.1 | 3.6 | 4.8 |
| | PDE4DIP | 9659 | NP_001002810, NP_001002811, NP_001002812, NP_055459, NP_071754 | NM_001002810, NM_001002811, NM_001002812, NM_014644, NM_022359 | Hs.654651 | 205872_x_at | 4.3 | 33.4 | 3.3 |
| | | | | | Hs.613082 | 209700_x_at | 4.1 | 10.9 | 9.5 |
| | PHLDA1 | 22822 | NP_031376 | NM_007350 | Hs.602085 | 217999_s_at | 3.6 | 5.0 | 10.3 |
| | | | | | | 225842_at | 3.3 | 3.2 | 8.0 |
| | PLD1 | 5337 | NP_001123553, NP_002653 | NM_001130081, NM_002662 | Hs.382865 | 177_at | 3.5 | 3.4 | 10.3 |
| | | | | | | 215723_s_at | 3.9 | 3.4 | 11.4 |
| | | | | | | 226636_at | 5.7 | 3.6 | 13.1 |
| | PPARG | 5468 | NP_005028, NP_056953, NP_619725, NP_619726 | NM_005037, NM_015869, NM_138711, NM_138712 | Hs.162646 | 208510_s_at | 7.9 | 134.5 | 16.5 |
| | PTPN13 | 5783 | NP_006255, NP_542414, NP_542415, NP_542416 | NM_006264, NM_080683, NM_080684, NM_080685 | Hs.436142 | 243792_x_at | 3.5 | 4.2 | 7.9 |
| | RBM20 | 282996 | NP_001127835, XP_001716171, XP_291671, XP_944430 | NM_001134363, XM_001716119, XM_291671, XM_939337 | Hs.715766 | 238763_at | 8.0 | 3.5 | 3.0 |
| | RGS18 | 64407 | NP_570138 | NM_130782 | Hs.440890 | 223809_at | 3.3 | 6.9 | 8.8 |
| | RORC | 6097 | NP_001001523, NP_005051 | NM_001001523, NM_005060 | Hs.256022 | 228806_at | 14.0 | 170.6 | 7.7 |
| | NINL | 22981 | NP_079452 | NM_025176 | Hs.696157 | 207705_s_at | 4.7 | 4.7 | 3.1 |
| | RTN2 | 6253 | NP_005610, NP_996783, NP_996784 | NM_005619, NM_206900, NM_206901 | Hs.47517 | 34408_at | 3.7 | 4.6 | 4.5 |
| | SH3RF2 | 153769 | NP_689763 | NM_152550 | Hs.443728 | 243582_at | 5.8 | 4.1 | 18.5 |
| | SIM1 | 6492 | NP_005059 | NM_005068 | Hs.520293 | 1556300_s_at | 8.8 | 4.8 | 69.0 |
| | | | | | | 206876_at | 8.7 | 4.8 | 37.5 |
| | SNAI2 | 6591 | NP_003059 | NM_003068 | Hs.360174 | 213139_at | 24.6 | 22.5 | 13.8 |
| | SOX2 | 6657 | NP_003097 | NM_003106 | Hs.518438 | 228038_at | 9.6 | 8.3 | 3.4 |
| | SPIRE1 | 56907 | NP_001122098, NP_001122099, NP_064533 | NM_001128626, NM_001128627, NM_020148 | Hs.515283 | 1554807_a_at | 4.7 | 6.1 | 3.8 |
| | | | | | | 224995_at | 8.0 | 9.0 | 4.7 |
| | | | | | | 225018_at | 6.6 | 9.2 | 6.3 |
| | TBC1D12 | 23232 | NP_056003 | NM_015188 | Hs.500598 | 221858_at | 7.7 | 5.8 | 5.5 |
| | TGM5 | 9333 | NP_004236, NP_963925 | NM_004245, NM_201631 | Hs.129719 | 207911_s_at | 3.6 | 6.6 | 5.1 |
| | TMOD1 | 7111 | NP_003266 | NM_003275 | Hs.494595 | 203661_s_at | 7.0 | 14.7 | 5.1 |
| | | | | | | 203662_s_at | 7.8 | 14.5 | 4.5 |
| | TSHZ2 | 128553 | NP_775756 | NM_173485 | Hs.649877 | 220213_at | 3.6 | 12.4 | 3.8 |
| | | | | | Hs.271605 | 243940_at | 3.1 | 10.6 | 4.1 |
| | TUBB6 | 84617 | NP_115914 | NM_032525 | Hs.193491 | 209191_at | 4.1 | 12.7 | 4.7 |
| Unknown | C1orf106 | 55765 | NP_001136041, NP_060735 | NM_001142569, NM_018265 | Hs.518997 | 219010_at | 78.5 | 111.8 | 3.3 |
| | C6orf145 | 221749 | NP_899229 | NM_183373 | Hs.484500 | 212923_s_at | 10.4 | 3.8 | 5.2 |
| | LOC401097 | 401097 | XP_001717155, XP_001718614, XP_001718795 | XM_001717103, XM_001718562, XM_001718743 | Hs.710781 | 236738_at | 6.8 | 3.3 | 24.9 |
| | MAMLD1 | 10046 | NP_005482 | NM_005491 | Hs.20136 | 205088_at | 6.6 | 8.3 | 34.1 |
| | ZC3H12C | 85463 | NP_203748 | NM_033390 | Hs.376289 | 231899_at | 3.0 | 4.1 | 18.7 |
| | — | — | — | AA579799, AA947186, AL049337, AW665328 | Hs.663788 | 215768_at | 4.1 | 6.1 | 6.7 |

TABLE 6-continued

| Location of encoded protein | Gene symbol | Entrez Gene ID | Protein ID | Transcript ID | UniGene ID | Probe Set ID | Th17/Th1 | Th17/Th2 | Th17/Treg |
|---|---|---|---|---|---|---|---|---|---|
| Without activation stimulation | | | | | | | | | |
| | — | — | — | AK093229 | Hs.586723 | 222900_at | 5.9 | 3.0 | 4.5 |
| | — | — | — | AK055628, uc001ljj.1 | Hs.594351 | 226777_at | 21.6 | 39.7 | 3.6 |
| | — | — | — | AK129763, CR595588, uc002jiy.1, uc002jiz.1 | Hs.157726 | 227452_at | 4.6 | 4.2 | 4.5 |
| | — | — | — | AA416573, AA628762, D53835, D53836, H24473, R37871, R40232, T10348, T23451, W56351, W57867, Z28733 | Hs.654918 | 229951_x_at | 4.7 | 15.0 | 7.1 |
| | — | — | — | AI766299 | — | 236338_at | 4.3 | 4.4 | 3.3 |
| | — | — | — | AI262017, AI280978, AI284950, AI733224, AI733801 | Hs.666775 | 237923_at | 6.9 | 5.3 | 4.0 |

TABLE 7

| Location of encoded protein | Gene symbol | Entrez Gene ID | Protein ID | Transcript ID | UniGene ID | Probe Set ID | Expression ratio Th17/Th1 | Th17/Th2 | Th17/Treg |
|---|---|---|---|---|---|---|---|---|---|
| Without activation stimulation | | | | | | | | | |
| Unknown | — | — | — | AA687415, AA96901, AI291640, AI446064, AI634557, AI694948, AI701854, AI983938, AV745212, AV745909, AV746001, AW008696, AW511701, AW974416, BG149302, BG150103, N66771, R66991 | Hs.434948 | 238009_at | 4.0 | 19.0 | 27.6 |
| | — | — | — | AI148241, AI735444, BE645654, BF510855, BF511636 | Hs.659083 | 238151_at | 50.6 | 21.1 | 24.4 |
| | — | — | — | AK094629 | Hs.594896 | 238623_at | 4.9 | 4.8 | 3.4 |
| | — | — | — | AI682088, AI951058, F06296, F13164, T77624, Z44722 | Hs.606172 | 241726_at | 5.4 | 5.7 | 9.5 |

TABLE 7-continued

| Location of encoded protein | Gene symbol | Entrez Gene ID | Protein ID | Transcript ID | UniGene ID | Probe Set ID | Expression ratio Th17/Th1 | Th17/Th2 | Th17/Treg |
|---|---|---|---|---|---|---|---|---|---|
| With activation stimulation | | | | | | | | | |
| Membrane | ADAM12 | 8038 | NP_003465, | NM_003474, | Hs.594537 | 202952_s_at | 19.5 | 71.0 | 3.5 |
| | | | NP_067673 | NM_021641 | | | | | |
| | AKAP12 | 9590 | NP_005091, | NM_005100, | Hs.371240 | 210517_s_at | 9.8 | 4.5 | 12.8 |
| | | | NP_653080 | NM_144497 | | 227529_s_at | 8.9 | 5.7 | 45.5 |
| | ANKS1B | 56899 | NP_064525, | NM_020140, | Hs.506458 | 227439_at | 5.7 | 10.5 | 15.1 |
| | | | NP_690001, | NM_152788, | | 227440_at | 3.6 | 12.0 | 6.3 |
| | | | NP_858056 | NM_181670 | | 240292_x_at | 5.1 | 9.9 | 8.5 |
| | ATP6V0A4 | 50617 | NP_065683, | NM_020632, | Hs.98967 | 220197_at | 9.0 | 96.4 | 64.8 |
| | | | NP_570855, | NM_130840, | | | | | |
| | | | NP_570856 | NM_130841 | | | | | |
| | ATP9A | 10079 | NP_006036 | NM_006045 | Hs.714307 | 212062_at | 7.5 | 55.4 | 46.4 |
| | BVES | 11149 | NP_009004, | NM_007073, | Hs.221660 | 228783_at | 3.4 | 5.9 | 9.8 |
| | | | NP_671488 | NM_147147 | | | | | |
| | C5orf40 | 408263 | NP_001001343 | NM_001001343 | Hs.437066 | 1554801_at | 17.2 | 21.0 | 5.4 |
| | C9orf125 | 84302 | NP_115718 | NM_032342 | Hs.655738 | 224458_at | 7.5 | 5.2 | 8.2 |
| | CDH4 | 1002 | NP_001785 | NM_001794 | Hs.473231 | 206866_at | 7.4 | 13.7 | 11.6 |
| | DIO2 | 1734 | NP_000784, | NM_000793, | Hs.202354 | 203699_s_at | 5.7 | 8.0 | 15.4 |
| | | | NP_001007024, | NM_001007023, | | 203700_s_at | 12.2 | 13.6 | 14.1 |
| | | | NP_054644 | NM_013989 | | 231240_at | 9.6 | 5.3 | 6.3 |
| | DMD | 1756 | NP_000100, | NM_000109, | Hs.495912 | 203881_s_at | 9.7 | 3.1 | 10.4 |
| | | | NP_003997, | NM_004006, | | | | | |
| | | | NP_003998, | NM_004007, | | | | | |
| | | | NP_004000, | NM_004009, | | | | | |
| | | | NP_004001, | NM_004010, | | | | | |
| | | | NP_004002, | NM_004011, | | | | | |
| | | | NP_004003, | NM_004012, | | | | | |
| | | | NP_004004, | NM_004013, | | | | | |
| | | | NP_004005, | NM_004014, | | | | | |
| | | | NP_004006, | NM_004015, | | | | | |
| | | | NP_004007, | NM_004016, | | | | | |
| | | | NP_004008, | NM_004017, | | | | | |
| | | | NP_004009, | NM_004018, | | | | | |
| | | | NP_004010, | NM_004019, | | | | | |
| | | | NP_004011, | NM_004020, | | | | | |
| | | | NP_004012, | NM_004021, | | | | | |
| | | | NP_004013, | NM_004022, | | | | | |
| | | | NP_004014 | NM_004023 | | | | | |
| | DPY19L2 | 283417 | NP_776173 | NM_173812 | Hs.533644 | 230158_at | 12.5 | 13.0 | 3.4 |
| | GPR34 | 2857 | NP_001091048, | NM_001097579 | Hs.495989 | 223620_at | 7.2 | 12.6 | 22.1 |
| | HRH4 | 59340 | NP_001137300, | NM_001143828, | Hs.287388 | 221170_at | 45.8 | 3.0 | 45.6 |
| | | | NP_067637 | NM_021624 | | | | | |
| | IL23R | 149233 | NP_653302 | NM_144701 | Hs.677426 | 1561853_a_at | 15.1 | 7.8 | 6.2 |
| | IRS2 | 8660 | NP_003740 | NM_003749 | Hs.442344 | 209185_s_at | 3.3 | 6.4 | 5.1 |
| | KCNE3 | 10008 | NP_005463 | NM_005472 | Hs.523899 | 227647_at | 14.9 | 5.0 | 3.7 |
| | L1CAM | 3897 | NP_000416, | NM_000425, | Hs.522818 | 204584_at | 10.3 | 6.6 | 5.9 |
| | | | NP_076493 | NM_024003 | | | | | |
| | MCAM | 4162 | NP_006491 | NM_006500 | Hs.599039 | 210869_s_at | 12.8 | 24.4 | 4.3 |
| | MFAP3L | 9848 | NP_001009554, | NM_001009554, | Hs.593942 | 205442_at | 25.8 | 22.6 | 10.5 |
| | | | NP_067679 | NM_021647 | | 210492_at | 3.5 | 4.7 | 6.7 |
| | MUC20 | 200958 | NP_001091986, | NM_001098516, | Hs.308992 | 231941_s_at | 8.3 | 3.4 | 7.2 |
| | | | NP_689886, | NM_152673, | | | | | |
| | | | XP_001726746 | XM_001726694 | | | | | |
| | MYO7A | 4647 | NP_000251, | NM_000260, | Hs.370421 | 208189_s_at | 13.7 | 13.0 | 6.8 |
| | | | NP_001120651, | NM_001127179, | | 211103_at | 7.5 | 15.1 | 5.1 |
| | | | NP_001120652 | NM_001127180 | | | | | |
| | POPDC3 | 64208 | NP_071756 | NM_022361, | Hs.458336 | 219926_at | 4.5 | 12.9 | 12.8 |
| | | | | NR_024539 | | | | | |
| | PTPRM | 5797 | NP_001098714, | NM_001105244, | Hs.49774 | 1555579_s_at | 4.1 | 66.0 | 4.1 |
| | | | NP_002836 | NM_002845 | | | | | |
| | SHROOM2 | 357 | NP_001640 | NM_001649 | Hs.567236 | 204967_at | 11.5 | 3.5 | 5.9 |
| | SLC16A4 | 9122 | NP_004687 | NM_004696 | Hs.351306 | 205234_at | 29.8 | 16.6 | 6.8 |
| | SLCO2B1 | 11309 | NP_009187 | NM_007256 | Hs.7884 | 203473_at | 11.0 | 5.9 | 5.9 |
| | SORBS1 | 10580 | NP_001030126, | NM_001034954, | Hs.713556 | 218087_s_at | 37.9 | 4.7 | 12.8 |
| | | | NP_001030127, | NM_001034955, | | 222513_s_at | 14.4 | 3.6 | 8.2 |
| | | | NP_001030128, | NM_001034956, | | | | | |
| | | | NP_001030129, | NM_001034957, | | | | | |
| | | | NP_006425, | NM_006434, | | | | | |
| | | | NP_056200, | NM_015385, | | | | | |
| | | | NP_079267 | NM_024991 | | | | | |
| | TANC1 | 85461 | NP_203752 | NM_033394 | Hs.61590 | 225308_s_at | 8.1 | 17.7 | 4.9 |
| | TANC2 | 26115 | NP_079461 | NM_025185 | Hs.410889 | 224952_at | 5.3 | 4.9 | 6.4 |
| | TJP1 | 7082 | NP_003248, | NM_003257, | Hs.716406 | 202011_at | 11.5 | 11.7 | 5.6 |
| | | | NP_783297 | NM_175610 | | | | | |

TABLE 7-continued

| Location of encoded protein | Gene symbol | Entrez Gene ID | Protein ID | Transcript ID | UniGene ID | Probe Set ID | Expression ratio Th17/Th1 | Th17/Th2 | Th17/Treg |
|---|---|---|---|---|---|---|---|---|---|
| | TMEM163 | 81615 | NP_112185 | NM_030923 | Hs.369471 | 1552626_a_at | 10.8 | 12.6 | 13.9 |
| | | | | | | 223503_at | 18.5 | 23.9 | 21.7 |
| | TMEM44 | 93109 | NP_001011655, NP_612408 | NM_001011655, NM_138399 | Hs.478729 | 228054_at | 7.4 | 5.2 | 3.3 |
| | TNS3 | 64759 | NP_073585 | NM_022748 | Hs.520814 | 217853_at | 7.8 | 27.1 | 6.4 |
| | UNC13C | 440279 | NP_001074003 | NM_001080534 | Hs.657273 | 1556095_at | 7.3 | 6.1 | 3.8 |
| | UPK1B | 7348 | NP_008883 | NM_006952 | Hs.271580 | 210065_s_at | 5.3 | 9.6 | 10.3 |
| | WDFY3 | 23001 | NP_055806, NP_848698, NP_848700 | NM_014991, NM_178583, NM_178585 | Hs.480116 | 212598_at | 10.7 | 16.1 | 19.6 |
| | | | | | | 212602_at | 8.5 | 19.4 | 9.8 |
| | | | | | | 212606_at | 22.6 | 62.2 | 20.5 |
| Extracellular/secreted | CXCL13 | 10563 | NP_006410 | NM_006419 | Hs.100431 | 205242_at | 47.5 | 40.4 | 4.8 |
| | IL17A | 3605 | NP_002181 | NM_002190 | Hs.41724 | 208402_at | 16.5 | 11.1 | 3.2 |
| | | | | | | 216876_s_at | 404.7 | 50.0 | 7.6 |
| | IL17F | 112744 | NP_443104 | NM_052872 | Hs.272295 | 234408_at | 464.4 | 421.4 | 77.1 |
| | IL22 | 50616 | NP_065386 | NM_020525 | Hs.287369 | 221165_s_at | 4.7 | 4.6 | 4.3 |
| | | | | | | 222974_at | 4.3 | 5.5 | 9.8 |
| | IL26 | 55801 | NP_060872 | NM_018402 | Hs.272350 | 221111_at | 10.2 | 22.5 | 67.8 |
| | IL9 | 3578 | NP_000581 | NM_000590 | Hs.960 | 208193_at | 729.7 | 174.0 | 35.8 |
| | PCOLCE2 | 26577 | NP_037495 | NM_013363 | Hs.8944 | 219295_s_at | 10.8 | 19.3 | 6.2 |
| | PNOC | 5368 | NP_006219 | NM_006228 | Hs.88218 | 205901_at | 39.4 | 11.4 | 24.3 |
| | SMPDL3A | 10924 | NP_006705 | NM_006714 | Hs.486357 | 213624_at | 3.4 | 3.3 | 3.5 |
| | TGFBI | 7045 | NP_000349 | NM_000358 | Hs.369397 | 201506_at | 55.9 | 318.3 | 32.0 |
| Intracellular | BCAT1 | 586 | NP_005495 | NM_005504 | Hs.438993 | 214452_at | 3.1 | 5.8 | 28.9 |
| | BHLHE22 | 27319 | NP_689627 | NM_152414 | Hs.591870 | 228636_at | 11.6 | 14.2 | 18.7 |
| | C13orf18, LOC728970 | 80183, 728970 | NP_079389, XP_001132115, XP_001133896, XP_001720207 | NM_025113, XM_001132115, XM_001133896, XM_001720155 | Hs.98117 | 44790_s_at | 3.2 | 18.8 | 12.4 |
| | CA2 | 760 | NP_000058 | NM_000067 | Hs.155097 | 209301_at | 5.2 | 61.3 | 167.6 |
| | CCDC3 | 83643 | NP_113643 | NM_031455 | Hs.498720 | 223316_at | 11.2 | 52.3 | 43.4 |
| | CDS1 | 1040 | NP_001254 | NM_001263 | Hs.654899 | 205709_s_at | 7.3 | 9.5 | 4.2 |
| | | | | | | 226185_at | 4.2 | 7.8 | 3.3 |
| | CHN1 | 1123 | NP_001020372, NP_001813 | NM_001025201, NM_001822 | Hs.654534 | 212624_s_at | 11.5 | 21.3 | 9.1 |
| | CLIC5, LOC100131610 | 53405, 100131610 | NP_001107558, NP_058625, XP_001723610 | NM_001114086, NM_016929, XM_001723558 | Hs.485489 | 213317_at | 7.1 | 22.1 | 9.6 |
| | | | | | | 217628_at | 3.1 | 4.2 | 4.6 |
| | | | | | | 243917_at | 10.8 | 17.2 | 11.7 |
| | | | | | | 219866_at | 6.2 | 10.6 | 12.2 |
| | CTSH | 1512 | NP_004381, NP_683880 | NM_004390, NM_148979 | Hs.148641 | 202295_s_at | 4.6 | 12.1 | 6.9 |
| | CYP7B1 | 9420 | NP_004811 | NM_004820 | Hs.667720 | 207386_at | 16.4 | 11.8 | 5.3 |
| | DAPK2 | 23604 | NP_055141 | NM_014326 | Hs.237886 | 206324_s_at | 4.4 | 4.7 | 3.9 |
| | DMRT1 | 1761 | NP_068770 | NM_021951 | Hs.98586 | 220493_at | 5.2 | 18.4 | 3.9 |
| | DSE | 29940 | NP_001074445, NP_037484 | NM_001080976, NM_013352 | Hs.486292 | 218854_at | 15.0 | 51.2 | 22.3 |
| | EML1 | 2009 | NP_001008707, NP_004425 | NM_001008707, NM_004434 | Hs.12451 | 204796_at | 10.1 | 8.9 | 5.8 |
| | | | | | | 204797_s_at | 3.1 | 3.1 | 3.2 |
| | FBXL17 | 64839 | NP_073735 | NM_022824 | Hs.657225 | 227203_at | 12.6 | 11.8 | 4.5 |
| | FBXL21 | 26223 | NP_036291 | NM_012159 | Hs.591275 | 1555412_at | 26.5 | 35.3 | 22.3 |
| | FHOD3 | 80206 | NP_079411 | NM_025135 | Hs.436636 | 218980_at | 7.0 | 9.9 | 6.7 |
| | H2AFY2 | 55506 | NP_061119 | NM_018649 | Hs.499953 | 218445_at | 3.9 | 8.2 | 4.7 |
| | HIST1H2BC | 8347 | NP_003517 | NM_003526 | Hs.658713 | 236193_at | 3.8 | 4.4 | 3.3 |
| | HLX | 3142 | NP_068777 | NM_021958 | Hs.74870 | 214438_at | 3.3 | 5.2 | 39.3 |
| | IRAK3 | 11213 | NP_001135995, NP_009130 | NM_001142523, NM_007199 | Hs.369265 | 213817_at | 9.4 | 18.8 | 6.5 |
| | MACC1 | 346389 | NP_877439 | NM_182762 | Hs.598388 | 1566764_at | 5.6 | 12.8 | 3.5 |
| | | | | | | 1566766_a_at | 9.2 | 17.3 | 4.7 |
| | MAML3 | 55534 | NP_061187 | NM_018717 | Hs.586165 | 242794_at | 6.4 | 5.7 | 4.6 |
| | MAP3K4 | 4216 | NP_005913, NP_006715 | NM_005922, NM_006724 | Hs.390428 | 204089_x_at | 3.3 | 3.3 | 3.4 |
| | | | | | | 216199_s_at | 3.2 | 3.6 | 3.4 |
| | MYO10 | 4651 | NP_036466 | NM_012334 | Hs.481720 | 1554026_a_at | 9.1 | 11.7 | 7.1 |
| | | | | | | 201976_s_at | 45.4 | 19.1 | 15.0 |
| | | | | | | 216222_s_at | 3.0 | 6.2 | 6.7 |
| | OTUB2 | 78990 | NP_075601 | NM_023112 | Hs.278815 | 219369_s_at | 3.1 | 3.4 | 3.8 |
| | | | | | | 222878_s_at | 4.2 | 7.2 | 4.8 |
| | PAPSS2 | 9060 | NP_001015880, NP_004661 | NM_001015880, NM_004670 | Hs.524491 | 203058_s_at | 5.5 | 11.0 | 11.1 |
| | | | | | | 203060_s_at | 6.3 | 47.2 | 17.3 |
| | PCBP3 | 54039 | NP_001123613, NP_065389 | NM_001130141, NM_020528 | Hs.474049 | 230486_at | 4.5 | 3.1 | 5.0 |
| | PDE4DIP | 9659 | NP_001002810, NP_001002811, NP_001002812, NP_055459, NP_071754 | NM_001002810, NM_001002811, NM_001002812, NM_014644, NM_022359 | Hs.654651 | 205872_x_at | 5.2 | 33.6 | 4.3 |
| | | | | | Hs.613082 | 209700_x_at | 4.9 | 29.1 | 8.3 |
| | PDK4 | 5166 | NP_002603 | NM_002612 | Hs.8364 | 225207_at | 5.3 | 3.0 | 4.1 |

TABLE 7-continued

| Location of encoded protein | Gene symbol | Entrez Gene ID | Protein ID | Transcript ID | UniGene ID | Probe Set ID | Expression ratio Th17/Th1 | Th17/Th2 | Th17/Treg |
|---|---|---|---|---|---|---|---|---|---|
| | PLD1 | 5337 | NP_001123553, NP_002653 | NM_001130081, NM_002662 | Hs.382865 | 226636_at | 3.7 | 3.2 | 8.2 |
| | PPARG | 5468 | NP_005028, NP_056953, NP_619725, NP_619726 | NM_005037, NM_015869, NM_138711, NM_138712 | Hs.162646 | 208510_s_at | 8.0 | 22.8 | 14.1 |
| | PTPN13 | 5783 | NP_006255, NP_542414, NP_542415, NP_542416 | NM_006264, NM_080683, NM_080684, NM_080685 | Hs.436142 | 204201_s_at<br>243792_x_at | 3.1<br>7.9 | 4.5<br>5.5 | 19.7<br>11.7 |
| | RGS18 | 64407 | NP_570138 | NM_130782 | Hs.440890 | 223809_at | 4.1 | 4.9 | 3.4 |
| | RGS2 | 5997 | NP_002914 | NM_002923 | Hs.78944 | 202388_at | 3.3 | 3.5 | 8.1 |
| | RGS20 | 8601 | NP_003693, NP_733466 | NM_003702, NM_170587 | Hs.368733 | 210138_at | 6.4 | 4.9 | 9.7 |
| | RORC | 6097 | NP_001001523, NP_005051 | NM_001001523, NM_005060 | Hs.256022 | 228806_at | 150.1 | 51.2 | 5.7 |
| | SIM1 | 6492 | NP_005059 | NM_005068 | Hs.520293 | 1556300_s_at<br>206876_at | 14.5<br>10.9 | 5.8<br>5.2 | 99.6<br>26.9 |
| | SNAI2 | 6591 | NP_003059 | NM_003068 | Hs.360174 | 213139_at | 8.2 | 15.0 | 6.8 |
| | SOX2 | 6657 | NP_003097 | NM_003106 | Hs.518438 | 228038_at | 14.4 | 14.4 | 16.4 |
| | SPIRE1 | 56907 | NP_001122098, NP_001122099, NP_064533 | NM_001128626, NM_001128627, NM_020148 | Hs.515283 | 1554807_a_at<br>224995_at<br>225018_at | 6.0<br>7.2<br>5.5 | 3.3<br>5.2<br>5.4 | 4.4<br>5.9<br>7.8 |
| | TBC1D12 | 23232 | NP_056003 | NM_015188 | Hs.500598 | 221858_at | 4.2 | 3.2 | 3.1 |
| | TGM5 | 9333 | NP_004236, NP_963925 | NM_004245, NM_201631 | Hs.129719 | 207911_s_at | 5.1 | 7.7 | 6.5 |
| | TMOD1 | 7111 | NP_003266 | NM_003275 | Hs.494595 | 203661_s_at<br>203662_s_at | 6.2<br>6.2 | 10.7<br>9.5 | 4.0<br>3.7 |
| | TUBB6 | 84617 | NP_115914 | NM_032525 | Hs.193491 | 209191_at | 3.5 | 11.2 | 6.4 |
| Unknown | C12orf64 | 283310 | NP_775862 | NM_173591 | Hs.355145 | 1553746_a_at | 4.2 | 5.3 | 10.8 |
| | C6orf168 | 84553 | NP_115900 | NM_032511 | Hs.573245 | 232067_at | 3.3 | 5.8 | 37.1 |
| | CAMSAP1L1 | 23271 | NP_982284 | NM_203459 | Hs.23585 | 217196_s_at | 22.5 | 10.1 | 3.7 |
| | MAGED4, MAGED4B | 728239, 81557 | NP_001092270, NP_110428, NP_803879, NP_803881 | NM_001098800, NM_030801, NM_177535, NM_177537 | Hs.571729 | 223313_s_at | 16.3 | 8.6 | 3.5 |
| | — | — | — | AK093612 | Hs.663643 | 1556602_at | 4.1 | 5.9 | 6.3 |
| | — | — | — | BC010059 | Hs.637648 | 1562957_at | 6.6 | 3.6 | 4.6 |
| | — | — | — | AK055628, uc001ljj.1 | Hs.594351 | 226777_at | 30.4 | 42.8 | 3.4 |
| | — | — | — | GENSCAN00000030683 | — | 227985_at | 13.4 | 19.2 | 3.6 |
| | — | — | — | AA416573, AA628762, D53835, D53836, H24473, R37871, R40232, T10348, T23451, W56351, W57867, Z28733 | Hs.654918 | 229951_x_at | 4.2 | 13.5 | 4.9 |
| | — | — | — | AK027107 | Hs.655798 | 232331_at | 3.5 | 3.5 | 9.0 |
| | — | — | — | AI269134, AI312873, AI671475, AV656012, AW162011, BG151392, H69527, N43169, Z36958 | Hs.657330 | 235438_at | 73.9 | 22.0 | 3.3 |
| | — | — | — | AA687415, AA96901, AI291640, AI446064, AI634557, AI694948, AI701854, AI983938, AV745212, AV745909, AV746001, AW008696, | Hs.434948 | 238009_at | 4.6 | 15.9 | 15.0 |

TABLE 7-continued

| Location of encoded protein | Gene symbol | Entrez Gene ID | Protein ID | Transcript ID | UniGene ID | Probe Set ID | Expression ratio Th17/Th1 | Th17/Th2 | Th17/Treg |
|---|---|---|---|---|---|---|---|---|---|
| | | | | AW511701, AW974416, BG149302, BG150103, N66771, R66991 | | | | | |
| | — | — | — | AI148241, AI735444, BE645654, BF510855, BF511636 | Hs.659083 | 238151_at | 37.6 | 48.1 | 29.9 |
| | — | — | — | AK094629 | Hs.594896 | 238623_at | 7.0 | 5.6 | 6.8 |
| | — | — | — | AI435469, BF111679, BF112253, R37814 | Hs.656932 | 241022_at | 6.1 | 10.7 | 12.4 |
| | — | — | — | AA846423, AI022103, BF061333 | Hs.665895 | 243922_at | 16.7 | 12.8 | 6.0 |
| | — | — | — | AA648972, AA879467, AI802768, AW974600 | Hs.602350 | 244247_at | 3.9 | 3.4 | 5.3 |

Among the above genes, those shown in Table 8 have been known for their specific expression in Th17 cells.

TABLE 8

| SEQ ID NO: | Gene symbol (Gene title) | Entrez Gene ID | Protein ID | Transcript ID | UniGene ID | Probe Set ID | Expression ratio Th17/Th1 | Th17/Th2 | Th17/Treg |
|---|---|---|---|---|---|---|---|---|---|
| 175 | IL23R(interleukin 23 receptor) | 149233 | NP_653302 | NM_144701 | Hs.677426 | 1552912_a_at | 7.6 | 11.7 | 4.5 |
| 176 | IL17A(interleukin 17A) | 3605 | NP_002181 | NM_002190 | Hs.41724 | 216876_s_at | 397.5 | 473.0 | 29.3 |
| 177 | IL17F(interleukin 17F) | 112744 | NP_443104 | NM_052872 | Hs.272295 | 234408_at | 611.6 | 951.0 | 383.6 |
| 178 | IL22(interleukin 22) | 50616 | NP_065386 | NM_020525 | Hs.287369 | 222974_at | 6.4 | 29.9 | 10.6 |
| 179 | IL26(interleukin 26) | 55801 | NP_060872 | NM_018402 | Hs.272350 | 221111_at | 10.1 | 13.0 | 39.4 |
| 180 | RORC(RAR-related orphan receptor C) | 6097 | NP_001001523, NP_005051 | NM_001001523, NM_005060 | Hs.256022 | 228806_at | 13.8 | 174.9 | 7.6 |

Expression levels of those known genes in Th1, Th2, Treg and Th17 cells obtained in the above step 2. were analyzed with microarray as described above. It was found that those genes were expressed 4 to 950 times higher in Th17 cells than in Th1, Th2 and Treg cells. These results are shown in FIG. 1. These results indicated that the above cells are suitable for investigation of markers for detecting Th17 cells.

The present inventors have identified novel polynucleotide markers for detecting Th17 cells by excluding the genes shown in Table 8 from those obtained as above. These novel polynucleotide markers are shown in Table 9.

In this table, "Condition" means with or without activation stimulation of cells. The genes designated as "Common" in the column of "Condition" are the genes specifically expressed in both Th17 cells with stimulation and without stimulation. The genes designated as "With stimulation" and "Without stimulation" are the genes specifically expressed either in Th17 cells with stimulation or without stimulation, respectively.

TABLE 9

| Location of encoded protein | Condition | No. | Gene symbol | Entrez Gene ID | Protein ID | Transcript ID | UniGene ID | Probe Set ID | SEQ ID NO: |
|---|---|---|---|---|---|---|---|---|---|
| Membrane | Common | 1 | ADAM12 | 8038 | NP_003465, NP_067673 | NM_003474, NM_021641 | Hs.594537 | 202952_s_at | 1 |
| | | 2 | ANKS1B | 56899 | NP_064525, NP_690001, NP_858056 | NM_020140, NM_152788, NM_181670 | Hs.506458 | 227439_at<br>240292_x_at | 2<br>3 |
| | | 3 | ATP6V0A4 | 50617 | NP_065683, NP_570855, NP_570856 | NM_020632, NM_130840, NM_130841 | Hs.98967 | 220197_at | 4 |
| | | 4 | ATP9A | 10079 | NP_006036 | NM_006045 | Hs.714307 | 212062_at | 5 |

TABLE 9-continued

| Location of encoded protein | Condition | No. | Gene symbol | Entrez Gene ID | Protein ID | Transcript ID | UniGene ID | Probe Set ID | SEQ ID NO: |
|---|---|---|---|---|---|---|---|---|---|
| | | 5 | BVES | 11149 | NP_009004,<br>NP_671488 | NM_007073,<br>NM_147147 | Hs.221660 | 228783_at | 6 |
| | | 6 | C5orf40 | 408263 | NP_001001343 | NM_001001343 | Hs.437066 | 1554801_at | 7 |
| | | 7 | CDH4 | 1002 | NP_001785 | NM_001794 | Hs.473231 | 206866_at | 8 |
| | | 8 | DIO2 | 1734 | NP_000784,<br>NP_001007024,<br>NP_054644 | NM_000793,<br>NM_001007023,<br>NM_013989 | Hs.202354 | 203700_s_at | 9 |
| | | 9 | DMD | 1756 | NP_000100,<br>NP_003997,<br>NP_003998,<br>NP_004000,<br>NP_004001,<br>NP_004002,<br>NP_004003,<br>NP_004004,<br>NP_004005,<br>NP_004006,<br>NP_004007,<br>NP_004008,<br>NP_004009,<br>NP_004010,<br>NP_004011,<br>NP_004012,<br>NP_004013,<br>NP_004014 | NM_000109,<br>NM_004006,<br>NM_004007,<br>NM_004009,<br>NM_004010,<br>NM_004011,<br>NM_004012,<br>NM_004013,<br>NM_004014,<br>NM_004015,<br>NM_004016,<br>NM_004017,<br>NM_004018,<br>NM_004019,<br>NM_004020,<br>NM_004021,<br>NM_004022,<br>NM_004023 | Hs.495912 | 203881_s_at | 10 |
| | | 10 | GPR34 | 2857 | NP_001091048,<br>NP_005291 | NM_001097579,<br>NM_005300 | Hs.495989 | 223620_at | 11 |
| | | 11 | IRS2 | 8660 | NP_003740 | NM_003749 | Hs.442344 | 209184_s_at<br>209185_s_at | 12<br>13 |
| | | 12 | KCNE3 | 10008 | NP_005463 | NM_005472 | Hs.523899 | 227647_at | 14 |
| | | 13 | L1CAM | 3897 | NP_000416,<br>NP_076493 | NM_000425,<br>NM_024003 | Hs.522818 | 204584_at | 15 |
| | | 14 | MCAM | 4162 | NP_006491 | NM_006500 | Hs.599039 | 210869_s_at | 16 |
| | | 15 | MFAP3L | 9848 | NP_001009554,<br>NP_067679 | NM_001009554,<br>NM_021647 | Hs.593942 | 205442_at | 17 |
| | | 16 | MYO7A | 4647 | NP_000251,<br>NP_001120651,<br>NP_001120652 | NM_00260,<br>NM_001127179,<br>NM_001127180 | Hs.370421 | 208189_s_at | 18 |
| | | 17 | PTPRM | 5797 | NP_001098714,<br>NP_002836 | NM_001105244,<br>NM_002845 | Hs.49774 | 1555579_s_at | 19 |
| | | 18 | SHROOM2 | 357 | NP_001640 | NM_001649 | Hs.567236 | 204967_at | 20 |
| | | 19 | SLC16A4 | 9122 | NP_004687 | NM_004696 | Hs.351306 | 205234_at | 21 |
| | | 20 | SLCO2B1 | 11309 | NP_009187 | NM_007256 | Hs.7884 | 203473_at | 22 |
| | | 21 | TANC2 | 26115 | NP_079461 | NM_025185 | Hs.410889 | 208425_s_at<br>224952_at | 23<br>24 |
| | | 22 | TJP1 | 7082 | NP_003248,<br>NP_783297 | NM_003257,<br>NM_175610 | Hs.716406 | 202011_at | 25 |
| | | 23 | TMEM163 | 81615 | NP_112185 | NM_030923 | Hs.369471 | 1552626_a_at<br>223503_at | 26<br>27 |
| | | 24 | TNS3 | 64759 | NP_073585 | NM_022748 | Hs.520814 | 217853_at | 28 |
| | | 25 | UPK1B | 7348 | NP_008883 | NM_006952 | Hs.271580 | 210065_s_at | 29 |
| | | 26 | WDFY3 | 23001 | NP_055806,<br>NP_848698,<br>NP_848700 | NM_014991,<br>NM_178583,<br>NM_178585 | Hs.480116 | 212598_at<br>212602_at<br>212606_at | 30<br>31<br>32 |
| | w/o stimulation | 27 | DRD2 | 1813 | NP_000786,<br>NP_057658 | NM_000795,<br>NM_016574 | Hs.73893 | 216938_x_at | 33 |
| | | 28 | GJC1 | 10052 | NP_001073852,<br>NP_005488 | NM_001080383,<br>NM_005497 | Hs.532593 | 228776_at<br>243502_at | 34<br>35 |
| | Without stimulation | 29 | PGBD5,<br>LOC100134440 | 79605,<br>100134440 | NP_078830,<br>XP_001716155 | NM_024554,<br>XM_001716103 | Hs.520463 | 219225_at | 36 |
| | | 30 | MS4A7 | 58475 | NP_067024,<br>NP_996821,<br>NP_996822,<br>NP_996823 | NM_021201,<br>NM_206938,<br>NM_206939,<br>NM_206940 | Hs.530735 | 223343_at | 37 |
| | | 31 | ODZ4 | 26011 | NP_001092286 | NM_001098816 | Hs.213087 | 213273_at | 38 |
| | | 32 | PHKA1 | 5255 | NP_001116142,<br>NP_002628 | NM_001122670,<br>NM_002637 | Hs.201379 | 229876_at | 39 |
| | | 33 | RGS1 | 5996 | NP_002913 | NM_002922 | Hs.75256 | 202988_s_at | 40 |
| | | 34 | SHB | 6461 | NP_003019 | NM_003028 | Hs.521482 | 1557458_s_at | 41 |
| | | 35 | SLC44A3 | 126969 | NP_001107578,<br>NP_689582 | NM_001114106,<br>NM_152369 | Hs.483423 | 228221_at | 42 |
| | | 36 | SLC6A15 | 55117 | NP_060527,<br>NP_877499 | NM_018057,<br>NM_182767 | Hs.44424 | 206376_at | 43 |
| | | 37 | SYNGR3 | 9143 | NP_004200 | NM_004209 | Hs.435277 | 205691_at | 44 |

TABLE 9-continued

| Location of encoded protein | Condition | No. | Gene symbol | Entrez Gene ID | Protein ID | Transcript ID | UniGene ID | Probe Set ID | SEQ ID NO: |
|---|---|---|---|---|---|---|---|---|---|
| | With stimulation | 38 | AKAP12 | 9590 | NP_005091,<br>NP_653080 | NM_005100,<br>NM_144497 | Hs.371240 | 210517_s_at<br>227529_s_at | 45<br>46 |
| | | 39 | C9orf125 | 84302 | NP_115718 | NM_032342 | Hs.655738 | 224458_at | 47 |
| | | 40 | DPY19L2 | 283417 | NP_776173 | NM_173812 | Hs.533644 | 230158_at | 48 |
| | | 41 | HRH4 | 59340 | NP_001137300,<br>NP_067637 | NM_001143828,<br>NM_021624 | Hs.287388 | 221170_at | 49 |
| | | 42 | MUC20 | 200958 | NP_001091986,<br>NP_689886,<br>XP_001726746 | NM_001098516,<br>NM_152673,<br>XM_001726694 | Hs.308992 | 231941_s_at | 50 |
| | | 43 | POPDC3 | 64208 | NP_071756 | NM_022361,<br>NR_024539 | Hs.458336 | 219926_at | 51 |
| | | 44 | SORBS1 | 10580 | NP_001030126,<br>NP_001030127,<br>NP_001030128,<br>NP_001030129,<br>NP_006425,<br>NP_056200,<br>NP_079267 | NM_001034954,<br>NM_001034955,<br>NM_001034956,<br>NM_001034957,<br>NM_006434,<br>NM_015385,<br>NM_024991 | Hs.713556 | 218087_s_at<br>222513_s_at | 52<br>53 |
| | | 45 | TANC1 | 85461 | NP_203752 | NM_033394 | Hs.61590 | 225308_s_at | 54 |
| | | 46 | TMEM44 | 93109 | NP_001011655,<br>NP_612408 | NM_001011655,<br>NM_138399 | Hs.478729 | 228054_at | 55 |
| | | 47 | UNC13C | 440279 | NP_001074003 | NM_001080534 | Hs.657273 | 1556095_at | 56 |
| Extra-cellular/ secreted | Common | 48 | CXCL13 | 10563 | NP_006410 | NM_006419 | Hs.100431 | 205242_at | 57 |
| | | 49 | IL9 | 3578 | NP_000581 | NM_000590 | Hs.960 | 208193_at | 58 |
| | | 50 | PCOLCE2 | 26577 | NP_037495 | NM_013363 | Hs.8944 | 219295_s_at | 59 |
| | | 51 | PNOC | 5368 | NP_006219 | NM_006228 | Hs.88218 | 205901_at | 60 |
| | | 52 | SMPDL3A | 10924 | NP_006705 | NM_006714 | Hs.486357 | 213624_at | 61 |
| | | 53 | TGFBI | 7045 | NP_000349 | NM_000358 | Hs.369397 | 201506_at | 62 |
| | w/o stimulation | 54 | C17orf99 | 100141515 | NP_001156547 | NM_001163075 | Hs.633034 | 236981_at | 63 |
| | | 55 | EBI3 | 10148 | NP_005746 | NM_005755 | Hs.501452 | 219424_at | 64 |
| | | 56 | IL1A | 3552 | NP_000566 | NM_000575 | Hs.1722 | 210118_s_at | 65 |
| | | 57 | WNT3 | 7473 | NP_110380 | NM_030753 | Hs.445884 | 229103_at | 66 |
| Intracellular | Common | 58 | BCAT1 | 586 | NP_005495 | NM_005504 | Hs.438993 | 214390_s_at<br>214452_at<br>225285_at<br>226517_at | 67<br>68<br>69<br>70 |
| | | 59 | BHLHE22 | 27319 | NP_689627 | NM_152414 | Hs.591870 | 228636_at | 71 |
| | | 60 | C13orf18,<br>LOC728970 | 80183,<br>728970 | NP_079389,<br>XP_001132115,<br>XP_001133896,<br>XP_001720207 | NM_025113,<br>XM_001132115,<br>XM_001133896,<br>XM_001720155 | Hs.98117 | 44790_s_at | 72 |
| | | 61 | CA2 | 760 | NP_000058 | NM_000067 | Hs.155097 | 209301_at | 73 |
| | | 62 | CCDC3 | 83643 | NP_113643 | NM_031455 | Hs.498720 | 223316_at | 74 |
| | | 63 | CDS1 | 1040 | NP_001254 | NM_001263 | Hs.654899 | 205709_s_at | 75 |
| | | 64 | CHN1 | 1123 | NP_001020372,<br>NP_001813 | NM_001025201,<br>NM_001822 | Hs.654534 | 212624_s_at | 76 |
| | | 65 | CLIC5,<br>LOC100131610 | 53405,<br>100131610 | NP_001107558,<br>NP_058625,<br>XP_001723610 | NM_001114086,<br>NM_016929,<br>XM_001723558 | Hs.485489 | 213317_at<br>217628_at<br>243917_at<br>219866_at | 77<br>78<br>79<br>80 |
| | | 66 | CTSH | 1512 | NP_004381,<br>NP_683880 | NM_004390,<br>NM_148979 | Hs.148641 | 202295_s_at | 81 |
| | | 67 | CYP7B1 | 9420 | NP_004811 | NM_004820 | Hs.667720 | 207386_at | 82 |
| | | 68 | DAPK2 | 23604 | NP_055141 | NM_014326 | Hs.237886 | 206324_s_at<br>215184_at | 83<br>84 |
| | | 69 | DMRT1 | 1761 | NP_068770 | NM_021951 | Hs.98586 | 220493_at | 85 |
| | | 70 | DSE | 29940 | NP_001074445,<br>NP_037484 | NM_001080976,<br>NM_013352 | Hs.486292 | 218854_at | 86 |
| | | 71 | FBXL17 | 64839 | NP_073735 | NM_022824 | Hs.657225 | 227203_at | 87 |
| | | 72 | FBXL21 | 26223 | NP_036291 | NM_012159 | Hs.591275 | 1555412_at | 88 |
| | | 73 | FHOD3 | 80206 | NP_079411 | NM_025135 | Hs.436636 | 218980_at | 89 |
| | | 74 | H2AFY2 | 55506 | NP_061119 | NM_018649 | Hs.499953 | 218445_at | 90 |
| | | 75 | HLX | 3142 | NP_068777 | NM_021958 | Hs.74870 | 214438_at | 91 |
| | | 76 | IRAK3 | 11213 | NP_001135995,<br>NP_009130 | NM_001142523,<br>NM_007199 | Hs.369265 | 213817_at<br>220034_at | 92<br>93 |
| | | 77 | MACC1 | 346389 | NP_877439 | NM_182762 | Hs.598388 | 1566766_a_at | 94 |
| | | 78 | MAML3 | 55534 | NP_061187 | NM_018717 | Hs.586165 | 242794_at | 95 |
| | | 79 | MYO10 | 4651 | NP_036466 | NM_012334 | Hs.481720 | 201976_s_at | 96 |
| | | 80 | OTUB2 | 78990 | NP_075601 | NM_023112 | Hs.278815 | 219369_s_at<br>222878_s_at | 97<br>98 |
| | | 81 | PAPSS2 | 9060 | NP_001015880,<br>NP_004661 | NM_001015880,<br>NM_004670 | Hs.524491 | 203058_s_at<br>203060_s_at | 99<br>100 |
| | | 82 | PCBP3 | 54039 | NP_001123613,<br>NP_065389 | NM_001130141,<br>NM_020528 | Hs.474049 | 230486_at | 101 |

TABLE 9-continued

| Location of encoded protein | Condition | No. | Gene symbol | Entrez Gene ID | Protein ID | Transcript ID | UniGene ID | Probe Set ID | SEQ ID NO: |
|---|---|---|---|---|---|---|---|---|---|
| | | 83 | PDE4DIP | 9659 | NP_001002810,<br>NP_001002811,<br>NP_001002812,<br>NP_055459,<br>NP_071754 | NM_001002810,<br>NM_001002811,<br>NM_001002812,<br>NM_014644,<br>NM_022359 | Hs.654651<br>Hs.613082 | 205872_x_at<br>209700_x_at | 102<br>103 |
| | | 84 | PLD1 | 5337 | NP_001123553,<br>NP_002653 | NM_001130081,<br>NM_002662 | Hs.382865 | 177_at<br>215723_s_at<br>226636_at | 104<br>105<br>106 |
| | | 85 | PPARG | 5468 | NP_005028,<br>NP_056953,<br>NP_619725,<br>NP_619726 | NM_005037,<br>NM_015869,<br>NM_138711,<br>NM_138712 | Hs.162646 | 208510_s_at | 107 |
| | | 86 | PTPN13 | 5783 | NP_006255,<br>NP_542414,<br>NP_542415,<br>NP_542416 | NM_006264,<br>NM_080683,<br>NM_080684,<br>NM_080685 | Hs.436142 | 243792_x_at | 108 |
| | | 87 | RGS18 | 64407 | NP_570138 | NM_130782 | Hs.440890 | 223809_at | 109 |
| | | 88 | SIM1 | 6492 | NP_005059 | NM_005068 | Hs.520293 | 1556300_s_at<br>206876_at | 110<br>111 |
| | | 89 | SNAI2 | 6591 | NP_003059 | NM_003068 | Hs.360174 | 213139_at | 112 |
| | | 90 | SOX2 | 6657 | NP_003097 | NM_003106 | Hs.518438 | 228038_at | 113 |
| | | 91 | SPIRE1 | 56907 | NP_001122098,<br>NP_001122099,<br>NP_064533 | NM_001128626,<br>NM_001128627,<br>NM_020148 | Hs.515283 | 1554807_a_at<br>224995_at<br>225018_at | 114<br>115<br>116 |
| | | 92 | TBC1D12 | 23232 | NP_056003 | NM_015188 | Hs.500598 | 221858_at | 117 |
| | | 93 | TGM5 | 9333 | NP_004236,<br>NP_963925 | NM_004245,<br>NM_201631 | Hs.129719 | 207911_s_at | 118 |
| | | 94 | TMOD1 | 7111 | NP_003266 | NM_003275 | Hs.494595 | 203661_s_at<br>203662_s_at | 119<br>120 |
| | | 95 | TUBB6 | 84617 | NP_115914 | NM_032525 | Hs.193491 | 209191_at | 121 |
| | Without stimulation | 96 | DDIT4L | 115265 | NP_660287 | NM_145244 | Hs.480378 | 228057_at | 122 |
| | | 97 | DHRS9 | 10170 | NP_001135742,<br>NP_001135743,<br>NP_005762,<br>NP_954674 | NM_001142270,<br>NM_001142271,<br>NM_005771,<br>NM_199204 | Hs.179608 | 219799_s_at<br>223952_x_at<br>224009_x_at | 123<br>124<br>125 |
| | | 98 | ERC2 | 26059 | NP_056391 | NM_015576 | Hs.476389 | 213938_at | 126 |
| | | 99 | FERMT2 | 10979 | NP_001128471,<br>NP_001128472,<br>NP_006823 | NM_001134999,<br>NM_001135000,<br>NM_006832 | Hs.509343 | 209210_s_at | 127 |
| | | 100 | HHEX | 3087 | NP_002720 | NM_002729 | Hs.118651 | 204689_at | 128 |
| | | 101 | HS3ST1 | 9957 | NP_005105 | NM_005114 | Hs.507348 | 205466_s_at | 129 |
| | | 102 | NR5A2 | 2494 | NP_003813,<br>NP_995582 | NM_003822,<br>NM_205860 | Hs.33446 | 208343_s_at | 130 |
| | | 103 | PHLDA1 | 22822 | NP_031376 | NM_007350 | Hs.602085 | 217999_s_at<br>225842_at | 131<br>132 |
| | | 104 | RBM20 | 282996 | NP_001127835,<br>XP_001716171,<br>XP_291671,<br>XP_944430 | NM_001134363,<br>XM_001716119,<br>XM_291671,<br>XM_939337 | Hs.715766 | 238763_at | 133 |
| | | 105 | NINL | 22981 | NP_079452 | NM_025176 | Hs.696157 | 207705_s_at | 134 |
| | | 106 | RTN2 | 6253 | NP_005610,<br>NP_996783,<br>NP_996784 | NM_005619,<br>NM_206900,<br>NM_206901 | Hs.47517 | 34408_at | 135 |
| | | 107 | SH3RF2 | 153769 | NP_689763 | NM_152550 | Hs.443728 | 243582_at | 136 |
| | | 108 | TSHZ2 | 128553 | NP_775756 | NM_173485 | Hs.649877<br>Hs.271605 | 220213_at<br>243940_at | 137<br>138 |
| | With stimulation | 109 | EML1 | 2009 | NP_001008707,<br>NP_004425 | NM_001008707,<br>NM_004434 | Hs.12451 | 204796_at<br>204797_s_at | 139<br>140 |
| | | 110 | HIST1H2BC | 8347 | NP_003517 | NM_003526 | Hs.658713 | 236193_at | 141 |
| | | 111 | MAP3K4 | 4216 | NP_005913,<br>NP_006715 | NM_005922,<br>NM_006724 | Hs.390428 | 204089_x_at<br>216199_s_at | 142<br>143 |
| | | 112 | PDK4 | 5166 | NP_002603 | NM_002612 | Hs.8364 | 225207_at | 144 |
| | | 113 | RGS2 | 5997 | NP_002914 | NM_002923 | Hs.78944 | 202388_at | 145 |
| | | 114 | RGS20 | 8601 | NP_003693,<br>NP_733466 | NM_003702,<br>NM_170587 | Hs.368733 | 210138_at | 146 |
| Unknown | Common | 115 | — | — | — | AK055628,<br>uc001ljj.1 | Hs.594351 | 226777_at | 147 |
| | | 116 | — | — | — | AA416573,<br>AA628762,<br>D53835,<br>D53836,<br>H24473,<br>R37871,<br>R40232,<br>T10348,<br>T23451, | Hs.654918 | 229951_x_at | 148 |

TABLE 9-continued

| Location of encoded protein | Condition | No. | Gene symbol | Entrez Gene ID | Protein ID | Transcript ID | UniGene ID | Probe Set ID | SEQ ID NO: |
|---|---|---|---|---|---|---|---|---|---|
| | | | | | | W56351, W57867, Z28733 | | | |
| | | 117 | — | — | — | AA687415, AA96901, AI291640, AI446064, AI634557, AI694948, AI701854, AI983938, AV745212, AV745909, AV746001, AW008696, AW511701, AW974416, BG149302, BG150103, N66771, R66991 | Hs.434948 | 238009_at | 149 |
| | | 118 | — | — | — | AI148241, AI735444, BE645654, BF510855, BF511636 | Hs.659083 | 238151_at | 150 |
| | | 119 | — | — | — | AK094629 | Hs.594896 | 238623_at | 151 |
| | Without stimulation | 120 | C1orf106 | 55765 | NP_001136041, NP_060735 | NM_001142569, NM_018265 | Hs.518997 | 219010_at | 152 |
| | | 121 | C6orf145 | 221749 | NP_899229 | NM_183373 | Hs.484500 | 212923_s_at | 153 |
| | | 122 | LOC401097 | 401097 | XP_001717155, XP_001718614, XP_001718795 | XM_001717103, XM_001718562, XM_001718743 | Hs.710781 | 236738_at | 154 |
| | | 123 | MAMLD1 | 10046 | NP_005482 | NM_005491 | Hs.20136 | 205088_at | 155 |
| | | 124 | ZC3H12C | 85463 | NP_203748 | NM_033390 | Hs.376289 | 231899_at | 156 |
| | | 125 | — | — | — | AA579799, AA947186, AL049337, AW665328 | Hs.663788 | 215768_at | 157 |
| | | 126 | — | — | — | AK093229 | Hs.586723 | 222900_at | 158 |
| | | 127 | — | — | — | AK129763, CR595588, uc002jiy.1, uc002jiz.1 | Hs.157726 | 227452_at | 159 |
| | | 128 | — | — | — | AI766299 | — | 236338_at | 160 |
| | | 129 | — | — | — | AI262017, AI280978, AI284950, AI733224, AI733801 | Hs.666775 | 237923_at | 161 |
| | | 130 | — | — | — | AI682088, AI951058, F06296, F13164, T77624, Z44722 | Hs.606172 | 241726_at | 162 |
| | With stimulation | 131 | C12orf64 | 283310 | NP_775862 | NM_173591 | Hs.355145 | 1553746_a_at | 163 |
| | | 132 | C6orf168 | 84553 | NP_115900 | NM_032511 | Hs.573245 | 232067_at | 164 |
| | | 133 | CAMSAP1L1 | 23271 | NP_982284 | NM_203459 | Hs.23585 | 217196_s_at | 165 |
| | | 134 | MAGED4, MAGED4B | 728239, 81557 | NP_001092270, NP_110428, NP_803879, NP_803881 | NM_001098800, NM_030801, NM_177535, NM_177537 | Hs.571729 | 223313_s_at | 166 |
| | | 135 | — | — | — | AK093612 | Hs.663643 | 1556602_at | 167 |
| | | 136 | — | — | — | BC010059 | Hs.637648 | 1562957_at | 168 |
| | | 137 | — | — | — | GENSCAN00000030683 | — | 227985_at | 169 |
| | | 138 | — | — | — | AK027107 | Hs.655798 | 232331_at | 170 |
| | | 139 | — | — | — | AI269134, AI312873, AI671475, AV656012, AW162011, BG151392, H69527, N43169, Z36958 | Hs.657330 | 235438_at | 171 |

TABLE 9-continued

| Location of encoded protein | Condition | No. | Gene symbol | Entrez Gene ID | Protein ID | Transcript ID | UniGene ID | Probe Set ID | SEQ ID NO: |
|---|---|---|---|---|---|---|---|---|---|
| | | 140 | — | — | — | AI435469, BF111679, BF112253, R37814 | Hs.656932 | 241022_at | 172 |
| | | 141 | — | — | — | AA846423, AI022103, BF061333 | Hs.665895 | 243922_at | 173 |
| | | 142 | — | — | — | AA648972, AA879467, AI802768, AW974600 | Hs.602350 | 244247_at | 174 |

It is believed that detection of the polynucleotide markers shown in Table 9 by well-known methods in the art such as PCR or detection of proteins encoded by these polynucleotide markers by well-known methods in the art such as ELISA or flow cytometry allows specific detection of human Th17 cells.

EXAMPLE 2

Expression Analysis of Protein Markers for Detecting Human Th17 Cells

1. Preparation of Measurement Samples (1) Preparation of MCAM Measurement Samples To Th17 cells "without activation stimulation" ($5\times10^6$ cells/ml) prepared in Example 1 under the paragraph "2. Cell culture" was added a phycoerythrin (PE)-labeled anti-MCAM antibody (BioLegend) to a final concentration of 1.25 μg/ml and reaction was carried out at 4° C. for 20 minutes.

After the reaction, Th17 cells were washed by adding phosphate buffered saline (PBS) containing 0.5% BSA and centrifuging to collect the cells. The washed Th17 cells were suspended in PBS containing 0.5 μg/ml 7-amino-actinomycin D (7-AAD) and 0.5% BSA to prepare a MCAM measurement sample of Th17 cells ($5\times10^6$ cells/ml).

MCAM measurement samples of Th1 cells ($5\times10^6$ cells/ml), of Th2 cells ($5\times10^6$ cells/ml) and of Treg cells ($5\times10^6$ cells/ml) were prepared in the similar manner as above except that Th1, Th2 and Treg cells "without activation stimulation", respectively, were used instead of Th17 cells "without activation stimulation".

A negative control sample ($5\times10^6$ cells/ml) was prepared by adding a PE-labeled mouse IgG2a isotype control (BioLegend) to a final concentration of 1.0 μg/ml instead of the PE-labeled MCAM antibody and reacting at 4° C. for 20 minutes.

(2) Preparation of PTPRM Measurement Samples

To Th17 cells "without activation stimulation" ($5\times10^6$ cells/ml) prepared in Example 1 under the paragraph "2. Cell culture" was added an anti-PTPRM antibody (Abcam) to a final concentration of 2.0 μg/ml and reaction was carried out at 4° C. for 20 minutes.

After the reaction, Th17 cells were added with PBS containing 0.5% BSA and centrifuged to collect the cells. The collected Th17 cells were suspended in PBS containing 0.5% BSA. The suspension was added with a PE-labeled anti-mouse IgG antibody (BioLegend) to a final concentration of 1.0 μg/ml and reaction was carried out at 4° C. for 20 minutes.

After reaction with the PE-labeled anti-mouse IgG antibody, Th17 cells were washed by adding PBS containing 0.5% BSA and centrifuging to collect the cells. The washed Th17 cells were suspended in PBS containing 0.5 μg/ml 7-amino-actinomycin D (7-AAD) and 0.5% BSA to prepare a PTPRM measurement sample of Th17 cells ($5\times10^6$ cells/ml).

PTPRM measurement samples of Th1 cells ($5\times10^6$ cells/ml), of Th2 cells ($5\times10^6$ cells/ml) and of Treg cells ($5\times10^6$ cells/ml) were prepared in the similar manner as above except that Th1, Th2 and Treg cells "without activation stimulation", respectively, were used instead of Th17 cells "without activation stimulation".

A negative control sample ($5\times10^6$ cells/ml) was prepared by adding a mouse IgG2a isotype control (BioLegend) to a final concentration of 1.0 μg/ml instead of the anti-PTPRM antibody and reacting at 4° C. for 20 minutes.

(3) Preparation of CCR6 Measurement Samples

CCR6 measurement samples of Th17 cells ($5\times10^6$ cells/ml), of Th1 cells ($5\times10^6$ cells/ml), of Th2 cells ($5\times10^6$ cells/ml) and of Treg cells ($5\times10^6$ cells/ml) were prepared in the similar manner as the above paragraph "(1) Preparation of MCAM measurement samples" except that a PE-labeled anti-CCR6 antibody (BD Bioscience) was used at a final concentration of 1.0 μg/ml instead of the PE-labeled anti-MCAM antibody.

A negative control sample ($5\times10^6$ cells/ml) was prepared by adding a PE-labeled mouse IgG1 isotype control (BioLegend) to a final concentration of 1.0 μg/ml instead of the PE-labeled anti-CCR6 antibody and reacting at 4° C. for 20 minutes.

(4) Preparation of FOXP3 Measurement Samples

Th17 cells "without activation stimulation" ($5\times10^6$ cells/ml) prepared in Example 1 under the paragraph "2. Cell culture" were fixed and permeability of the cell membranes was increased using FOXP3 staining buffer set (eBioscience) before addition of a PE-labeled anti-FOXP3 antibody (BioLegend) to a final concentration of 3.125 μg/ml and reaction at 4° C. for 20 minutes.

After the reaction, Th17 cells were washed by adding phosphate buffered saline (PBS) containing 0.5% BSA and centrifuging to collect the cells. The washed Th17 cells were suspended in PBS containing 0.5% BSA to prepare a FOXP3 measurement sample of Th17 cells ($5\times10^6$ cells/ml).

FOXP3 measurement samples of Th1 cells ($5\times10^6$ cells/ml), of Th2 cells ($5\times10^6$ cells/ml) and of Treg cells ($5\times10^6$ cells/ml) were prepared in the similar manner as above except that Th1, Th2 and Treg cells "without activation stimulation", respectively, were used instead of Th17 cells "without activation stimulation".

A negative control sample ($5\times10^6$ cells/ml) was prepared by adding a PE-labeled mouse IgG1 isotype control (BioLegend) to a final concentration of 1.0 μg/ml instead of the PE-labeled FOXP3 antibody and reacting at 4° C. for 20 minutes.

(5) Preparation of GRP34 Measurement Samples

Th17 cells "without activation stimulation" prepared in Example 1 under the paragraph "2. Cell culture" were prepared in 5% FBS/RPMI at $2.5\times10^5$ cells/ml. Phorbol myristate acetate at a final concentration of 50 ng/ml and ionomycin at a final concentration of 1 μM were added and incubated at 37° C. for 4 hours to stimulate Th17 cells. Then, brefeldin A was added to a final concentration of 10 μg/ml and incubated at 37° C. for 2 hours.

After cultivation, Th17 cells were washed twice by adding phosphate buffered saline (PBS) containing 0.5% BSA and centrifuging to collect the cells. The washed Th17 cells were added with 2% paraformaldehyde to fix the cells. After fixing the cells, a saponin buffer (0.5% saponin, 0.5% bovine serum albumin (BSA), 1 mM sodium azide (in PBS)) was added to accelerate cell membrane permeability of Th17 cells.

The sample after saponin treatment was added with an anti-GPR34 antibody (Lifespan Biosciences) to a final concentration of 25.0 μg/ml and reaction was carried out at 4° C. for 20 minutes. After the reaction, the saponin buffer was added and Th17 cells were collected by centrifugation. The collected Th17 cells were suspended in the saponin buffer. The suspension was added with a PE-labeled anti-mouse IgG antibody (BioLegend) to a final concentration of 1.0 μg/ml and reaction was carried out at 4° C. for 20 minutes.

After the reaction with the PE-labeled anti-mouse IgG antibody, Th17 cells were washed twice by adding the saponin buffer and centrifuging to collect the cells. The washed Th17 cells were suspended in PBS containing 0.5% BSA to prepare a GRP34 measurement sample of Th17 cells ($2.5\times10^5$ cells/ml).

GRP34 measurement samples of Th1 cells, of Th2 cells and of Treg cells were prepared in the similar manner as above except that Th1, Th2 and Treg cells "without activation stimulation", respectively, were used instead of Th17 cells "without activation stimulation".

A negative control sample ($2.5\times10^6$ cells/ml) was prepared by adding a mouse IgG2a isotype control (BioLegend) to a final concentration of 1.0 μg/ml instead of the anti-GPR34 antibody and reacting at 4° C. for 20 minutes.

(6) Preparation of IL-17a Measurement Samples

Th17 cells "without activation stimulation" prepared in Example 1 under the paragraph "2. Cell culture" were prepared in 5% FBS/RPMI at $2.5\times10^5$ cells/ml. Phorbol myristate acetate at a final concentration of 50 ng/ml and ionomycin at a final concentration of 1 μM were added and incubated at 37° C. for 4 hours to stimulate Th17 cells. Then, brefeldin A was added to a final concentration of 10 μg/ml and incubated at 37° C. for 2 hours.

After cultivation, Th17 cells were washed by adding phosphate buffered saline (PBS) containing 0.5% BSA and centrifuging to collect the cells. The washed Th17 cells were added with 2% paraformaldehyde to fix the cells. After fixing the cells, a saponin buffer (0.5% saponin, 0.5% bovine serum albumin (BSA), 1 mM sodium azide (in PBS)) was added to accelerate cell membrane permeability of Th17 cells.

The sample after saponin treatment was added with a PerCP-Cy5.5-labeled anti-IL-17A antibody (eBioscience) to a final concentration of 0.15 μg/ml and reaction was carried out at 4° C. for 20 minutes.

After the reaction, Th17 cells were washed by adding the saponin buffer and centrifuging to collect cells. The washed Th17 cells were suspended in PBS containing 0.5% BSA to prepare a IL-17A measurement sample of Th17 cells ($2.5\times10^5$ cells/ml).

A negative control sample ($2.5\times10^6$ cells/ml) was prepared by adding a PerCP-Cy5.5-labeled mouse IgG1 isotype control (eBioscience) to a final concentration of 1.0 μg/ml instead of the PerCP-Cy5.5-labeled anti-IL-17A antibody.

(7) Preparation of IFN-γ Measurement Samples

IFN-γ measurement samples of Th17 cells ($2.5\times10^5$ cells/ml), of Th1 cells ($2.5\times10^5$ cells/ml), of Th2 cells ($2.5\times10^5$ cells/ml) and of Treg cells ($2.5\times10^5$ cells/ml) were prepared in the similar manner as the above paragraph "(6) Preparation of IL-17A measurement samples" except that an Alexa488-labeled anti-IFN-γ antibody (BioLegend) was used at a final concentration of 1.0 μg/ml instead of the PerCP-Cy5.5-labeled anti-IL-17A antibody.

A negative control sample ($2.5\times10^6$ cells/ml) was prepared by adding an Alex488-labeled mouse IgG 1 isotype control (BioLegend) to a final concentration of 1.0 μg/ml instead of the Alexa488-labeled anti-IFN-γ antibody and reacting at 4° C. for 20 minutes.

(8) Preparation of IL-4 Measurement Samples

IL-4 measurement samples of Th17 cells ($2.5\times10^5$ cells/ml), of Th1 cells ($2.5\times10^5$ cells/ml), of Th2 cells ($2.5\times10^5$ cells/ml) and of Treg cells ($2.5\times10^5$ cells/ml) were prepared in the similar manner as the above paragraph "(6) Preparation of IL-17A measurement samples" except that an APC-labeled anti-IL-4 antibody (eBioscience) was used at a final concentration of 0.2 μg/ml instead of the PerCP-Cy5.5-labeled anti-IL-17A antibody.

A negative control sample ($2.5\times10^6$ cells/ml) was prepared by adding an APC-labeled rat IgG1 isotype control (BioLegend) to a final concentration of 1.0 μg/ml instead of the APC-labeled anti-IL-4 antibody and reacting at 4° C. for 20 minutes.

2. Expression Analysis of Protein Markers in Measurement Samples Using Flow Cytometer The prepared measurement samples were analyzed by FACSCanto II (BD Bioscienct) and FACS DIVA software (BD Bioscience). Histograms (particle size distribution) of fluorescent intensities obtained by the analysis are shown in FIGS. 2 to 9, which correspond respectively to the histograms obtained from MCAM measurement samples, PTPRM measurement samples, GPR34 measurement samples, CCR6 measurement samples, IL-17A measurement samples, IFN-γ measurement samples, IL-4 measurement samples, and FOXP3 measurement samples. In FIGS. 2 to 9, the vertical axis of the histograms shows the number of cells and the horizontal axis shows the fluorescent intensity. The numbers at the upper right of the histograms correspond to the ratio (%) of positive cells for the marker gene relative to the number of total cells in the respective measurement samples. The cells were determined as positive or negative based on the maximal fluorescent intensity in the negative control. Namely, the cells having higher fluorescent intensity than the maximal fluorescent intensity of the negative control were determined as positive, while the cells having a fluorescent intensity equal to or lower than the maximal fluorescent intensity of the negative control were determined as negative. The ratio of positive cells was calculated as the ratio of the number of positive cells relative to the number of total cells.

Figure 5:
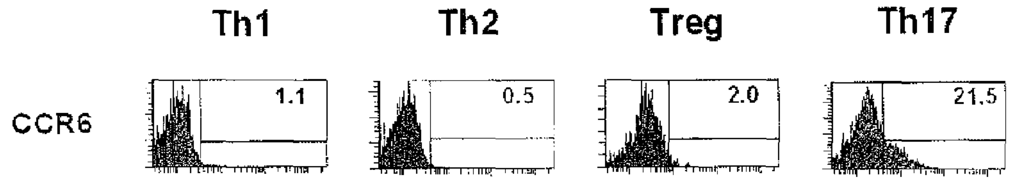
FIG. 5 shows histograms of fluorescent intensity obtained by the analysis of CCR6 measurement samples.
Figure 6:
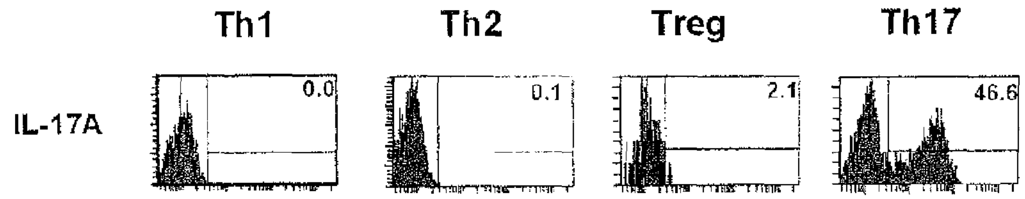
FIG. 6 shows histograms of fluorescent intensity obtained by the analysis of IL-17A measurement samples.
Figure 7:
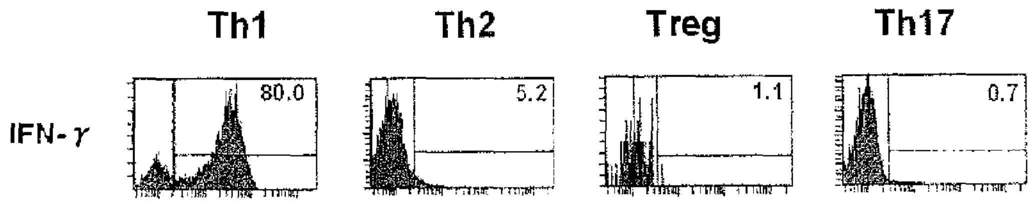
FIG. 7 shows histograms of fluorescent intensity obtained by the analysis of IFN-γ measurement samples.
Figure 8:
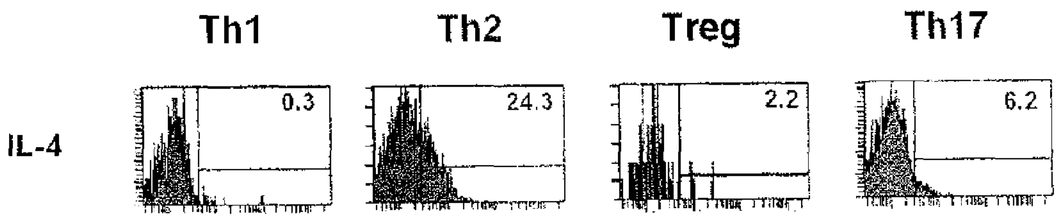
FIG. 8 shows histograms of fluorescent intensity obtained by the analysis of IL-4 measurement samples.
Figure 9:
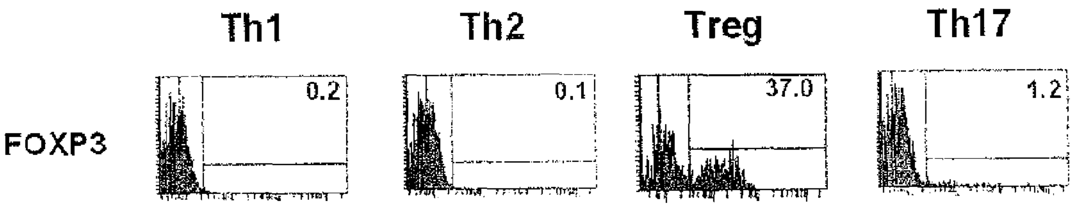
FIG. 9 shows histograms of fluorescent intensity obtained by the analysis of FOXP3 measurement samples.

CCR6 and IL-17A are known markers for Th17 cells. FIGS. 5 and 6 show that the expression levels of CCR6 and IL-17A proteins are high in Th17 cells. IFN-γ is a known marker for Th1 cells. FIG. 7 shows that the expression level of IFN-γ protein is high in Th1 cells. IL-4 is a known marker for Th2 cells. FIG. 8 shows that the expression level of IL-4 protein is high in Th2 cells. FOXP3 is a known marker for Treg cells. FIG. 9 shows that the expression level of FOXP3 protein is high in Treg cells. Thus, it is indicated that these measurement samples are suitable for expression analysis of protein markers.

Figure 2:
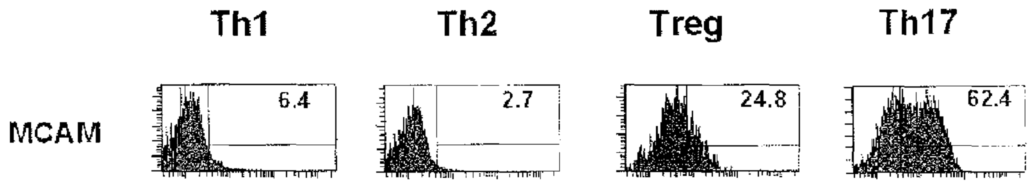
FIG. 2 shows histograms of fluorescent intensity obtained by the analysis of MCAM measurement samples.
Figure 3:
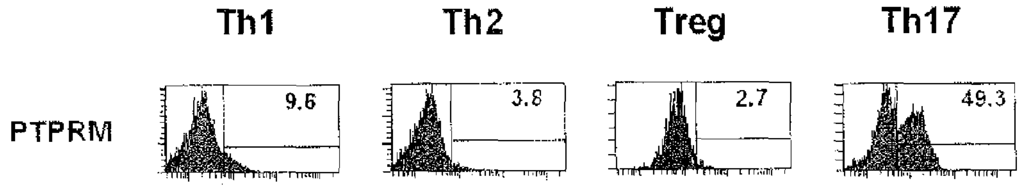
FIG. 3 shows histograms of fluorescent intensity obtained by the analysis of PTPRM measurement samples.
Figure 4:
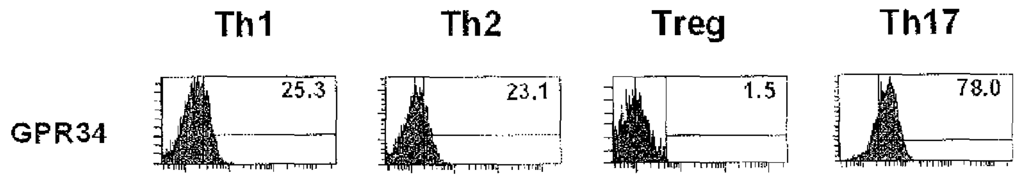
FIG. 4 shows histograms of fluorescent intensity obtained by the analysis of GPR34 measurement samples.

FIGS. 2 to 4 show that the expression levels of MCAM, PTPRM and GPR34 proteins are high in Th17 cells. It is also found that the ratios of positive cells in the MCAM measurement sample, PTPRM measurement sample and GPR34 measurement sample of Th17 cells were equal to or higher than the ratios of positive cells in the CCR6 measurement sample and IL-17A measurement sample. This reveals that the proteins encoded by the genes MCAM, PTPRM and GPR34 which were identified in Example 1 as the polynucleotide markers for detecting Th17 cells can also be used as protein markers for detecting Th17 cells.

EXAMPLE 3

Expression Analysis of Polynucleotide Markers for Detecting Th17 Cells by Real-Time PCR 1. Preparation of cDNA (1) Preparation of cDNA from Cells "without Activation Stimulation"

Total RNA (0.1 μg) of Th17 cells "without activation stimulation" extracted in Example 1 under the paragraph "3. Extraction of total RNA" was reverse-transcribed with a poly dT primer (Hokkaido System Science Co., Ltd.), random primers (Hokkaido System Science Co., Ltd.) and Superscript III reverse transcriptase (Invitrogen Corporation) to obtain cDNA of Th17 cells "without activation stimulation". Reverse transcription was carried out according to the attached instructions.

cDNAs of Th1 cells "without activation stimulation", of Th2 cells "without activation stimulation" and of Treg cells "without activation stimulation" were prepared in the similar manner as above except that total RNAs (0.1 μg) of Th1 cells, Th2 cells and Treg cells "without activation stimulation" were used instead of total RNA (0.1 μg) of Th17 cells "without stimulation".

The number of samples of the cells "without activation stimulation" used for preparation of cDNA is shown in Table 10.

TABLE 10

| | Th1 cells | Th2 cells | Th17 cells | Treg cells |
|---|---|---|---|---|
| w/o activation stimulation | 5 | 5 | 5 | 4 |

(2) Preparation of cDNA from Cells "with Activation Stimulation"

Th17 cells "without activation stimulation" prepared in Example 1 under the paragraph "2. Cell culture" were prepared in 5% FBS/RPMI at $2.5 \times 10^5$ cells/ml. Th17 cells were stimulated by incubating the cells at 37° C. for 3 hours with T cell activation/expansion kit (Miltenyi Biotec). These Th17 cells "with activation stimulation" were subjected to extraction of total RNA in the same manner as Example 1, "3. Extraction of total RNA". The extracted total RNA (0.1 μg) of Th17 cells "with activation stimulation" was reverse-transcribed with a poly dT primer (Hokkaido System Science Co., Ltd.), random primers (Hokkaido System Science Co., Ltd.) and Superscript III reverse transcriptase (Invitrogen Corporation) to obtain cDNA of Th17 cells "with activation stimulation". Reverse transcription was carried out according to the attached instructions.

cDNAs of Th1 cells "with activation stimulation", of Th2 cells "with activation stimulation" and of Treg cells "with activation stimulation" were prepared in the similar manner as above except that total RNAs (0.1 μg) of Th1 cells, Th2 cells and Treg cells "with activation stimulation" were used instead of total RNA (0.1 μg) of Th17 cells "with activation stimulation".

The number of samples of the cells "with activation stimulation" used for preparation of cDNA is shown in Table 11.

TABLE 11

| | Th1 cells | Th2 cells | Th17 cells | Treg cells |
|---|---|---|---|---|
| w/ activation stimulation | 5 | 5 | 5 | 3 |

2. Design of Primer Sets

The following primer sets were designed with Primer3 software.

(1) Primer Sets for Detecting Th17 Cells

Primer sets were designed for the genes ADAM12, ATP6V0A4, ATP9A, BVES, C5orf40, CDH4, DIO2, L1CAM, MCAM, SHROOM2, TMEM163, UPK1B, DRD2, PGBD5 (LOC100134440), ODZ4, SLC6A15, AKAP12, C9orf125, POPDC3, UNC13C, PCOLCE2, PNOC, TGFBI, IL1A, BHLHE22, PPARG, SIM1 and SNAI2, which were detected in Example 1 as the polynucleotide markers for detecting Th17 cells.

(2) Primer Sets for Known Markers for Th17 Cells

Primer sets were designed for known gene markers for Th17 cells, CCR6, RORC and IL-17A.

(3) Primer Sets for Known Markers for Th1 Cells

Primer sets were designed for known gene markers for Th1 cells, TBX21 and IFN-γ.

(4) Primer Sets for Known Markers for Th2 Cells

Primer sets were designed for known gene markers for Th2 cells, GATA3 and IL-4.

(5) Primer Sets for Known Markers for Treg Cells

Primer sets were designed for a known gene marker for Treg cells, FOXP3.

(6) Primer Sets for Internal Controls

Primer sets were designed for internal control genes, Gapdh, ACTB, B2M and UBC.

Designed primer sets are shown in Table 12.

TABLE 12

| Gene symbol | Forward primer | SEQ ID NO: | Reverse primer | SEQ ID NO: |
|---|---|---|---|---|
| ADAM12 | TCTCCCTCGCTCGAAATTACA | 181 | CAGAATATCCCCGTACATGTCCAT | 182 |
| ATP6V0A4 | TCCTTGAACATCTTTGGCTCTTC | 183 | TCCATGTGCCGTTTCTGAAC | 184 |
| ATP9A | AGAGGAGCAGTATCAGGACTTTGAA | 185 | AGCGGTCGTGCACACTCA | 186 |

TABLE 12-continued

| Gene symbol | Forward primer | SEQ ID NO: | Reverse primer | SEQ ID NO: |
|---|---|---|---|---|
| BVES | CGGCTTGCACCAGTTTCTTC | 187 | GCTCCTTCTTCTATCGGTTTCATC | 188 |
| C5orf40 | TCGGAGGGCAGAGCTCTAAC | 189 | CCTCGATGTTCATCCCGATT | 190 |
| CDH4 | GATCAGCCCCACTCTCCAAA | 191 | GATGGATCCCCACTGATGATG | 192 |
| DIO2 | CATGATGCTAAGAGTCCTGGGTAA | 193 | TTCTGCAACTGAGAAGCACATATG | 194 |
| L1CAM | CAAGGAGGGCCAGTGCAA | 195 | GAAGCCCCACCCTTCTCTTC | 196 |
| MCAM | GGGCATCCCTGTGAACAGTAA | 197 | GGTACCCGTTCCTCCCTACAC | 198 |
| SHROOM2 | TGCATGTTAATGGTGAGTGAATCC | 199 | TTGATCCAACAAATGCCCTAATAC | 200 |
| TMEM163 | GGTCAAACTCCTCATCGACATG | 201 | CCCCTTCACTCAAACATCTCGTA | 202 |
| UPK1B | CCAGTGGAAAAACAATGGAGTCA | 203 | ACAGCAATTGTCCTGGAGCAT | 204 |
| DRD2 | CTGCTCATCGCTGTCATCGT | 205 | CGGGACACAGCCATGCA | 206 |
| PGBD5 | AGAGTTTGAGAAGCAAGGGATTTACT | 207 | GGCCGGTGCAGTCACTCTT | 208 |
| ODZ4 | GCCCACAGACTTAGCCATCA | 209 | TCCCGGCGACAATGC | 210 |
| SLC6A15 | TGCCACCACCTATTACTGGTACA | 211 | AGTTTAAGCCCCCACTTTCAGAA | 212 |
| AKAP12 | TCCATAGCTGGGTCTGGTGTAGA | 213 | TTCTTGATTGAGACCCAGGATTC | 214 |
| C9orf125 | GAGAGGCTCCAGCACTACATCA | 215 | CTACACCAACCCATTCCAGGAT | 216 |
| POPDC3 | TTCAGTTCCTGGATTCTCCTGAGT | 217 | CAGTGAGGGTTACCTGAAAAATGC | 218 |
| UNC13C | TCAGGGACCAACCACCAAGA | 219 | CAGGACAGGTGTGTAGGCAGTTT | 220 |
| PCOLCE2 | CCACCACATTCCCTGTAACCA | 221 | TCCGTCTACACTTTTGTTGACACA | 222 |
| PNOC | CTCAGTCTCTTCTCCAGTGTGTTCA | 223 | GGAGCTTCTCCTGGCATGTG | 224 |
| TGFBI | GGGCGGCAAAAAACTGAGA | 225 | CCGCGATGCAGGTGTTCT | 226 |
| IL1A | CAATTGTATGTGACTGCCCAAGA | 227 | TGGGTATCTCAGGCATCTCCTT | 228 |
| BHLHE22 | TGCTCCCCACCCCCTTTA | 229 | CTGCTTTGTTTGCTCTGCAAGT | 230 |
| PPARG | CCTGAGCCACTGCCAACATT | 231 | AGGTGTCAGATTTTCCCTCAGAAT | 232 |
| SIM1 | CATGCCTCACATCGCTTCAG | 233 | CCACACTATCTTCATCCCAATGAC | 234 |
| SNAI2 | CTTGCCCTCACTGCAACAGA | 235 | TCTGCAGATGAGCCCTCAGA | 236 |
| TBX21 | GATGCGCCAGGAAGTTTCA | 237 | GACGCCCCCTTGTTGTTTG | 238 |
| GATA3 | GCGGGCTCTATCACAAAATGA | 239 | GCCTTCGCTTGGGCTTAAT | 240 |
| FOXP3 | CACCTGGCTGGGAAAATGG | 241 | GGAGCCCTTGTCGGATGAT | 242 |
| CCR6 | GGCAGTTCTCCAGGCTATTTGT | 243 | GGAGGCCAAAGACACAGATCA | 244 |
| RORC | CCAAGGCTCAGTCATGAGAACA | 245 | GCGGAAGAAGCCCTTGCA | 246 |
| IFNG | CCAACGCAAAGCAATACATGA | 247 | CGAAACAGCATCTGACTCCTTTT | 248 |
| IL4 | TGGGTCTCACCTCCCAACTG | 249 | GCCGGCACATGCTAGCA | 250 |
| IL17A | CCCAAAAGGTCCTCAGATTACTACA | 251 | CATTGCGGTGGAGATTCCA | 252 |
| GAPDH | ACCCACTCCTCCACCTTTGA | 253 | TTGCTGTAGCCAAATTCGTTGT | 254 |
| ACTB | CAGCAGATGTGGATCAGCAAG | 255 | GCATTTGCGGTGGACGAT | 256 |
| B2M | TGCTGTCTCCATGTTTGATGTATCT | 257 | TCTCTGCTCCCCACCTCTAAGT | 258 |
| UBC | GTCGCAGCCGGGATTTG | 259 | GCATTGTCAAGTGACGATCACA | 260 |

3. Expression Analysis of Gene Markers by Real-Time PCR (1) Real-Time PCR Using cDNAs of Cells "Without Activation Stimulation" as Templates cDNAs of Th17 cells "without activation stimulation" obtained from samples in the above "1. Preparation of cDNA" were respectively used as a template. The primer sets used were the primer sets for ADAM12, ATP6V0A4, ATP9A, BVES, C5orf40, CDH4, DIO2, L1CAM, MCAM, SHROOM2, TMEM163, UPK1B, DRD2, PGBD5, ODZ4, SLC6A15, AKAP12, C9orf125, POPDC3, UNC13C, PCOLCE2, PNOC, TGFBI, IL1A, BHLHE22, PPARG, SIM1, SNAI2, TBX21, GATA3, FOXP3, CCR6, RORC, GAPDH, ACTB, B2M and UBC, which were designed as described in "2. Design of primer sets". Real-time PCR was carried out with the template, primer sets and Power SYBR Green PCR Master Mix (Applied Biosystems) in 7300 Real Time PCR System (Applied Biosystems) and Ct value of each gene was measured. PCR was carried out at 50° C. for 2 minutes, 95° C. for 10 minutes followed by 45 cycles of 95° C. for 15 seconds and 60° C. for 1 minute and two cycles of 95° C. for 15 seconds and 60° C. for 1 minute. Ct value was measured by automatic calculation on 7300 Fast SDS software (Applied Biosystems).

Real-time PCR was also carried out in the similar manner as above except that cDNAs of Th1 cells "without activation stimulation" obtained from 5 samples, cDNAs of Th2 cells "without activation stimulation" obtained from 5 samples and cDNAs of Treg cells "without activation stimulation" obtained from 4 samples were used as a template instead of cDNAs of Th17 cells "without activation stimulation", and Ct values for the genes were measured.

(2) Real-Time PCR Using cDNAs of Cells "with Activation Stimulation" as Templates cDNAs of Th17 cells "with activation stimulation" obtained from 5 samples in the above "1. Preparation of cDNA" were used as a template. The primer sets used were the primer sets for AKAP12, C9orf125, POPDC3, UNC13C, PCOLCE2, PNOC, TGFBI, IFNG, IL4, IL17A, GAPDH, ACTB, B2M and UBC, which were designed as described in "2. Design of primer sets". Real-time PCR was carried out with the template, primer sets and Power SYBR Green PCR Master Mix (Applied Biosystems) in 7300 Real Time PCR System (Applied Biosystems) and Ct value of each gene was measured. PCR was carried out at 50° C. for 2 minutes, 95° C. for 10 minutes followed by 45 cycles of 95° C. for 15 seconds and 60° C. for 1 minute and two cycles of 95° C. for 15 seconds and 60° C. for 1 minute. Ct value was measured by automatic calculation on 7300 Fast SDS software (Applied Biosystems).

Real-time PCR was also carried out in the similar manner as above except that cDNAs of Th1 cells "with activation stimulation" obtained from 5 samples, cDNAs of Th2 cells "with activation stimulation" obtained from 5 samples and cDNAs of Treg cells "with activation stimulation" obtained from 3 samples were used as a template instead of cDNAs of Th17 cells "with activation stimulation", and Ct values for the genes were measured.

(3) Analysis of Expression Level

Based on the Ct values obtained from real-time PCR, expression levels of the gene markers were calculated according to the formula (I):

$$\text{(Expression level of a gene)}=100000\times 2^{-y} \quad \text{(I)}$$

wherein: y=(Ct value of a gene)−(((Ct value of Gapdh gene)+(Ct value of ACTB gene)+(Ct value of B2M gene)+(Ct value of UBC gene))/4)

The expression level of each gene marker in Th17 cells "without activation stimulation" was obtained as an average of the expression levels of the gene marker in question obtained from five cDNAs used as templates. The expression level of each gene marker in Th17 cells "with activation stimulation" was also obtained as an average of the expression levels of the gene marker in question obtained from five cDNAs used as templates.

Similarly, the expression level of each gene marker in Th1 cells or Th2 cells "without activation stimulation" or "with activation stimulation" was obtained as an average of the expression levels of the gene marker in question obtained from five cDNAs used as templates. The expression level of each gene marker in Treg cells "without activation expression" was obtained as an average of the expression levels of the gene marker in question obtained from four cDNAs used as templates. The expression level of each gene marker in Treg cells "with activation stimulation" was obtained as an average of the expression levels of the gene marker in question obtained from three cDNAs used as templates.

Expression levels of the gene markers are shown in Tables 13 and 14. Table 13 shows expression levels of gene markers in Th1, Th2, Treg and Th17 cells "without activation stimulation" and Table 14 shows expression levels of gene markers in Th1, Th2, Treg and Th17 cells "with activation stimulation"

Expression levels of gene markers in the cells "without activation stimulation"

TABLE 13

| Location of | | Expression level | | | |
|---|---|---|---|---|---|
| encoded protein | Gene symbol | Th1 | Th2 | Treg | Th17 |
| Membrane | ADAM12 | 9.95 | 0.55 | 22.08 | 193.83 |
| | ATP6V0A4 | 35.21 | 2.55 | 7.17 | 625.03 |
| | ATP9A | 125.11 | 9.08 | 41.42 | 407.43 |
| | BVES | 23.85 | 3.58 | 6.84 | 77.99 |
| | C5orf40 | 0.74 | 0.00 | 33.36 | 107.84 |
| | CDH4 | 4.93 | 7.47 | 29.44 | 143.90 |
| | DIO2 | 0.46 | 1.25 | 0.91 | 10.40 |
| | L1CAM | 41.95 | 45.03 | 72.77 | 220.54 |
| | MCAM | 62.69 | 18.93 | 159.46 | 500.64 |
| | SHROOM2 | 0.22 | 0.46 | 0.90 | 11.44 |
| | TMEM163 | 13.77 | 8.78 | 24.25 | 249.56 |
| | UPK1B | 2.94 | 0.12 | 0.55 | 22.59 |
| | DRD2 | 51.14 | 49.86 | 58.21 | 884.06 |
| | PGBD5 | 10.30 | 11.96 | 19.04 | 157.52 |
| | ODZ4 | 1.14 | 0.44 | 0.39 | 41.82 |
| | SLC6A15 | 0.50 | 3.46 | 2.65 | 27.71 |
| | AKAP12 | 29.57 | 30.67 | 46.71 | 110.16 |
| | C9orf125 | 1.31 | 0.50 | 3.43 | 39.73 |
| | POPDC3 | 0.23 | 0.00 | 0.52 | 10.19 |
| | UNC13C | 0.08 | 0.08 | 0.27 | 12.10 |
| Extracellular/ | PCOLCE2 | 0.60 | 0.00 | 2.59 | 15.64 |
| secreted | PNOC | 8.01 | 25.75 | 5.43 | 335.81 |
| | TGFBI | 58.45 | 31.18 | 253.89 | 1427.38 |
| | IL1A | 13.47 | 47.92 | 128.89 | 502.06 |
| Intracellular | BHLHE22 | 32.48 | 13.80 | 29.69 | 247.81 |
| | PPARG | 120.16 | 16.40 | 92.84 | 456.67 |
| | SIM1 | 143.63 | 229.39 | 40.78 | 837.78 |
| | SNAI2 | 0.15 | 0.03 | 4.20 | 69.35 |

TABLE 13-continued

| Location of encoded protein | Gene symbol | Expression level | | | |
|---|---|---|---|---|---|
| | | Th1 | Th2 | Treg | Th17 |
| Known markers | TBX21 | 4851.97 | 21.94 | 513.23 | 26.92 |
| | GATA3 | 1820.22 | 5684.93 | 4811.71 | 1353.37 |
| | FOXP3 | 471.34 | 250.11 | 21799.93 | 334.68 |
| | CCR6 | 102.73 | 42.69 | 939.98 | 401.01 |
| | RORC | 96.77 | 3.75 | 328.99 | 788.05 |

Expression levels of gene markers in the cells "with activation stimulation

TABLE 14

| Location of encoded protein | Gene symbol | Expression level | | | |
|---|---|---|---|---|---|
| | | Th1 | Th2 | Treg | Th17 |
| Membrane | AKAP12 | 34.55 | 59.13 | 40.36 | 201.43 |
| | C9orf125 | 0.51 | 0.00 | 1.92 | 35.77 |
| | POPDC3 | 7.28 | 2.60 | 3.42 | 28.09 |
| | UNC13C | 0.04 | 0.36 | 1.76 | 11.11 |
| Extracellular/ secreted | PCOLCE2 | 1.01 | 0.36 | 2.04 | 20.82 |
| | PNOC | 10.33 | 28.87 | 0.63 | 289.07 |
| | TGFBI | 39.99 | 6.24 | 86.85 | 861.02 |
| Known markers | IFNG | 191944.46 | 393.70 | 1593.07 | 1118.25 |
| | IL4 | 4011.14 | 8401.51 | 329.94 | 108.98 |
| | IL17A | 84.43 | 458.57 | 1600.38 | 34052.24 |

Expression levels of gene markers in Th17 cells and ratios thereof relative to the expression levels of the gene markers in Th1, Th2 and Treg cells are shown in Tables 15 and 16. Table 15 shows expression levels of gene markers in Th17 cells "without activation stimulation" and ratios thereof relative to the expression levels of the gene markers in Th1, Th2 and Treg cells "without activation stimulation". Table 16 shows expression levels of gene markers in Th17 cells "with activation stimulation" and ratios thereof relative to the expression levels of the gene markers in Th1, Th2 and Treg cells "with activation stimulation". The values shown in the columns of Th17/Th1, Th17/Th2 and Th17/Treg in Tables 15 and 16 were calculated as follows:

*Th*17/*Th*1=(Expression level in *Th*17 cells)/(Expression level in *Th*1 cells)

*Th*17/*Th*2=(Expression level in *Th*17 cells)/(Expression level in *Th*2 cells)

*Th*17/*Treg*=(Expression level in *Th*17 cells)/(Expression level in *Treg* cells)

TABLE 15

| Location of encoded protein | Gene symbol | Expression ratio | | |
|---|---|---|---|---|
| | | Th17/Th1 | Th17/Th2 | Th17/Treg |
| Membrane | ADAM12 | 19.49 | 352.65 | 8.78 |
| | ATP6V0A4 | 17.75 | 245.31 | 87.13 |
| | ATP9A | 3.26 | 44.86 | 9.84 |
| | BVES | 3.27 | 21.80 | 11.41 |
| | C5orf40 | 144.92 | ∞ | 3.23 |
| | CDH4 | 29.17 | 19.26 | 4.89 |
| | DIO2 | 22.83 | 8.34 | 11.42 |
| | L1CAM | 5.26 | 4.90 | 3.03 |
| | MCAM | 7.99 | 26.44 | 3.14 |
| | SHROOM2 | 53.13 | 24.85 | 12.71 |
| | TMEM163 | 18.13 | 28.42 | 10.29 |
| | UPK1B | 7.69 | 191.37 | 41.23 |
| | DRD2 | 17.29 | 17.73 | 15.19 |
| | PGBD5 | 15.30 | 13.17 | 8.27 |

TABLE 15-continued

| Location of encoded protein | Gene symbol | Expression ratio | | |
|---|---|---|---|---|
| | | Th17/Th1 | Th17/Th2 | Th17/Treg |
| | ODZ4 | 36.59 | 94.68 | 106.41 |
| | SLC6A15 | 55.24 | 8.01 | 10.47 |
| | AKAP12 | 3.72 | 3.59 | 2.36 |
| | C9orf125 | 30.34 | 79.90 | 11.59 |
| | POPDC3 | 44.01 | ∞ | 19.75 |
| | UNC13C | 152.73 | 157.50 | 44.10 |
| Extracellular/ secreted | PCOLCE2 | 25.86 | 4097.03 | 6.04 |
| | PNOC | 41.93 | 13.04 | 61.86 |
| | TGFBI | 24.42 | 45.77 | 5.62 |
| | IL1A | 37.28 | 10.48 | 3.90 |
| Intracellular | BHLHE22 | 7.63 | 17.96 | 8.35 |
| | PPARG | 3.80 | 27.85 | 4.92 |
| | SIM1 | 5.83 | 3.65 | 20.54 |
| | SNAI2 | 466.76 | 2536.05 | 16.52 |
| Known markers | TBX21 | 0.01 | 1.23 | 0.05 |
| | GATA3 | 0.74 | 0.24 | 0.28 |
| | FOXP3 | 0.71 | 1.34 | 0.02 |
| | CCR6 | 3.90 | 9.39 | 0.43 |
| | RORC | 8.14 | 210.37 | 2.40 |

TABLE 16

| Location of encoded protein | Gene symbol | Expression ratio | | |
|---|---|---|---|---|
| | | Th17/Th1 | Th17/Th2 | Th17/Treg |
| Membrane | AKAP12 | 5.83 | 3.41 | 4.99 |
| | C9orf125 | 69.61 | ∞ | 18.59 |
| | POPDC3 | 3.86 | 10.79 | 8.20 |
| | UNC13C | 266.35 | 31.25 | 6.30 |
| Extracellular/ secreted | PCOLCE2 | 20.54 | 58.21 | 10.22 |
| | PNOC | 27.99 | 10.01 | 456.13 |
| | TGFBI | 21.53 | 138.01 | 9.91 |
| Known markers | IFN-γ | 0.01 | 2.84 | 0.70 |
| | IL-4 | 0.03 | 0.01 | 0.33 |
| | IL-17A | 403.31 | 74.26 | 21.28 |

Table 15 shows that the expression levels of ADAM12, ATP6V0A4, ATP9A, BVES, C5orf40, CDH4, DIO2, L1CAM, MCAM, SHROOM2, TMEM163, UPK1B, DRD2, PGBD5, ODZ4, SLC6A15, AKAP12, C9orf125, POPDC3, UNC13C, PCOLCE2, PNOC, TGFBI, IL1A, BHLHE22, PPARG, SIM1 and SNAI2 in Th17 cells "without activation stimulation" are two or more times higher than that in Th1, Th2 and Treg cells "without activation stimulation".

Table 16 shows that the expression levels of AKAP12, C9orf125, POPDC3, UNC13C, PCOLCE2, PNOC and TGFBI in Th17 cells "with activation stimulation" are two or more times higher than that in Th1, Th2 and Treg cells "with activation stimulation".

Thus, it is demonstrated that these genes are useful as polynucleotide markers for detecting Th17 cells.

EXAMPLE 4

Expression Analysis of Polynucleotide Markers in Healthy Subjects and Patients with Rheumatoid Arthritis 1. Isolation of CD4 Positive Cells from Peripheral Blood of Healthy Subjects and Patients with Rheumatoid Arthritis Peripheral blood from healthy adults (healthy subjects) and patients with rheumatoid arthritis was collected in blood collecting tubes NP-HE0557 (NIPRO) and peripheral blood CD4 positive cells were isolated with magnetic beads bound to anti-CD4 antibody (Miltenyi Biotec). Isolation of CD4 positive cells using anti-CD4 antibody beads was carried out according to the attached instruction.

2. Preparation of cDNA from Peripheral Blood CD4 Positive Cells

Total RNA was extracted from the isolated peripheral blood CD4 positive cells in the same manner as Example 1, “3. Extraction of total RNA”. The extracted total RNA (0.1 μg) of peripheral blood CD4 positive cells were reverse-transcribed with a poly dT primer (Hokkaido System Science Co., Ltd.), random primers (Hokkaido System Science Co., Ltd.) and Superscript III reverse transcriptase (Invitrogen Corporation) to obtain cDNA of peripheral blood CD4 positive cells. Reverse transcription was carried out according to the attached instructions.

The number of samples of peripheral blood CD4 positive cells used for preparation of cDNA is shown in Table 17.

TABLE 17

| | Healthy subject | Patient with rheumatoid arthritis |
|---|---|---|
| w/o activation stimulation | 9 | 9 |

3. Expression Analysis of Gene Markers by Real-Time PCR (1) Real-Time PCR Using cDNAs of Peripheral Blood CD4 Positive Cells as Templates cDNAs of peripheral blood CD4 positive cells obtained from nine healthy subjects and nine patients with rheumatoid arthritis as prepared in the above “2. Preparation of cDNA from peripheral blood CD4 positive cells” were used as templates. The primer sets used were the primer sets for ATP6V0A4, BVES, C5orf40, UPK1B, DRD2, PCOLCE2, PNOC, TGFBI, BHLHE22, SIM1, CCR6, RORC, GAPDH, ACTB, B2M, and UBC, which were designed as described in “2. Design of primer sets”. Real-time PCR was carried out with the template, primer sets and Power SYBR Green PCR Master Mix (Applied Biosystems) in 7300 Real Time PCR System (Applied Biosystems) and Ct value of each gene was measured. PCR was carried out at 50° C. for 2 minutes, 95° C. for 10 minutes followed by 45 cycles of 95° C. for 15 seconds and 60° C. for 1 minute and two cycles of 95° C. for 15 seconds and 60° C. for 1 minute. Ct value was measured by automatic calculation on 7300 Fast SDS software (Applied Biosystems).

(2) Analysis of Expression Level

Expression levels of the gene markers were calculated according to the above formula (I). The expression level of each gene marker in peripheral blood CD4 positive cells of the patients with rheumatoid arthritis was obtained as an average of the expression levels of the gene marker in question obtained from nine cDNAs used as templates. Similarly, the expression level of each gene marker in peripheral blood CD4 positive cells of the healthy subjects was obtained as an average of the expression levels of the gene marker in question obtained from nine cDNAs used as templates.

Expression levels of the gene markers in peripheral blood CD4 positive cells from healthy subjects and patients with rheumatoid arthritis and expression ratios of the gene markers between peripheral blood CD4 positive cells of healthy subjects and patients with rheumatoid arthritis are shown in Table 18. In Table 18, “RA” denotes patients with rheumatoid arthritis and “HC” denotes healthy subjects. The values shown in the column RA group/HC group were calculated as follows:

*RA* group/*HC* group=(Expression level in peripheral blood *CD*4 positive cells of patients with rheumatoid arthritis)/(Expression level in peripheral blood *CD*4 positive cells of healthy subjects)

TABLE 18

| Location of encoded protein | Gene symbol | Expression level HC group | Expression level RA group | Expression ratio RA group/HC group |
|---|---|---|---|---|
| Membrane | ATP6V0A4 | 6.44 | 52.16 | 8.10 |
| | BVES | 0.08 | 32.79 | 403.57 |
| | C5orf40 | 0.04 | 21.60 | 496.29 |
| | UPK1B | 0.31 | 39.65 | 126.98 |
| | DRD2 | 59.42 | 243.55 | 4.10 |
| Extracellular/secreted | PCOLCE2 | 0.07 | 4.94 | 70.29 |
| | PNOC | 18.89 | 73.38 | 3.88 |
| | TGFBI | 1651.40 | 5413.26 | 3.28 |
| Intracellular | BHLHE22 | 3.15 | 27.75 | 8.81 |
| | SIM1 | 4.75 | 20.73 | 4.36 |
| Known markers | CCR6 | 3136.22 | 4316.17 | 1.38 |
| | RORC | 528.64 | 421.20 | 0.80 |

Table 18 shows that the expression levels of ATP6V0A4, BVES, C5orf40, UPK1B, DRD2, PCOLCE2, PNOC, TGFBI, BHLHE22 and SIM1 in the RA group were three or more times higher than that in the HC group. This indicates that these genes are useful as polynucleotide markers for screening of patients with rheumatoid arthritis.

EXAMPLE 5

Analysis of Expression Ratios of Polynucleotide Markers in Cultured Th17 and Th22 Cells Derived from Human Peripheral Blood 1. Isolation of Th17 and Th22 Cells from Human Peripheral Blood Buffy coat obtained from peripheral blood of a healthy adult was overlaid on Ficoll-paque plus solution (GE Healthcare Bioscience) and centrifuged to obtain a monocyte fraction. Crude CD4 positive cells were purified from the fraction by using magnetic beads bound to anti-CD4 antibody (Miltenyi Biotec).

The obtained CD4 positive cells were stained with the fluorescence labeled antibodies shown in Table 19 and then Th17 and Th22 cells were separated by a cell sorter (FACS Aria: Becton Dickinson). The separation was carried out with the gating shown in Table 20.

TABLE 19

| Antigen | Fluorescent labeling substance | Clone | Manufacturer |
|---|---|---|---|
| CD4 | APC-Cy7 | RPA-T4 | BD Biosciences |
| CD25 | PE-Cy7 | BC96 | eBioscience |
| CXCR3 | Alexa Fluor ™ 488 | 1C6/CXCR3 | BD Biosciences |
| CCR4 | APC | FAB1567A | R&D systems |
| CCR6 | PE | 11A9 | BD Biosciences |
| CD45RA | APC | HI100 | BioLegend |
| CCR10 | PE | 6588-5 | BioLegend |

TABLE 20

| Cell | Gating |
|---|---|
| Th17 | $CD4^{high}$ $CD25^{low\text{-}negative}$ $CXCR3^-$ $CCR6^+$ $CCR4^+$ |
| Th22 | $CD4^{high}$ $CD25^{low\text{-}negative}$ $CD45RA^-$ $CXCR3^-$ $CCR10^+$ |

The above gating is described in detail in the reference by Acosta-Rodriguez E V et al. (Surface phenotype and antigenic specificity of human interleukin 17-producing T helper memory cells, Nat Immunol., vol. 8, p. 639-646 (2007)).

2. Th17 and Th22 Cell Cultures

Th17 and Th22 cells derived from adult peripheral blood obtained in the above step 1. were respectively plated in a 96-well plate at the density of $1.5\times10^5$ cells/0.3 ml/well. The medium used was Yssel medium (IMDM, 1% human serum of AB-type, 0.25% BSA, 1.8 mg/l 2-aminomethanol, 40 mg/l transferrin, 5 mg/l insulin, 2 mg/l linoleic acid, 2 mg/l oleic acid, 2 mg/l palmitic acid, 1% penicillin/streptomycin).

For activation and proliferation of the above cells, magnetic beads coated with anti-CD2/3/28 antibody (Miltenyi Biotec) (hereinafter also referred to as "antibody beads") were added at $0.75\times10^5$ per well. After addition of cytokines and neutralizing antibodies suitable for differentiation culture of respective Th17 and Th22 cells, cells were incubated in an incubator at 37° C. with 5% $CO_2$. Cytokines and neutralizing antibodies used are shown in Table 21.

TABLE 21

| Cell | Cytokine | Neutralizing antibody (clone) |
|---|---|---|
| Th17 | TGF-β1, IL-6, IL-23, IL-21, IL-1β, TNFα, IL-2 | Anti-IL-4 antibody (MP4-25D2), Anti-IFN-γ antibody (R4-6A2), |
| Th22 | IL-6, TNFα, IL-2 | Anti-IL-4 antibody (MP4-25D2), Anti-IFN-γ antibody (R4-6A2), Anti-TGFβ antibody (9016) |

The concentrations of the above cytokines were 50 ng/ml for IL-6 and 10 ng/ml for other than IL-6. The concentrations of antibodies were 10 μg/ml for anti-IFN-γ antibody, 2.5 μg/ml for anti-IL-4 antibody and 2.5 μg/ml for anti-TGF-β antibody.

The cytokines and neutralizing antibodies were obtained from R&D systems and eBioscience, respectively.

After three days from the start of culture, cells were diluted three-fold with the medium containing the above cytokines and antibodies and cultured for further seven days (10 days in total).

After ten days from the start of culture, the obtained Th17 and Th22 cells were respectively divided into two equal parts, and one was washed with Yssel medium and PBS before centrifugation to collect cells, which were stored at −80° C. until the subsequent RNA extraction step. These cells were designated as Th17 and Th22 cells "without activation stimulation". The other half was added with the antibody beads and cultured for three more hours to re-activate the cells. The cells were collected by centrifugation and similarly stored at −80° C. These cells were designated as Th17 and Th22 cells "with activation stimulation".

3. Extraction of Total RNA

The cells obtained as the above step 2. were subjected to extraction of total RNAs using RNeasy Plus Mini kit and RNeasy micro kit (QIAGEN). The specific procedures were according to the attached instructions of the kits.

4. Expression Analysis by Microarray

Total RNAs (10 to 100 ng) extracted from the cells as the above step 3. were reverse-transcribed to cDNAs with Two- Cycle Target Labeling and Control Reagents (Affymetrix), and further transcribed to biotinylated-cRNAs. The amplified biotinylated-cRNAs (20 μg) were fragmented. The specific procedures were according to the attached instructions of the kit.

The biotinylated-cRNAs derived from the cells as obtained above (15 μg) were applied to GeneChip Human Genome U-133 Plus 2.0 Array (Affymetrix) as samples, transferred to GeneChip Hybridization Oven 640 (Affymetrix) and hybridized under the conditions of 45° C. and 60 rpm for 16 hours.

After completion of the hybridization, the microarray was washed and fluorescence-labeled in GeneChip Fluidic Station 450 (Affymetrix), and scanned in GeneChip Scanner 3000 7G (Affymetrix) to obtain fluorescent intensity data.

The fluorescent data obtained were standardized with the expression analysis software GeneSpring Ver.11 (Agilent Technologies) based on MAS5 algorithm to obtain relative fluorescent intensities of the genes in the cells. The relative fluorescent intensities correspond to the expression levels of the genes in these cells.

Tables 22 and 23 show the results of the relative fluorescent intensities of the genes corresponding to the polynucleotide markers in Th17 cells obtained in Example 1 compared to those in Th22 cells. Table 22 shows expression ratios of the polynucleotide markers in Th17 and Th22 cells "without activation stimulation" and Table 23 shows expression ratios of the polynucleotide markers in Th17 and Th22 cells "with activation stimulation". In the tables, values in the column "Th17/Th22" correspond to the values obtained by dividing the relative fluorescent intensity of a gene corresponding to a polynucleotide marker in Th17 cells by that in Th22 cells.

TABLE 22

| Location of encoded protein | Gene symbol | Expression ratio Th22/Th17 |
|---|---|---|
| Membrane | ADAM12 | 11.1 |
| | ATP6V0A4 | 521.3 |
| | ATP9A | 33.9 |
| | BVES | 3.5 |
| | C5orf40 | 7.7 |
| | CDH4 | 12.5 |
| | DIO2 | 10.6 |
| | MCAM | 10.5 |
| | SHROOM2 | 5.2 |
| | TMEM163 | 5.6 |
| | | 3.8 |
| | UPK1B | 9.2 |
| | DRD2 | 5.8 |
| | LOC100134440, PGBD5 | 14.5 |
| | ODZ4 | 8.2 |
| | SLC6A15 | 12.2 |
| | AKAP12 | 17.2 |
| | | 36.1 |
| | C9orf125 | 3.3 |
| Extracellular/ secreted | PCOLCE2 | 9.0 |
| | PNOC | 38.5 |
| | TGFBI | 182.0 |
| | IL1A | 17.7 |

TABLE 22-continued

| Location of encoded protein | Gene symbol | Expression ratio Th22/Th17 |
|---|---|---|
| Intracellular | BHLHE22 | 108.3 |
| | PPARG | 13.6 |
| | SIM1 | 4.6 |
| | | 5.0 |
| | SNAI2 | 8.2 |
| Membrane | PTPRM | 36.3 |

TABLE 23

| Location of encoded protein | Gene symbol | Expression ratio Th17/Th22 |
|---|---|---|
| Membrane | AKAP12 | 12.8 |
| | | 22.9 |

TABLE 23-continued

| Location of encoded protein | Gene symbol | Expression ratio Th17/Th22 |
|---|---|---|
| | C9orf125 | 6.8 |
| | POPDC3 | 5.4 |
| Extracellular/ secreted | PCOLCE2 | 11.9 |
| | PNOC | 8.5 |
| | TGFBI | 367.4 |
| Membrane | GPR34 | 28.2 |

Tables 22 and 23 clearly indicate that the polynucleotide markers in Th17 cells obtained in Example 1 are expressed three or more times higher in Th17 cells than in Th22 cells. Thus, it is demonstrated that the polynucleotide markers shown in Tables 22 and 23 are useful for detection of Th17 cells.

What is claimed is:

1. A method for detecting human IL-17-producing helper T-cells comprising:

isolating CD4-positive cells from a blood sample with an anti-CD4 antibody;

mixing at least some of said CD4-positive cells with a labeling substance and with an antibody that specifically binds to a protein encoded by a PTPRM gene, wherein one or more of the CD4-positive cells, the antibody that specifically binds to a protein encoded by a PTPRM gene, and the labeling substance, form a complex;

applying said complex to a flow cytometer; and detecting the presence of an IL-17-producing helper T-cell by detecting the label of the complex using the flow cytometer, wherein said sample is determined to contain a human IL-17-producing helper T-cell when the label is detected with the flow cytometer in the detecting step.

2. The method according to claim 1, further comprising detecting a protein encoded by a MCAM gene.

3. The method according to claim 1, further comprising detecting a protein encoded by a L1CAM gene.

4. The method according to claim 1, further comprising detecting a protein encoded by a GPR34 gene.

5. The method according to claim 1, further comprising detecting a protein encoded by a gene, wherein the gene is selected from the group consisting of:

genes encoding membrane proteins consisting of: ADAM12, ANKS1B, ATP6V0A4, ATP9A, BVES, C5orf40, CDH4, DIO2, DMD, IRS2, KCNE3, MFAP3L, MYO7A, SHROOM2, SLC16A4, SLCO2B1, TANC2, TJP1, TMEM163, TNS3, UPK1B, WDFY3, DRD2, GJC1, PGBD5 (LOC100134440), MS4A7, ODZ4, PHKA1, RGS1, SHB, SLC44A3, SLC6A15, SYNGR3, AKAP12, C9orf125, DPY19L2, HRH4, MUC20, POPDC3, SORBS1, TANC1, TMEM44 and UNC13C;

genes encoding secretory proteins consisting of: CXCL13, PCOLCE2, PNOC, SMPDL3A, TGFBI, C17orf99, EBI3, IL1A and WNT3;

genes encoding intracellular proteins consisting of: BCAT1, BHLHE22, C13orf18 (LOC728970), CA2, CCDC3, CDS1, CHN1, CLIC5 (LOC100131610), CTSH, CYP7B1, DAPK2, DMRT1, DSE, FBXL17, FBXL21, FHOD3, H2AFY2, HLX, IRAK3, MACC1, MAML3, MYO10, OTUB2, PAPSS2, PCBP3, PDE4DIP, PLD1, PPARG, PTPN13, RGS18, SIM1, SNAI2, SOX2, SPIRE1, TBC1D12, TGM5, TMOD1, TUBB6, DDIT4L, DHRS9, ERC2, FERMT2, HHEX, HS3ST1, NR5A2, PHLDA1, RBM20, NINL, RTN2, SH3RF2, TSHZ2, EML1, HIST1H2BC, MAP3K4, PDK4, RGS2 and RGS20;

genes consisting of: C1orf106, C6orf145, LOC401097, MAMLD1, ZC3H12C, C12orf64, C6orf168, CAMSAP1L1 and MAGED4 (MAGED4B); and genes comprising at least one nucleic acid sequence selected from SEQ ID NO: 147 to 151, 157 to 162 and 167 to 174.

6. The method according to claim 5, wherein the gene is selected from the group consisting of:

genes encoding membrane proteins consisting of: ADAM12, ATP6V0A4, ATP9A, BVES, C5orf40, CDH4, DIO2, SHROOM2, TMEM163, UPK1B, DRD2, PGBD5 (LOC100134440), ODZ4, SLC6A15, AKAP12, C9orf125, POPDC3 and UNC13C;

genes encoding secretory proteins consisting of: PCOLCE2, PNOC, TGFBI and IL1A; and genes encoding intracellular proteins consisting of BHLHE22, PPARG, SIM1 and SNAI2.

* * * * *

SEQUENCE LISTING

<160> NUMBER OF SEQ ID NOS: 260

<210> SEQ ID NO 1
<211> LENGTH: 500
<212> TYPE: DNA
<213> ORGANISM: Homo sapiens

<400> SEQUENCE: 1
gtcttctgga ctggttttca cattagaaga caattgacaa cagttacata attcactctg 60
agtgttttat gagaaagcct tcttttgggg tcaacagttt tcctatgctt tgaaacagaa 120
aaatatgtac caagaatctt ggtttgcctt ccagaaaaca aaactgcatt tcactttccc 180
ggtgttcccc actgtatcta ggcaacatag tattcatgac tatggataaa ctaaacacgt 240
gacacaaaca cacacaaaag ggaacccagc tctaatacat tccaactcgt atagcatgca 300
tctgtttatt ctatagttat taagttcttt aaaatgtaaa gccatgctgg aaaataatac 360
tgctgagata catacagaat tactgtaact gattacactt ggtaattgta ctaaagccaa 420
acatatatat actattaaaa aggtttacag aattttatgg tgcattacgt gggcattgtc 480
tttttagatg cccaaatcct 500

<210> SEQ ID NO 2
<211> LENGTH: 541
<212> TYPE: DNA
<213> ORGANISM: Homo sapiens
<220> FEATURE:
<221> NAME/KEY: misc_feature
<222> LOCATION: (42)..(43)
<223> OTHER INFORMATION: n is a, c, g, t or u
<220> FEATURE:
<221> NAME/KEY: misc_feature
<222> LOCATION: (45)..(49)
<223> OTHER INFORMATION: n is a, c, g, t or u
<220> FEATURE:
<221> NAME/KEY: misc_feature
<222> LOCATION: (418)..(419)
<223> OTHER INFORMATION: n is a, c, g, t or u
<220> FEATURE:
<221> NAME/KEY: misc_feature
<222> LOCATION: (496)..(496)
<223> OTHER INFORMATION: n is a, c, g, t or u

<400> SEQUENCE: 2
cacctccaaa gcatctgtaa aatcattcta tcattgagta tnntnnnnng caaaaggaca 60
aaaacaactc ccgtgatatg attgccagga gattctgttt ccccatttct atatttgtgg 120
attttatatg taatcaccta tgtcagagaa agaaaacctt tcaaccaaat gattggttca 180
aaaggaaaga atgattcaaa gcagaggaat ttattatgca cagcaaaatg tgtcttgtat 240
taaatatttt tattaaaaga atgtttcatt aatgcattga taagaaaact aggttagttg 300
cgagggatgt ttctggtttc atttcaaata attaaatttc tactgctact accaagagga 360
ctggctcagt ggtggcaaaa tactggtgat gctccctaga gcaggaggcc cggaagtnnt 420
gacgcagcca tcagcctgcc aagattgttt tttaatcttc acagtgtttt aaagaacatg 480
ttaaaaaaaa aaaaantcta gtgctcctgc tgtcaagatt tctgtcatgg aaaccttgtt 540
t 541

<210> SEQ ID NO 3
<211> LENGTH: 361
<212> TYPE: DNA
<213> ORGANISM: Homo sapiens
<220> FEATURE:
<221> NAME/KEY: misc_feature
<222> LOCATION: (247)..(247)
<223> OTHER INFORMATION: n is a, c, g, t or u

<400> SEQUENCE: 3
actgacatta ttttaaacct aactgagatg atcagttaca ttcatcagtt ggtgagtttt 60
gaagaataac tacattttat ttcaaactaa caaatgtata cggttttagt tcagtgttga 120
agaattttaa tacaatatta aattacttga actgaacagt tccttgtata tattttgcct 180
attcactgtt gatatgtatg tagcaaaatg agagttaaat aacactaaaa tatggtacca 240
ggaggcnaat tgtataggag caaagttaat aggagctttg ctgaaacaga agcatatgtg 300
taaataagct tgggcttcca gttataaatt ttgtaatttt tgtcattatt tatatcctat 360
a 361

<210> SEQ ID NO 4
<211> LENGTH: 424
<212> TYPE: DNA
<213> ORGANISM: Homo sapiens

<400> SEQUENCE: 4
tggtgatgaa cagcggcctt cagacgcgag gctggggagg aatcgtcggg gtttttatta 60
tttttgccgt atttgctgtc ctgacagtag ccatccttct gatcatggag ggcctctctg 120
ctttcctgca cgccctgcga ctgcactggg ttgagttcca gaacaagttc tatgtcgggg 180
atggttacaa gttttctcca ttctccttta aacacatcct ggatggcaca gccgaggagt 240
aggctgaggg ctgcacctcc cacggtggtc accatgccaa tgaaggaagt tcagtcttgt 300
ctttgatatc agcccctgca aggcgctcaa tgggaaggtt gttcttggct cacctgaagc 360
atgaaactgt gtattatttg gacgtcagcc tgtggatttg atacgactta accacgtcag 420
agga 424

<210> SEQ ID NO 5
<211> LENGTH: 463
<212> TYPE: DNA
<213> ORGANISM: Homo sapiens

<400> SEQUENCE: 5
aaagcatcct gcagcgtgag cagctcctcc acctggagct ccgaagcatc ttctcaggcc 60
aaagcggcat tacccgtgaa tctgtcttct ccgccacagc atggtttgag gcgcagtctg 120

-continued

```
ttaatatagc tgggccatgt cagtgactgt tgtgtttgtg gggtcaggtg gggggcatgg    180

tatttgcaaa aaaaacaaat tatggctaat ttattatttt gttgcagtgg ggttaactgt    240

aaactcatgt aagagtctgt gatttcctca ttggttgatc tctctctctg taatcctcat    300

tgcaaatttt caccaggaca gcgttttttg attagagggg agctctggca cagtatgctt    360

taatttagca ggaacttcca gatgatttaa attctcgatg ctgtgatgac acacatatga    420

tctttcgtgt ttctgagcga ctctactttc attgtttgcc agc                      463


<210> SEQ ID NO 6
<211> LENGTH: 529
<212> TYPE: DNA
<213> ORGANISM: Homo sapiens
<220> FEATURE:
<221> NAME/KEY: misc_feature
<222> LOCATION: (38)..(38)
<223> OTHER INFORMATION: n is a, c, g, t or u
<220> FEATURE:
<221> NAME/KEY: misc_feature
<222> LOCATION: (203)..(203)
<223> OTHER INFORMATION: n is a, c, g, t or u

<400> SEQUENCE: 6

gcctcaccat tttgcgtttt ttagaaaccc attttctntg gtcatttata aagctgcttt     60

atagatatct ttgatcctgg catgccttgg tttcctctcc cttccctctt tccaatcctg    120

gtttcctaac ctcctcttgt agtaattctc aactcaactc aaagtcccaa gaatttggaa    180

tggtaggatg ctgtgcgggg agntcgaggc tgaggcataa tcactgcttc ggttctgctc    240

atcaggggac acgctccctt actcatggca gccatgtttg attgtcacag agccccccga    300

atactctgtc tatagtgaca cactgtaggt gtcataaatt ttaagaaacc tgcttttaag    360

tactatttat aggtttttct gttatacttg caacctagtt ttaaaataca tgaggatttt    420

atgaaagctt tatacagaca tttataggaa actcattctt tgattttagg tgccatttaa    480

attgataaca cttactttat aaaaagatgc tttttgtctg gatagagcc                529


<210> SEQ ID NO 7
<211> LENGTH: 421
<212> TYPE: DNA
<213> ORGANISM: Homo sapiens

<400> SEQUENCE: 7

gttacaagta ggctctcaga ggtacacttt tgggcaaagg tagatgtcca gtttcctctg     60

cccttgaggg gattatttgg aaataatttg ggattatttg gaaataattt gtgagaaccc    120

ttgctctgga gtgttttcca acttttaggc aatcacatac caccgctctc tattttttaa    180

aaccatggat tatcttcact attattaata atactttcct ttaaattgac tcatttttta    240

agcgtaaact tattttcaaa gacagcctta tattactcca taagtgaaaa accagcaccc    300

tcctgctgca aacagaaggg aagagacata agaataaaca tcatgaaaac aagataatat    360

taaataatct gacttagctt ctattgcctg ccagtgattc tgagcttaat gcctgcttgc    420

t                                                                    421


<210> SEQ ID NO 8
<211> LENGTH: 483
<212> TYPE: DNA
<213> ORGANISM: Homo sapiens

<400> SEQUENCE: 8

cacccaggcg acatcggtga cttcatcaat gagggactcc gcgctgctga caacgacccc     60
```

acggcacccc cctatgactc cctgctggtc ttcgactacg aggggagcgg ctccaccgca 120
ggctccgtca gctccctgaa ctcatccagt tccggggacc aagactacga ttacctcaac 180
gactggggcc ccagattcaa gaagctggcg gacatgtatg gaggtggtga agaggattga 240
ctgacctcgc atcttcggac cgaagtgaga gccgtgctcg gacgccggag gagcaggact 300
gagcagaggc ggccggtctt cccgactccc tgcggctgtg tccttagtgc tgttaggagg 360
ccccccaatc cccacgttga gctgtctagc atgagcaccc acccccacag cgccctgcac 420
ccggccgctg cccagcaccg cgctggctgg cactgaagga cagcaagagg cactctgtct 480
tca 483

<210> SEQ ID NO 9
<211> LENGTH: 491
<212> TYPE: DNA
<213> ORGANISM: Homo sapiens

<400> SEQUENCE: 9
cccatgtcac tggtcagcgt ggtttttatg tgtattagga ttgggggatg tgaagaaata 60
agtatccagt actttataac caaagcaatt aaatgatatt ggggtaggga atgttggcca 120
gttttgttta gttttgccat cacattgtca cccagacctc acctagcccc aagtaatcgg 180
gcgccccgaa gagggagaca gagatgtgcc agagttgacc cagtgtgcgg atgataacta 240
ctgacgaaag agtcatcgac ctcagttagt ggttggatgt agtcacatta gtttgcctct 300
ccccatcttt gtctccctgg caaggagaat atgcgggaca tgatgctaag agccctgggt 360
aaatgtggtg agaatgcacg cgtgcatatg ctacacatat gtgcttctca gttgcagaaa 420
atgaactgct ttgggagatt atcagtagaa agagtgttat catattggtg ctgagtgcta 480
tgtgtgctta t 491

<210> SEQ ID NO 10
<211> LENGTH: 484
<212> TYPE: DNA
<213> ORGANISM: Homo sapiens

<400> SEQUENCE: 10
tatgtgacgc tggacctttt ctttacccaa ggatttttaa aactcagatt taaaacaagg 60
ggttacttta catcctacta agaagtttaa gtaagtaagt ttcattctaa aatcagaggt 120
aaatagagtg cataaataat tttgttttaa tctttttgtt tttcttttag acacattagc 180
tctggagtga gtctgtcata atatttgaac aaaaattgag agctttattg ctgcatttta 240
agcataatta atttggacat tatttcgtgt tgtgttcttt ataaccaccg agtattaaac 300
tgtaaatcat aatgtaactg aagcataaac atcacatggc atgttttgtc attgttttca 360
ggtactgagt tcttacttga gtatcataat atattgtgtt ttaacaccaa cactgtaaca 420
tttacgaatt atttttttaa acttcagttt tactgcattt tcacaacata tcagacttca 480
ccaa 484

<210> SEQ ID NO 11
<211> LENGTH: 482
<212> TYPE: DNA
<213> ORGANISM: Homo sapiens

<400> SEQUENCE: 11
aatatgccac tacagctcgt aactccttta ttgtacttat catttttact atatgttttg 60

```
ttccctatca tgcctttcga ttcatctaca tttcttcaca gctaaatgta tcatcttgct    120

actggaaaga aattgttcac aaaaccaatg agatcatgct ggttctctca tctttcaata    180

gttgcttaga tccagtcatg tatttcctga tgtccagtaa cattcgcaaa ataatgtgcc    240

aacttctttt tagacgattt caaggtgaac caagtaggag tgaaagcact tcagaattta    300

aaccaggata ctccctgcat gatacatctg tggcagtgaa aatacagtct agttctaaaa    360

gtacttgagg taaacatact aaaatgaatt atataatgca gcctcttaat tctttgaaga    420

actaaaaaat taggaaacaa agttctagca tttacaaaac tcagatctca aagctctgct    480

tg                                                                   482


<210> SEQ ID NO 12
<211> LENGTH: 504
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u

<400> SEQUENCE: 12

ccacaggacc tcctgtagta gcccctgcgc tgtgtgtctg gagcgcggtc ctcggcctta     60

ttnaaatggt ccaagtagac agctgcttgt tggattccag tgcaggtacc tgcgatgttt    120

acgtccacac cgagcccagt gtgggactga catttctcaa tggaagtgaa atttgggatt    180

ggactttgaa gacggattac taaataataa ttattatatg taactgaagc aacctacttt    240

tgaaaatcaa ctgtattggg tagtgggagg tgggagggaa gggctttggg aaggggatga    300

atatctcttt ttacctttaa cagacttgtt taatcttctc gatgtagatg tttatgtagg    360

tacttcacat tgcaaacgcc ttttattcta tttacaagct cagatgtctc tgctctcctg    420

aatcttgggc atgcctttct gtaaccaaaa atccctgtag gcgtgctagc aattccaggg    480

tggtccgggt ttggcagatt tgat                                           504


<210> SEQ ID NO 13
<211> LENGTH: 538
<212> TYPE: DNA
<213> ORGANISM: Homo sapiens

<400> SEQUENCE: 13

attgacgcat atttaactcg ccctctatcc gtagagtagt catgacacta tacagatggt     60

tcgtgttcat actgcagctt aaaacaagca aaatacacag atgataatat gctaaatttt    120

cctctatcct gtacatttca caaaaaggca tatgcaatat ttacattttt aatttagttt    180

acagaatgga accaaaatgt ataaatgtta tgtttgctaa aacttcacaa tgtatattgg    240

gtctttgtac attttgcctg acttacctta aatttaaaat attttttgct atataaactt    300

taacagttat taaacagtgt tttccttttg ggtacgtatt gtttctggat atcaagatgt    360

taaatatatt tcttgctatt gtgatatgac aagagactta acttatcttg ctctgtcttc    420

cactgtacac gctgtatata ggggtcaatg tgatgctgct ggagacgaga ataaactgga    480

ctagaatagt gcattgtatt tagtctgtat tgatcatgga tgccctcctt aatagcca      538


<210> SEQ ID NO 14
<211> LENGTH: 459
<212> TYPE: DNA
<213> ORGANISM: Homo sapiens
<220> FEATURE:
<221> NAME/KEY: misc_feature
```

<222> LOCATION: (45)..(45)
<223> OTHER INFORMATION: n is a, c, g, t or u
<220> FEATURE:
<221> NAME/KEY: misc_feature
<222> LOCATION: (360)..(360)
<223> OTHER INFORMATION: n is a, c, g, t or u
<220> FEATURE:
<221> NAME/KEY: misc_feature
<222> LOCATION: (402)..(402)
<223> OTHER INFORMATION: n is a, c, g, t or u

<400> SEQUENCE: 14
agccctgatt ctaccactta aggtgatgta tgatcttagg ctggncactt ctctccctca 60
tccgttttcc tcttcaacat aatgaaatag acttgaaagt ctctaaggct ctatcagttc 120
tgacattcta ggcttcatat acattaagtt gagccatatg taatcactgt gtttgtaggt 180
tagaaacagc tgagtatcgt agtttcatat atggttccag ctaatacatg caatgtggct 240
ggtgaacact tctgaattca gaaactatcc cagatctcag ctagaaccat ccactgttct 300
gtttgtccag tttcaactta agggatctcc atgcggtccc tggaagtacc cattgaaacn 360
tgcgtatttg tgtatagcag aactctgaaa taatattctg anagcagtta tctctgagga 420
attgggttat aggtgatttt ccctttccgc atgataaat 459

<210> SEQ ID NO 15
<211> LENGTH: 302
<212> TYPE: DNA
<213> ORGANISM: Homo sapiens

<400> SEQUENCE: 15
cctccctatc gtctgaacag ttgtcttcct cagcctcctc ccgcccccac cttgggaatg 60
taaatacacc gtgactttga aagtttgtac ccctgtcctt ccctttacgc cactagtgtg 120
taggcagatg tctgagtccc taggtggttt ctaggattga tagcaattag ctttgatgaa 180
cccatcccag gaaaaataaa aacagacaaa aaaaaaggaa agattggttc tcccagcact 240
gctcagcagc cacagcctcc ctgtatgcct gtgcttggtc tactgataag ccctctacaa 300
aa 302

<210> SEQ ID NO 16
<211> LENGTH: 397
<212> TYPE: DNA
<213> ORGANISM: Homo sapiens

<400> SEQUENCE: 16
caggtgcacc actgaagtga ggacacaccg gagccaggcg cctgctcatg ttgaagtgcg 60
ctgttcacac ccgctccgga gagcacccca gcagcatcca gaagcagctg cagtgcaagc 120
ttgcatgcct gcgtgttgct gcaccaccct cctgtctgcc tcttcaaagt ctcctgtgac 180
attttttctt tggtcagagg ccaggaactg tgtcattcct taaagatacg tgccggggcc 240
aggtgtggct cacgcctgta atcccagcac tttgggaggc cgaggcggcg gatcacaaag 300
tcagacgaga ccatcctggc taacacggtg aaaccctgtc tctactaaaa atacaaaaaa 360
aaattagcta ggcgtagtgg ttggcaccta tagtccc 397

<210> SEQ ID NO 17
<211> LENGTH: 571
<212> TYPE: DNA
<213> ORGANISM: Homo sapiens

<400> SEQUENCE: 17

-continued

```
gtttcttcat tgatcaacca ggtttgggtt acacaaatca attgtggggg aaaaatcaaa     60

taaaacaatt gcttattata ttttccaaag gactgagcat ttatctttta ttcacgaaga    120

tatcatatga ggatgataat gatctttaac agatttttta gagatagaat ttataaagag    180

gctgatacta agaatactac aatcaaaatt gaagctagag aatgtaaaaa tagaaagtaa    240

atagttctaa gaatattctg gcataaatta tttttattta gccaataaaa tagcctccaa    300

atgtatatct cagacaccat agagctgcta acaatgagaa tcaaggaaga tgcttgcact    360

tagatttcgt ttgttgtatt tcagtagttc tggatgtcct ttgttaaaat tggaaaatgg    420

aaaaatgtct cgacagaaat gtcaatctgg tgattctgtg aactgtaaaa tgttcacttt    480

taaaaataaa gttgtaaaca agttactcat ataagttggt attacagtag caaaaacaga    540

aaaccatgtg atccatcctg tattttgatt g                                   571
```

<210> SEQ ID NO 18
<211> LENGTH: 469
<212> TYPE: DNA
<213> ORGANISM: Homo sapiens

<400> SEQUENCE: 18

```
catgcctgct ctcgaggcag cagtgggttc aggcccatca gctacccctg cagctgggga     60

agacttatgc catcccggca gcgaggctgg gctggccagc caccactgac tataccaact    120

gggcctctga tgttcttcca gtgaggcatc tctctgggat gcagaacttc cctccatcca    180

cccctctggc acctgggttg gtctaatcct agtttgctgt ggccttcccg gttgtgagag    240

cctgtgatcc ttagatgtgt ctcctgtttc agaccagccc caccatgcaa cttcctttga    300

ctttctgtgt accactggga tagaggaatc aagaggacaa tctagctctc catactttga    360

acaaccaaat gtgcattgaa tactctgaaa ccgaagggac tggatctgca ggtgggatga    420

gggagacaga ccacttttct atattgcagt gtgaatgctg ggcccctgc                469
```

<210> SEQ ID NO 19
<211> LENGTH: 383
<212> TYPE: DNA
<213> ORGANISM: Homo sapiens

<400> SEQUENCE: 19

```
gagcagcgta gacagctggt aaactgaaga gcacaactat attcttatga aggaatttgt     60

acctttgggg tattattttg tggcccgtga ccctcgttat tgttacagct gagtgtatgt    120

ttttgttctg tggagaatgc tatctggcat tatggtaata tattatttta ggtaatattt    180

gtactttaac atgttgcata atatatgctt atgtagcttt ccaggactaa cagataaatg    240

tgtaatgaac aaagatatgt tgtatgagtc gtcgtttctg tcagatttgt attgtttcca    300

agggaaaagc ttgggggagg actcagttca caaaatgcaa aactcaacga tcagattcac    360

ggacccagag cttttccatg tgt                                            383
```

<210> SEQ ID NO 20
<211> LENGTH: 480
<212> TYPE: DNA
<213> ORGANISM: Homo sapiens

<400> SEQUENCE: 20

```
gcttttacct gttattcttt gccctcaaat acagtattgt ggtcattttg atgatatgtg     60

tgtaaaatgt gaataatcca attggtgtct gtactcagcc ttttgatgtc tttttaggac    120

tttctcttct acacagcaat acgtcgtgct cgagtatcct tgtagcaaag cacatagagc    180
```

cagctgtcct gtcagttccc ctgtttgcct ctgaaacgtc tggttagtgg ggacccaaag 240
attctagtga gtcaacatcc ataactctgt atctagttgt attattcata gaaaatcaat 300
ctggtgctaa tggttggccc tggtgttgtt gggtggcagc tgctccttcg ccctcttgta 360
gtgtggctgt ggagggctct gcctatgggg ggtggcctgt ggcttgtatc cttcagtcca 420
ccacagcaaa tgtgtgtaga tttcatgctc gacacttacc actcacctat caacagatca 480

<210> SEQ ID NO 21
<211> LENGTH: 389
<212> TYPE: DNA
<213> ORGANISM: Homo sapiens

<400> SEQUENCE: 21
ccactgggcg cggccagata agtttttaag gttccttctt gctttagcat tctgagaaat 60
gtctaattgg tagtaagaca agagtaatag caacctgtat tgttagtatt taaccaaata 120
ggctaaaatt ttaatcaggt accttatgta ttaaatagaa atcggaatgt accataataa 180
atccaaactc tcaattacgc catggtaatt cagtcactaa aatatgtaaa gatagaaaat 240
tttttaattt aaagaagtgt gaaacatagc cattgattga tcagaattct ggaatctgaa 300
tattaaaacc ttacttagtg actggaatgg tatatgctcc ctccaaaagt ttatctttgt 360
ttattgatta aaggtaatcc ttactttct 389

<210> SEQ ID NO 22
<211> LENGTH: 497
<212> TYPE: DNA
<213> ORGANISM: Homo sapiens

<400> SEQUENCE: 22
gagtgatgct atggcttgct cgtgtcttat gatccaatcc ttttctacat cagcccttgt 60
tttgttttat ggctagtctt atctggcctg gttatttcct tgcggggagg agagggtttg 120
ctaatctgct cccagcccaa cctattacca ccccacctcg ctgggaccta ctgctcggga 180
ggcagcagac agggagccac cagcagtggc ttcctggccc tgtgctgggg gtggggggaa 240
gctgggggca catgtggccc ttgccttctg agcagctccc agtgccaggg ctttgagact 300
ttcccacatg ataaaagaaa agggaggtac agaagttcca attccctttt tattttgctg 360
gttggtatct gtaaatgttt aataaatatc tgagcatgta tctatcaacg ccaagaattt 420
caaagtctcc ttcaacaata tgaggctttt aggatgttta tattccttca tccctcttgt 480
ttcccaggtt ttgcagg 497

<210> SEQ ID NO 23
<211> LENGTH: 309
<212> TYPE: DNA
<213> ORGANISM: Homo sapiens

<400> SEQUENCE: 23
ccccagcagc aaacactcgc tgagtccacg tctggcttca ggtgggagga aatgtttcag 60
atgaaactta ctcaattcat accaccctga aatggaggac agaggtgaca aacttcagtt 120
taataggttt ctcaccaagt tgtatgttcc attggcccag gattcttgca ctaatgggtt 180
tctatcacat tatgtctata aatgggtgca ctttactgtt tgaatttgta actgaagtac 240
tggatattta agtgtgagta atgtcttcat tagaaaatag cagaaccgct cttgtctttt 300
agtgtattt 309

<210> SEQ ID NO 24
<211> LENGTH: 362
<212> TYPE: DNA
<213> ORGANISM: Homo sapiens

<400> SEQUENCE: 24

```
aatatgattt tgattcttcc tcctctttgc tgtcctttca agacacttgc tggaaaaagc     60
tttaatgcac ttagttttcc tttaggtttt ctatgactca gatgtaaagg actttctctg    120
tacagtatat tatccaatgc atgtttgttc tctctcctga tatattgaac accacacagt    180
tgtgaagccg tgcagtgggg atgccccaca ccccacagag gcatctaccc ctgtgtataa    240
ggaaagacat tttcctttgc tgtacttgct tgagcagttt tattgtctgt acatgtgagc    300
tgtgtgagat agatgtgaaa agttcaaatg aatgcatttt cctgccccat gtatacagat    360
tg                                                                   362
```

<210> SEQ ID NO 25
<211> LENGTH: 485
<212> TYPE: DNA
<213> ORGANISM: Homo sapiens

<400> SEQUENCE: 25

```
aggggcagtg gtggttttct gttctttctg gctatgcatt tgaaaatttt gatgttttaa     60
ggatgcttgt acataatgcg tgcataccac ttttgttctt ggtttgtaaa ttaactttta    120
taaactttac ctttttttata cataaacaag accacgtttc taaaggctac ctttgtattc    180
tctcctgtac ctcttgagcc ttgaactttg acctctgcag caataaagca gcgtttctat    240
gacacatgca aggtcatttt ttttaagaaa aaggatgcac agagttgtta catttttaag    300
tgctgcattt aaaagataca gttactcaga attctctagt ttgattaaat tcttgcaaag    360
tatccctact gtaatttgtg atacaatgct gtgccctaaa gtgtattttt ttactaatag    420
acaatttatt atgacacatc agcacgattt ctgtttaaat aatacaccac tacattctgt    480
taatc                                                                485
```

<210> SEQ ID NO 26
<211> LENGTH: 498
<212> TYPE: DNA
<213> ORGANISM: Homo sapiens

<400> SEQUENCE: 26

```
catcaaacat gttgggacaa tgcccatagg aatggacctc cttccccgtc tccagctggg     60
actggtgttt ttttagtctc tggagtatga tggttctcat gggtaggatg agatctttgg    120
cagaaaggtc ttcggtggtg ctctgagcct gcgctgcata ggactgagca gacccacctc    180
ctccagcttg ggtggccctg ccactcctgg ttccaagtct ctcctttcct ggcaggtctt    240
aagggaagat tgtacccctc accctttaca tacccagaat catcagtatg tcacttccta    300
atttctatca gtgtatctca ttatttcata ctgttttact aatcctaagt ctaaacagat    360
ttgctcaaaa ggagaccatt ctattttttta aagtacttag tgatacacgt ataagctttg    420
catggacgaa ttaaataagc acattgacct tttcttgtac attcagaacc tgaacatcca    480
tgtgaaaact gggtccat                                                  498
```

<210> SEQ ID NO 27
<211> LENGTH: 485
<212> TYPE: DNA
<213> ORGANISM: Homo sapiens

<400> SEQUENCE: 27 acccttaca tacccagaat catcagtatg tcacttccta atttctatca gtgtatctca 60
ttatttcata ctgttttact aatcctaagt ctaaacagat ttgctcaaaa ggagaccatt 120
ctatttttta aagtacttag tgatacacgt ataagctttg catggacgaa ttaaataagc 180
acattgacct tttcttgtac attcagaacc tgaacatcca tgtgaaaact gggtccattt 240
ttgagagatg tgaaactaca gtttatttgt aataaataaa tataatctat ccggtatatg 300
catatatcta tatgctgtgt taagtggtaa tgggtacatt acagtctgtg agagatggat 360
cgctccctct gtaaggaaca agacgttctc agctgatgtc acggtaggtt tagattctgt 420
agagtgttcc ccaacccgca ccgttctgta cctctcacac cactgcttgc ccgggcagta 480
gtggc 485

<210> SEQ ID NO 28
<211> LENGTH: 520
<212> TYPE: DNA
<213> ORGANISM: Homo sapiens

<400> SEQUENCE: 28
gaagcaagtt tccatgattt ctgaagagct ggtataggaa gtttctttct tccttttgtg 60
ttacatgtgc attaaacaga acaagctgtg tgtcatcaca gattgtactg tgggctcaga 120
aaccgtgaga gagcccccac cgtggacacc ggctctatgg ccacaggaaa aggaacgttt 180
ccaggcattt tgtctccagg gctcccgctg gacaggcacg tactgccccg gggagtaaat 240
gcggagagtt cacgaactgt gcccaacgca tgttatagcc agggtcctac taactactca 300
gtaaaagaac gtattgttgt attcctccag tgttaagcta tagccatgtt aaaagtcact 360
gtgcatttat tctcagcatc aaataccttg taacgtcttc tctgccttgt tagtgcatat 420
ttttactttt ctgatactgt aaagaatata tccagtatgt aaatgaatgt tctataaatc 480
ttttgtatag tcattttctc tgctccttaa atatcatctc 520

<210> SEQ ID NO 29
<211> LENGTH: 565
<212> TYPE: DNA
<213> ORGANISM: Homo sapiens

<400> SEQUENCE: 29
gtttagtagc ctcaattctc cattaattaa aagtgtgggc tgggcgtggg ggctcatgcc 60
tgtaatccca gcactttggg aggccgaggt gggcagatca cctgaggtca ggagttcaag 120
accagcctgg ccaacatggt gaaaccccgt ctctacaaaa atacaaaaat tagccaggcg 180
tgatggcagg tgcctgtaat cctagctact tggcaggcta acgcaggaga atcacttgac 240
cgggagacag aggttgcagt gagctgagat cgtacctatt gcactccatc ctggatgaaa 300
gagccagact ctgtctcaaa acaaacaaaa aagcgtgggg acttctgggg acagacaagg 360
tgcctgttat atatttactc agtctttgcc ctgaatggtc tcagcttgag accatttcaa 420
actggagaga agcaagccag ccaatagaat ggggtgattt acagggattt ctgtttactg 480
tcaaaatatt tctcatctgc actatgtttc catttgtggt cctgaaggaa attcttataa 540
ctcaacattt gtctggtctt ataag 565

<210> SEQ ID NO 30
<211> LENGTH: 401
<212> TYPE: DNA

<213> ORGANISM: Homo sapiens

<400> SEQUENCE: 30
gaacaattct aaaagccctg tgatttgaaa aatatagaat cattaatggc ccaagatagg 60
ccttcacacc ttcacaggtg cgaaaggaaa ggccttcaca ccctcacaga ggcatcatgc 120
aaaggacagc ggctttggct tttccaattt tccatcttta ggccctggtg agaggcacac 180
ttatgcacta aaatgcacat atatgcacat gcattcaaaa ataggcattt ggtacaatgg 240
tgatcttgta cctgatgggc tgaaaccagc ttaagaacaa atttgttctt cctgatatga 300
taactaggtc tccaagagaa aatagaaagg ctgctttagt gccttacgct tactaaattt 360
aaatctttat ttacctgggt ttgagcctac agtctattta t 401

<210> SEQ ID NO 31
<211> LENGTH: 518
<212> TYPE: DNA
<213> ORGANISM: Homo sapiens

<400> SEQUENCE: 31
gagaccatgg tctgtagacc ccttccccgat tctcctgtcc cagcttggaa ggcattgaaa 60
acagtctccg tttacacatc tcttcatacc acgtgtttga agtgttaaaa ttcaaaggga 120
tcattgaata aaacgggtgt agagtacagg aatggggcag acgcgattca ggtgaacagc 180
acaagaagaa tatgaggtgg ttcctaggag caacactttc gacctccagt tctccctgat 240
gacagtagct gtctccaaga gaaaaatcct cacttattaa ctctcttttc ttgcatctca 300
tttttataga gctactcatc cttatttgga aaaaccaaca acaaaaaagg cttttagaaa 360
atggttgtaa atctgacttc tttgcaagta actatgtata ttgtaaatag atataaaagg 420
ccttttttct aaataaggac ttaactgcct gtaacatgaa acttcaaact aaaccactaa 480
ctcaatgaac tacttatggt ttgtctgaca tccctcac 518

<210> SEQ ID NO 32
<211> LENGTH: 531
<212> TYPE: DNA
<213> ORGANISM: Homo sapiens

<400> SEQUENCE: 32
tatctttctg tgttccatgt aaatttattt accaacatct attgtcaaca tgtacatcta 60
ccttagtatg gtctgcattc tttttctgag agtacctcat agggctcctg cctgatcttt 120
gtagtttgtt cattcatcca tccacctgtt catttgttca tccatgtatt ctaacatttc 180
tatgtagtgt gcaactctaa tgtcatgctt ttgaagaaga gaatagctgc ccatagcagc 240
catccgtctg gataatagca aaacactcta gataagttat tttgcacttt cttatgtata 300
aagttggtag aaacttattt ttgctttgta tcatttaaat acattttgtt ttggtaaatg 360
aactgtgtat aaaatattta tgccgttaaa actgttttta gaaagtattt ttaatttcag 420
caagtttggt tacttgttgc atgactctta acacagctga ctttttgtgt cagtgcaatg 480
tatatttttt gtcctgttat taacttgtaa gccctagtaa tggccaatta t 531

<210> SEQ ID NO 33
<211> LENGTH: 459
<212> TYPE: DNA
<213> ORGANISM: Homo sapiens

<400> SEQUENCE: 33
gtggtttcca catgctctga gaagaggagc cctcatcttg aagggccagg agggtctatg 60
gggagaggaa ctccttggcc tagcccaccc tgctgccttc tgacggccct gcaatgtatc 120
ccttctcaca gcacatgctg gccagcctgg ggcctggcag ggaggtcagg ccctggaact 180
ctatctgggc ctgggctagg ggacatcaga ggttctttga gggactgcct ctgccacact 240
ctgacgcaaa accactttcc ttttctattc cttctggcct ttcctctctc ctgtttccct 300
tcccttccac tgcctctgcc ttagaggacc cacggctaag aggctgctga aaaccatctg 360
gcctggcctg gccctgccct gaggaaggag gggaagctgc agcttgggag agcccctggg 420
gcctagactc tgtaacatca ctatccatgc accaaacta 459

<210> SEQ ID NO 34
<211> LENGTH: 380
<212> TYPE: DNA
<213> ORGANISM: Homo sapiens

<400> SEQUENCE: 34
aaaaggtact agttctgcat ttcagagttg gcttgttgaa ccaggctata tgcttccaag 60
atttaaatgt ttttctgtat tatactctca attgtgtttt aaaaaaatct cttacagaaa 120
tctctacctc aggcactaag tgttatgaca tgggtagcat attgatattg aaaacttagc 180
taggacttcc agccttttaa gataatttaa atgtaaaatt aaatggttaa ccagcaatct 240
aatgtcatgt ggtgtgcagt ttggatattg catgaacagc taaggaatca cctgttctag 300
tgccaaagat cactcattgc taattttgtt ctgtacagct tatgtaatat tttcatggtg 360
gagacggact ctgtgtgctc 380

<210> SEQ ID NO 35
<211> LENGTH: 286
<212> TYPE: DNA
<213> ORGANISM: Homo sapiens
<220> FEATURE:
<221> NAME/KEY: misc_feature
<222> LOCATION: (63)..(63)
<223> OTHER INFORMATION: n is a, c, g, t or u
<220> FEATURE:
<221> NAME/KEY: misc_feature
<222> LOCATION: (121)..(121)
<223> OTHER INFORMATION: n is a, c, g, t or u

<400> SEQUENCE: 35
ttaatttctg tgaagagtgc ccctggtgtt tcatcttggc ctgttttgat gagaatgtta 60
tcntttgtgt ctggataacg cgtcagcttc ttaaagtaca tataaagata ttctgtcacc 120
nccccacatg cacacacttt taaaatctat ttttattctc ttgctaaagt tgtaattatg 180
tcaagaattt tccagctcta actgccttct tagtacatgt ctttctgcct ttgaagcata 240
tgagtttgcc aaagtcattc tcccctaatg acatattgtg gactta 286

<210> SEQ ID NO 36
<211> LENGTH: 486
<212> TYPE: DNA
<213> ORGANISM: Homo sapiens

<400> SEQUENCE: 36
gcactggcag cgaggctcgt gtgtccccca ggcagatctg ggcactttcc caacccaggt 60
ttatgcgtct ccagggaagc ctcggtgcca gagtggtggg cagatctgac catccccaca 120
gaccagaaac aaggaatttc tgggattacc cagtccccct tcaacccagt tgatgtaacc 180
acctcatttt ttacaaatac agaatctatt ctactcaggc tatgggcctc gtcctcactc 240

-continued

```
agttattgcg agtgttgctg tccgcatgct ccgggcccca cgtggctcct gtgctctaga    300

tcatggtgac tcccccgccc tgtggttgga atcgatgcca cggattgcag gccaaatttc    360

agatcgtgtt tccaaacacc cttgctgtgc cctttaatgg gattgaaagc acttttacca    420

catggagaaa tatattttta atttgtgatg cttttctaca aggtccacta ttcctgagtt    480

taatgt                                                               486


<210> SEQ ID NO 37
<211> LENGTH: 521
<212> TYPE: DNA
<213> ORGANISM: Homo sapiens
<220> FEATURE:
<221> NAME/KEY: misc_feature
<222> LOCATION: (96)..(96)
<223> OTHER INFORMATION: n is a, c, g, t or u
<220> FEATURE:
<221> NAME/KEY: misc_feature
<222> LOCATION: (102)..(102)
<223> OTHER INFORMATION: n is a, c, g, t or u
<220> FEATURE:
<221> NAME/KEY: misc_feature
<222> LOCATION: (354)..(354)
<223> OTHER INFORMATION: n is a, c, g, t or u

<400> SEQUENCE: 37

gagtccaaat gtcatcagtg ctcattttga gataccctgc tatcgatggt cgctacaaac     60

caggaaatac tcaagttatt atgtgtatac attggnttta gntttatgaa acaatttacc    120

ttcatgatct catagttaaa attgtaataa atttaggaat ataaaggatc aatatgggaa    180

gcaaaatttc taaaggcagt ttctgttgtt ttaattagta tttgtgtagt tcaaaccagg    240

aaggatttga ctatcattag attttgctta actttatgaa agctaaaata ttctctgtta    300

taaaggggca actccatctg gtcctatagc atctttacta ctgatttttt tttngtttaa    360

tttgaaaatg caaagaattg ttaaatgttc ttaaatgttc tcactacaaa aaaagaaaaa    420

agataactac gtgaggtgat ggatatgtta attagctgga ttgtggtaat cattttggaa    480

tgtatatgta tatcaaaaca tgtagtacac cctaaatata t                        521


<210> SEQ ID NO 38
<211> LENGTH: 518
<212> TYPE: DNA
<213> ORGANISM: Homo sapiens
<220> FEATURE:
<221> NAME/KEY: misc_feature
<222> LOCATION: (102)..(102)
<223> OTHER INFORMATION: n is a, c, g, t or u
<220> FEATURE:
<221> NAME/KEY: misc_feature
<222> LOCATION: (360)..(360)
<223> OTHER INFORMATION: n is a, c, g, t or u

<400> SEQUENCE: 38

caggcgaggg ccaatgttgt gtttcttacc ccctctggaa tgccaaaggc aaggtactag     60

gtgacctcct ggtccccaag aaaatgtgat ttattctgag gncgaacagc caagggagga    120

ctagtctgga gcacgctcgg ccgtcctggc aggagctgag cctcaggtgt ctggcggtgc    180

cccagcagcc ctggattcac ccaacaccag aatcccactt ttctaaatcc acctgttgtt    240

ctgagcacct ctgaacccgc agcttcggca aaaggagtct gtaccaagct gcttctggat    300

gaccaacact ggagactctg gccttaccat gtggaaatca ttttcctgaa gtctggaacn    360

aattttgaga agttttttttc tcaacacttt tgtgtttcta acactgtatc ttgactgtgt    420

aaataccaac aaggctgtaa ataaatgcag atgtagatac cttctagaaa aaaaaaagca    480
```

taaaaacaaa accagaagtg atcccgtgta gccttcgt 518

<210> SEQ ID NO 39
<211> LENGTH: 462
<212> TYPE: DNA
<213> ORGANISM: Homo sapiens
<220> FEATURE:
<221> NAME/KEY: misc_feature
<222> LOCATION: (177)..(177)
<223> OTHER INFORMATION: n is a, c, g, t or u

<400> SEQUENCE: 39
gaggacagca aacctttca gcacttctct cagagcaaat ggaaacacac agtaagtagc 60
tttctgacta cattattttc tggtcacttt taaagaaagt ttacaacctg ttctgaaact 120
atttgtcttt tcactggttg taagtgtacc ccaatctcag ggagtatatc tgtagtncca 180
caggcaaaag atccactcct tcccacactc atttgcctga acttactcga agggctgcat 240
ttctctgagt ttacgaaatt gtgtcattat ggtccccata cagtggtatt taacttttaa 300
agcaactttt aagaaaactc gacttgtttt ttgttcattt taagtgtgtg gtactaaaaa 360
gacatgttag actttttta aaaaagcact tatgttttga aaatagaata aataataaga 420
atttccaatt aaatcatgtc tggtgccaat gtgcaaaact tc 462

<210> SEQ ID NO 40
<211> LENGTH: 470
<212> TYPE: DNA
<213> ORGANISM: Homo sapiens

<400> SEQUENCE: 40
gtgaacagct tggccttttt tgggtgtctt gacaggccaa gaagaacaaa tgactcagaa 60
ccggattaac atgaaagtta tccaggcgca gagttgaaga agcataagca agcaagacaa 120
aaacagagag accgcaagga ggaagatctg tggtactgtc ataaaaaaca gtggagctct 180
gtattagaaa agcccctcag aactgggaag gccaggtaac tctagttaca cagaaactgg 240
tactaaagtc tatcaaactg attacacaga ctgtaagaat tcaaagtcaa ctgacatcta 300
tgctacatat attatatagt ttgtacttga ctatgagcca ttaacttaaa gcatatgttt 360
caaatagcca ttgctactat tccttgtccg gtgtaatttt attttattgt ttttactttg 420
gaagagatga actgtgtatt taacttaagc tattgctctt aaaaccaggg 470

<210> SEQ ID NO 41
<211> LENGTH: 298
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (45)..(45)
<223> OTHER INFORMATION: n is a, c, g, t or u
<220> FEATURE:
<221> NAME/KEY: misc_feature
<222> LOCATION: (47)..(53)
<223> OTHER INFORMATION: n is a, c, g, t or u
<220> FEATURE:
<221> NAME/KEY: misc_feature
<222> LOCATION: (55)..(55)
<223> OTHER INFORMATION: n is a, c, g, t or u
<220> FEATURE:
<221> NAME/KEY: misc_feature
<222> LOCATION: (57)..(60)

<223> OTHER INFORMATION: n is a, c, g, t or u
<220> FEATURE:
<221> NAME/KEY: misc_feature
<222> LOCATION: (64)..(83)
<223> OTHER INFORMATION: n is a, c, g, t or u
<220> FEATURE:
<221> NAME/KEY: misc_feature
<222> LOCATION: (85)..(85)
<223> OTHER INFORMATION: n is a, c, g, t or u

<400> SEQUENCE: 41
accctctcct tgagtttctg tgaattaaaa tatttgcaaa tncanannnn nnnanannnn 60
aaannnnnnn nnnnnnnnnn nnncnactga tgctgggagc caaatgctgg tgctttgaga 120
gtcccggagg ccccggggtt cccgccccgc tggtgtgtat atgtgtgtct gtgtgagtgt 180
gtgtgtgagt acagatgtga gaaggtggtc acacacagat gggtaagccc actgatctac 240
ttgtagtcac tcagtgtaat cattaggcta tcttcaagga atcattgtgc agtcaaaa 298

<210> SEQ ID NO 42
<211> LENGTH: 407
<212> TYPE: DNA
<213> ORGANISM: Homo sapiens
<220> FEATURE:
<221> NAME/KEY: misc_feature
<222> LOCATION: (238)..(238)
<223> OTHER INFORMATION: n is a, c, g, t or u

<400> SEQUENCE: 42
gtccaagaac tcaagtcact ttacatctat taactgcttt ggagacttca taatttttct 60
aggaaaggtg ttagtggtgt gtttcactgt ttttggagga ctcatggctt ttaactacaa 120
tcgggcattc caggtgtggg cagtccctct gttattggta gctttttttg cctacttagt 180
agcccatagt tttttatctg tgtttgaaac tgtgctggat gcacttttcc tgtgtttngc 240
tgttgatctg gaaacaaatg atggatcgtc agaaaagccc tactttatgg atcaagaatt 300
tctgagtttc gtaaaaagga gcaacaaatt aaacaatgca agggcacagc aggacaagca 360
ctcattaagg aatgaggagg gaacagaact ccaggccatt gtgagat 407

<210> SEQ ID NO 43
<211> LENGTH: 375
<212> TYPE: DNA
<213> ORGANISM: Homo sapiens

<400> SEQUENCE: 43
agggtaactt ccagtgtcac aatgagcagt tctgtaagtg ggtgcctctc agcacatttc 60
tatgaatata ttatgtagat aggctgtatt gattttggta gcattgacac cttcttaggc 120
aattagttga agaaaactgc aaaatatttt cttatgtaat agctgtatag agcaatagca 180
atcaaagcat gagaaggcac taacgctggg atgaaagatg agattcagag gtgactgaga 240
atcatgtgag tgatggctgt atattttgtg taaaatatat gtgtgaaaat gaactaagag 300
tgagttactc agcactctca agaattatgc agattctgca tttttcttat gccgtgtgcc 360
taaaaaccta cttga 375

<210> SEQ ID NO 44
<211> LENGTH: 527
<212> TYPE: DNA
<213> ORGANISM: Homo sapiens

<400> SEQUENCE: 44
gggtggttct ggccaggaag gcacaaggta gctgtgggcc aagacaccag ccctgtccta 60
gcccttcagt aagaccttgc caggagagga gaaggatgcc tgggtgccag gcaagacaag 120
cccctcagca ggagagaggc ccagaggctc cagctggcca ccgtgcccca caagatggcc 180
cctgtgtggt tccctttacc ttggcttcct ggcccagtcc ctgcctctcc acctgcaccc 240
tgcttcctgg cccagtccca ggttggagtc cctctgcata gctgactact catgcattgc 300
tcaaagctgg cttttcacat taagtcaaca ccaaacgtgg ttgccacatt tcatcagaca 360
gacacctccc tctggagatg cagttgagtg acaaccttgt tacattgtag cctagaccaa 420
ttctgtgtgg atatttaagt gaacatgttt acaatttttg tatatatcac tctctccctc 480
tcctgaaaga ccagagattg tgtattttca gtgtcccatg ttccgac 527

<210> SEQ ID NO 45
<211> LENGTH: 518
<212> TYPE: DNA
<213> ORGANISM: Homo sapiens

<400> SEQUENCE: 45
gtgccatagt gcaggcttgg ggagctttaa gcctcagtta tataacccac gaaaaacaga 60
gcctcctaga tgtaacattc ctgatcaagg tacaattctt taaaattcac taatgattga 120
ggtccatatt tagtggtact ctgaaattgg tcactttcct attacacgga gtgtgctaaa 180
actaaaaagc attttgaaac atacagaatg ttctattgtc attgggaaat ttttctttct 240
aacccagtgg aggttagaaa gaagttatat tctggtagca aattaacttt acatcctttt 300
tcctacttgt tatggttgtt tggaccgata agtgtgctta atcctgaggc aaagtagtga 360
atatgtttta tatgttatga agaaaagaat tgttgtaagt ttttgattct actcttatat 420
gctggactgc attcacacat ggcatgaaat aagtcaggtt ctttacaaat ggtattttga 480
tagatactgg attgtgtttg tgccatattt gtgccatt 518

<210> SEQ ID NO 46
<211> LENGTH: 233
<212> TYPE: DNA
<213> ORGANISM: Homo sapiens

<400> SEQUENCE: 46
gccatcacag ttgcgattcc atgagtagct gctttatgac tgctttttgt actatctgga 60
tgtgcccaga gttacttctg tacaagctct gtatctatgt ccgttgagaa cattatttta 120
acaagaagaa caccaacagt agcatgaaat ataatactgt tttataattc taaagctgct 180
gttaatttat gaagtacata ataatctaat gtaaactgca gaagtcagag caa 233

<210> SEQ ID NO 47
<211> LENGTH: 548
<212> TYPE: DNA
<213> ORGANISM: Homo sapiens

<400> SEQUENCE: 47
agggtgccaa gagatgcctt tctgaagttg gccacttctt gaagattcaa atatttatct 60
ctttatttag acatggttgc ctgcaggtat ttcactgttt actgttgtta gagatatagg 120
cactggggca gctgaggaac ctcaatatgt taagagcctt ggctttggta gcctcctggc 180
aggagcagca gtttgccaca ggtccggacc tctccctcca cacagccaca ctgcctcatg 240
cagtctgacc cacccagtga gggtgcattt gaacactgat tatattctcc atttgttttt 300
aagctctgct ttgtgttaga gcttgtgact gccaaaaatt ttgtgcacag tgatatgact 360

-continued

```
gttttaggat cttaagggta gaattttgtg aaaggtgaga tcctttggaa ttgagttctt    420

tctcattggg tatgaaaatg gatgtatgtt tagaatatat gcccaacgag gcaggaccat    480

gtggatagat tccatttgtt tccttgacct gatgtaataa aaactgataa aagccgtgca    540

gtgcccgg                                                             548


<210> SEQ ID NO 48
<211> LENGTH: 352
<212> TYPE: DNA
<213> ORGANISM: Homo sapiens

<400> SEQUENCE: 48

atgaaatatg ccagatctat agtattttaa tgtgcatcta ctttaaatga gtcatcttgg     60

ggtttttata attcccttat gttcttgccc ctctacactt gaaataacaa aatgccttaa    120

ttttatggat tagttctctt atagtagaca ggcagctata tgcagcaaaa ccaataaagt    180

tatttttcaa ctttcatagt tgtaaaatat cttataacag aatacaaaac agctaagaaa    240

acatgccaca ttttatttta gcattttcaa ataatttgtt tttggtgtaa gcacaggata    300

aaaaaggaga gcgtcaaaga aaagagacat aacacctaac attcataaaa at            352


<210> SEQ ID NO 49
<211> LENGTH: 488
<212> TYPE: DNA
<213> ORGANISM: Homo sapiens

<400> SEQUENCE: 49

ataggttata ctttgctgac gattcacatt ttattagttt ggttatgttt tgtcctttta     60

aaacattttc ttttgagatg gggtcttgc tctgttgccc acgcaggagt gcagtggcat    120

gctctcagct cactgcagcc ctgactgcct aggctccagc aatcttctta cgtcagcctc    180

cagagtagct gggaccgcag gcacttgcca ccacgcccca ctaaaaattt tttaaattgt    240

tgcctttctt gaagtgttct ctgcctgtct ttgtcacaaa atttcatttt tctcatagtt    300

aatttcatct ctccggtaag attttattgg tgtttctttt ataactttgc agttcttaca    360

ccgtttggtg attttcatgt ttcttagaaa ctttaaacct ttaacttcaa acattaaaat    420

acaagtcttt taagtacatg agtgcttaga aatgtacata atgtttatat acacttatgc    480

cttacatt                                                             488


<210> SEQ ID NO 50
<211> LENGTH: 297
<212> TYPE: DNA
<213> ORGANISM: Homo sapiens
<220> FEATURE:
<221> NAME/KEY: misc_feature
<222> LOCATION: (117)..(118)
<223> OTHER INFORMATION: n is a, c, g, t or u
<220> FEATURE:
<221> NAME/KEY: misc_feature
<222> LOCATION: (120)..(120)
<223> OTHER INFORMATION: n is a, c, g, t or u
<220> FEATURE:
<221> NAME/KEY: misc_feature
<222> LOCATION: (122)..(122)
<223> OTHER INFORMATION: n is a, c, g, t or u
<220> FEATURE:
<221> NAME/KEY: misc_feature
<222> LOCATION: (165)..(165)
<223> OTHER INFORMATION: n is a, c, g, t or u
<220> FEATURE:
<221> NAME/KEY: misc_feature
<222> LOCATION: (177)..(177)
<223> OTHER INFORMATION: n is a, c, g, t or u
```

<220> FEATURE:
<221> NAME/KEY: misc_feature
<222> LOCATION: (193)..(193)
<223> OTHER INFORMATION: n is a, c, g, t or u
<220> FEATURE:
<221> NAME/KEY: misc_feature
<222> LOCATION: (240)..(241)
<223> OTHER INFORMATION: n is a, c, g, t or u
<220> FEATURE:
<221> NAME/KEY: misc_feature
<222> LOCATION: (254)..(254)
<223> OTHER INFORMATION: n is a, c, g, t or u
<220> FEATURE:
<221> NAME/KEY: misc_feature
<222> LOCATION: (256)..(260)
<223> OTHER INFORMATION: n is a, c, g, t or u

<400> SEQUENCE: 50
caccaagtta cgtcaaagtc tcaggagcag ctccggtctc catagaggct gggtcagcag 60
tgggcaaaac aacttccttt gctgggagct ctgcttcctc ctacagcccc tcggaanncn 120
cnctcaagaa cttcacccct tcagagacac cgaccatgga catcncaacc aaggggncct 180
tccccaccag canggaccct cttccttctg tccctccgac tacaaccaac agcagccgan 240
ngacgaacag cacntnnnnn aagatcacaa cctcagcgaa gaccacgatg aagcccc 297

<210> SEQ ID NO 51
<211> LENGTH: 539
<212> TYPE: DNA
<213> ORGANISM: Homo sapiens

<400> SEQUENCE: 51
gttgatggcg aatttctgca ttacatttcc ccccttcagt tcctggattc tcctgagtgg 60
gattcactga gacccacaga ggaaggcatt tttcaggtaa ccctcactgc agaaactgat 120
tgtcgatatg tgtcttggag gagaaagaaa ttatatctgc tctttgctca gcatcgctac 180
atctcccgcc ttttttcagt gctaattggc agtgacattg cagataaact ctatgccttg 240
aatgacaggg tatatatagg aaaaagatat cactatgata ttcggctacc caacttctat 300
caaatgtcaa ctccagaaat acgcagatca cccctgacac aacattttca gaattccaga 360
cgatactgtg ataaatgaca tcaaagtctg aaatttataa gtataaaaaa agactctctc 420
ttcatcattc cccagtgaaa tagcaaaata caaaaaaaga gctccctaat gtttttataa 480
atcaaattca gaagcgagat gccattgcca actgttttat tcctttcaac aactgcatt 539

<210> SEQ ID NO 52
<211> LENGTH: 520
<212> TYPE: DNA
<213> ORGANISM: Homo sapiens

<400> SEQUENCE: 52
aactttgtat agcccatgta cctaccttgt atagaaaaat aattttaaaa atttgaatgg 60
aagggggtaa aggaagtcat gaagtttttt tgcattttta tttaaatgaa ggaattccaa 120
ataactcacc tacagatttt tagcacaaaa atagccattg taaagtgtta aaatttacga 180
taagtattct attggggagg aaaggtaact ctgatctcag ttacagtttt tttttccttt 240
ttaatttcat tattttgggt ttttggtttt tgcagtccta tttatctgca gtcgtattaa 300
gtcctattgc tagaataggt tactacaaaa aaggttatat tctgaaagaa aaataactga 360
cattatatat aaccaattaa tttaaagtat tgccatttaa attacacact gagagcatgt 420
cctatgcaga catagatttt tctgttcatt tatttttctt cattgcagtg gattgatttg 480

-continued

```
ataaatagat gtgttgaatt actacatttg ctgtacatat                        520


<210> SEQ ID NO 53
<211> LENGTH: 577
<212> TYPE: DNA
<213> ORGANISM: Homo sapiens

<400> SEQUENCE: 53

tgccactaat tcattcacac taaggtgtaa atgattgata ataggaatga gttacctctt     60

cccacagaca tttgttttta agtatgacag agcagggcct taatcccaag ggaaaaggtt    120

atggaactgg agggggtgag ctttctgggt agaaggagac ttcctgaatt tccttaaaac    180

ccagtaagag taagacctgt tgttttggaa ggtctgctcc accatctaag agcactgttt    240

tttttttttt gttgttgttg ttgttttacg gtctctgagg gaatatagta aaaatgcata    300

tgcacgtgca atttgcacgg cagcatttca ccgattgtgg actgtattgg ctaatgtgtt    360

tcctggtctt tagatgcaaa ccattaataa cactatctta tctcatagtt ttttcagggg    420

tgcttcttga ttagtaggga atttgaaca cctctttaaa tacagctaga aaataaaacc     480

aatttgtaaa gccacatttg catatgatgc cagcctcacg catttgtata tctccagaaa    540

ttcaggtatg cctcaccaat ttgcccgtct ttaataa                           577


<210> SEQ ID NO 54
<211> LENGTH: 539
<212> TYPE: DNA
<213> ORGANISM: Homo sapiens
<220> FEATURE:
<221> NAME/KEY: misc_feature
<222> LOCATION: (179)..(179)
<223> OTHER INFORMATION: n is a, c, g, t or u

<400> SEQUENCE: 54

agggcatgtt aacagtatac cagtaacagc actttatctc atttatatga acacctttga     60

ggtgctactt aagtccaagc tctgatgtat tattcatttg taaagataag gtacaggaat    120

gaaccttggt ttaaaggtat ttttatatga aaatggtgtg ttattggaag atgttaaant    180

gctaatttga gagaagtagg agtgtatctg ttttatatgt tgggatgtga aatttatttt    240

ctaaaattga ggagaaggaa gttatatatt tgcagaatgt tttaaagtga attgttgtaa    300

tgaagttcct gtgaacatca ttatggtttt gtacaaatag gaacctctga tgtcattctt    360

caacgtttgt tcctgtgtgt acaattgtac tttgtatgaa cagctttatc atttttatag    420

gctttccatg agttttgctg taactactat ggcttattta ttttctttaa tatttgtgaa    480

agtcttactc ctttgttagt tttgtttctg cacaactact gtacttttcc atatggaat     539


<210> SEQ ID NO 55
<211> LENGTH: 480
<212> TYPE: DNA
<213> ORGANISM: Homo sapiens
<220> FEATURE:
<221> NAME/KEY: misc_feature
<222> LOCATION: (45)..(45)
<223> OTHER INFORMATION: n is a, c, g, t or u
<220> FEATURE:
<221> NAME/KEY: misc_feature
<222> LOCATION: (133)..(133)
<223> OTHER INFORMATION: n is a, c, g, t or u

<400> SEQUENCE: 55

aacggaatac ctgctaggtt ccaggaatga gctcacctaa caganagcaa atgtgtctgg     60

ttagatctca gcagagccca ttctgcaaga cctggctgag ccagatgaga gggtgggccc    120
```

tgtgctgggg ggnccttggg tcacacacag gaaccgagac ctggcttcca ccccccagtc 180
acccacttgg gttatctgct ggaagttatc gataggactg tgtggccaac caagtgcttg 240
tgagatcact gacactgcaa aaacaaagca aactgctccg ggtaccagga cttcctccaa 300
cctggcaagg gtgtgcgctg aggcggggct tgcaggtgag ggggctgtat gcttcaggaa 360
ctaactaaat gcatgcagaa ggtaagaggc atgatgggag gtgttcaagc acagcaatcc 420
catttgggag ttattttgat actgcgatga gtaagggtaa gggcgcatgg aatggggcta 480

<210> SEQ ID NO 56
<211> LENGTH: 273
<212> TYPE: DNA
<213> ORGANISM: Homo sapiens
<220> FEATURE:
<221> NAME/KEY: misc_feature
<222> LOCATION: (163)..(163)
<223> OTHER INFORMATION: n is a, c, g, t or u
<220> FEATURE:
<221> NAME/KEY: misc_feature
<222> LOCATION: (197)..(197)
<223> OTHER INFORMATION: n is a, c, g, t or u

<400> SEQUENCE: 56
tactatatat tgtactgatg ccaaaagtca tgttttcatc cacttagtga aaaaatagta 60
aaattaagtc ggaagaaatt gcttaaaatt ttgtaatttg tatttataag ccccaaatgc 120
atcaaatgca gtaggagaac aatgtaatac agcttggtac ctnaaaaata tagctaagtt 180
ggtttttgaa tataaancag tttatgaata tgtgcatttt ctgtattgtt atgatttgac 240
tttttagagt ctatgccaaa atatatggct gta 273

<210> SEQ ID NO 57
<211> LENGTH: 544
<212> TYPE: DNA
<213> ORGANISM: Homo sapiens

<400> SEQUENCE: 57
ggagtttgca ttcttattca tcagggagga aagtttcttt gaaaatagtt attcagttat 60
aagtaataca ggattatttt gattatatac ttgttgttta atgtttaaaa tttcttagaa 120
aacaatggaa tgagaattta agcctcaaat ttgaacatgt ggcttgaatt aagaagaaaa 180
ttatggcata tattaaaagc aggcttctat gaaagactca aaaagctgcc tgggaggcag 240
atggaacttg agcctgtcaa gaggcaaagg aatccatgta gtagatatcc tctgcttaaa 300
aactcactac ggaggagaat taagtcctac ttttaaagaa tttctttata aaatttactg 360
tctaagatta atagcattcg aagatcccca gacttcatag aatactcagg gaaagcattt 420
aaagggtgat gtacacatgt atcctttcac acatttgcct tgacaaactt ctttcactca 480
catctttttc actgactttt tttgtggggg cggggccggg gggactctgg tatctaattc 540
ttta 544

<210> SEQ ID NO 58
<211> LENGTH: 507
<212> TYPE: DNA
<213> ORGANISM: Homo sapiens

<400> SEQUENCE: 58
tgtcaagatg cttctggcca tggtccttac ctctgccctg ctcctgtgct ccgtggcagg 60
ccaggggtgt ccaaccttgg cggggatcct ggacatcaac ttcctcatca acaagatgca 120

-continued

```
ggaagatcca gcttccaagt gccactgcag tgctaatgtg accagttgtc tctgtttggg    180

cattccctct gacaactgca ccagaccatg cttcagtgag agactgtctc agatgaccaa    240

taccaccatg caaacaagat acccactgat tttcagtcgg gtgaaaaaat cagttgaagt    300

actaaagaac aacaagtgtc catatttttc ctgtgaacag ccatgcaacc aaaccacggc    360

aggcaacgcg ctgacatttc tgaagagtct tctggaaatt ttccagaaag aaaagatgag    420

agggatgaga ggcaagatat gaagatgaaa tattatttat cctatttatt aaatttaaaa    480

agctttctct ttaagttgct acaattt                                        507
```

<210> SEQ ID NO 59
<211> LENGTH: 533
<212> TYPE: DNA
<213> ORGANISM: Homo sapiens

<400> SEQUENCE: 59

```
gaagatgggc gaggcaaaat catgccaaac agctttatca tgatgttcaa gaccaagaat     60

cagaagctcc tggatgcctt aaaaaataag caatgttaac agtgaactgt gtccatttaa    120

gctgtattct gccattgcct ttgaaagatc tatgttctct cagtagaaaa aaaaatactt    180

ataaaattac atattctgaa agaggattcc gaaagatggg actggttgac tcttcacatg    240

atggaggtat gaggcctccg agatagctga gggaagttct ttgcctgctg tcagaggagc    300

agctatctga ttggaaacct cccgacttag tgcggtgata ggaagctaaa agtgtcaagc    360

gttgacagct tggaagcgtt tatttataca tctctgtaaa aggatatttt agaattgagt    420

tgtgtgaaga tgtcaaaaaa agattttaga agtgcaatat ttatagtgtt atttgtttca    480

ccttcaagcc tttgccctga ggtgttacaa tcttgtcttg cgttttctaa atc           533
```

<210> SEQ ID NO 60
<211> LENGTH: 537
<212> TYPE: DNA
<213> ORGANISM: Homo sapiens
<220> FEATURE:
<221> NAME/KEY: misc_feature
<222> LOCATION: (209)..(209)
<223> OTHER INFORMATION: n is a, c, g, t or u

<400> SEQUENCE: 60

```
gcccggaagt cggccaggaa gttggccaat cagaagcggt tcagtgagtt tatgaggcaa     60

tacttggtcc tgagcatgca gtccagccag cgccggcgca ccctgcacca gaatggtaat    120

gtgtagccgg aaggggcgct cctcccagct gtaccggcca ctgcaaccca tgagcgtcca    180

ggtgatcccc caaacagcat gtgctcagnc ccagacctgc cgcctgggaa tcaggattcc    240

ttcttcccca aggcactgag cgcctgcaga tcccgcaggc ttcgtttgcc tccagaacct    300

tcccgtctga ttgttcctcc ccagcccccct ggcatgtttc accacaaccc tgttgctaca    360

tcagagtgta tttttgtaat tcctctagct accatttcaa tagccccatc tctcctgctc    420

acccgcctct tgccccttct aggggcaggt gaaaggaata ggaaattgaa cctggggttt    480

tgacttgcca ctgccataac ttgtttgtaa aagagctgtt ctttttgact gattgtt       537
```

<210> SEQ ID NO 61
<211> LENGTH: 557
<212> TYPE: DNA
<213> ORGANISM: Homo sapiens
<220> FEATURE:
<221> NAME/KEY: misc_feature
<222> LOCATION: (464)..(464)
<223> OTHER INFORMATION: n is a, c, g, t or u

<400> SEQUENCE: 61

```
gggagagtcc atctggaagc tggagtatat cctgacccag acctacgaca ttgaagattt     60
gcagccggaa agtttatatg gattagctaa acaatttaca atcctagaca gtaagcagtt    120
tataaaatac tacaattact tctttgtgag ttatgacagc agtgtaacat gtgataagac    180
atgtaaggcc tttcagattt gtgcaattat gaatcttgat aatatttcct atgcagattg    240
cctcaaacag ctttatataa agcacaatta ctagtatttc acagtttttg ctaatagaaa    300
atgctgattc tgattctgag atcaatttgt gggaatttta cataaatctt tgttaattac    360
tgagtgggca agtagacttc ctgtctttgc tttctttttt tttttctttt tgatgcctta    420
atgtagatat ctttatcatt ctgaattgta ttatatattt aaantgctca ttaatagaat    480
gatggatgta aattggatgt aaatattcag tttatataat tatatctaat ttgtaccctt    540
gttgaaattg tcattta                                                   557
```

<210> SEQ ID NO 62
<211> LENGTH: 545
<212> TYPE: DNA
<213> ORGANISM: Homo sapiens

<400> SEQUENCE: 62

```
acaggaggaa tgcaccacgg cagctctccg ccaatttctc tcagatttcc acagagactg     60
tttgaatgtt ttcaaaacca agtatcacac tttaatgtac atgggccgca ccataatgag    120
atgtgagcct tgtgcatgtg ggggaggagg gagagagatg tactttttaa atcatgttcc    180
ccctaaacat ggctgttaac ccactgcatg cagaaacttg gatgtcactg cctgacattc    240
acttccagag aggacctatc ccaaatgtgg aattgactgc ctatgccaag tccctggaaa    300
aggagcttca gtattgtggg gctcataaaa catgaatcaa gcaatccagc ctcatgggaa    360
gtcctggcac agtttttgta aagcccttgc acagctggag aaatggcatc attataagct    420
atgagttgaa atgttctgtc aaatgtgtct cacatctaca cgtggcttgg aggcttttat    480
ggggccctgt ccaggtagaa aagaaatggt atgtagagct tagatttccc tattgtgaca    540
gagcc                                                                545
```

<210> SEQ ID NO 63
<211> LENGTH: 288
<212> TYPE: DNA
<213> ORGANISM: Homo sapiens

<400> SEQUENCE: 63

```
cacccgccgt ctgagtgaag aggagtttgg ggggttcagg atagggaatg gggaggtcag     60
aggacgcaaa gcagcagcca tgtagaatga accgtccaga gagccaagca cggcagagga    120
ctgcaggcca tcagcgtgca ctgttcgtat ttggagttca tgcaaaatga gtgtgtttta    180
gctgctcttg ccacaaaaaa aaaaaaaaaa aaaaaaaagg gtaactatga gagatggtgg    240
atatgttaac ttgcttcgct ataggaacct ttgtgctatc tatattat                 288
```

<210> SEQ ID NO 64
<211> LENGTH: 468
<212> TYPE: DNA
<213> ORGANISM: Homo sapiens

<400> SEQUENCE: 64

```
caggtactac gtccaagtgg cggctcagga cctcacagac tacggggaac tgagtgactg     60
```

gagtctcccc gccactgcca caatgagcct gggcaagtag caagggcttc ccgctgcctc 120
cagacagcac ctgggtcctc gccaccctaa gccccgggac acctgttgga gggcggatgg 180
gatctgccta gcctgggctg gagtccttgc tttgctgctg ctgagctgcc gggcaacctc 240
agatgaccga cttttccctt tgagcctcag tttctctagc tgagaaatgg agatgtacta 300
ctctctcctt tacctttacc tttaccacag tgcagggctg actgaactgt cactgtgaga 360
tattttttat tgtttaatta gaaaagaatt gttgttgggc tgggcgcagt ggatcgcacc 420
tgtaatccca gtcactggga agccgacgtg ggtgggtagc ttgaggcc 468

<210> SEQ ID NO 65
<211> LENGTH: 515
<212> TYPE: DNA
<213> ORGANISM: Homo sapiens

<400> SEQUENCE: 65
aaagactcta cccatattac agatgggcaa attaaggcat aagaaaacta agaaatatgc 60
acaatagcag ttgaaacaag aagccacaga cctaggattt catgatttca tttcaactgt 120
ttgccttctg cttttaagtt gctgatgaac tcttaatcaa atagcataag tttctgggac 180
ctcagtttta tcattttcaa aatggaggga ataataccta agccttcctg ccgcaacagt 240
tttttatgct aatcagggag gtcattttgg taaaatactt ctcgaagccg agcctcaaga 300
tgaaggcaaa gcacgaaatg ttattttttta attattattt atatatgtat ttataaatat 360
atttaagata attataatat actatattta tgggaacccc ttcatcctct gagtgtgacc 420
aggcatcctc cacaatagca gacagtgttt tctgggataa gtaagtttga tttcattaat 480
acagggcatt ttggtccaag ttgtgcttat cccat 515

<210> SEQ ID NO 66
<211> LENGTH: 360
<212> TYPE: DNA
<213> ORGANISM: Homo sapiens
<220> FEATURE:
<221> NAME/KEY: misc_feature
<222> LOCATION: (51)..(51)
<223> OTHER INFORMATION: n is a, c, g, t or u

<400> SEQUENCE: 66
ttcacttcta aatctgctgg ccacaagccc tgctaaagat acacatctca ncccccctccg 60 ccaagtctga aatgcccctc cccatctcac cttagactga aaagttttaa atcatgtcaa 120
ctggataata cttgctttat gtgagaatac ttcagcagaa tggatacgaa ttttcaaaac 180
aatcttttca tatctatgta ttctatatta aaagtgataa agtcatgttt ctggggcgta 240
ttcaagtagc tgacaagtaa ttatttaata atagtacatg agtgcattgt aatgattctc 300
gccgtagtca ggtaatagta tccaaccgaa atttcctacc aacctgctgt atccaaagtt 360

<210> SEQ ID NO 67
<211> LENGTH: 448
<212> TYPE: DNA
<213> ORGANISM: Homo sapiens

<400> SEQUENCE: 67
gtcccatatt caacatctgc tagtctgtat attcgtccta cattcattgg aactgagcct 60
tctcttggag tcaagaagcc taccaaagcc ctgctctttg tactcttgag cccagtggga 120
ccttattttt caagtggaac ctttaatcca gtgtccctgt gggccaatcc caagtatgta 180
agagcctgga aaggtggaac tggggactgc aagatgggag ggaattacgg ctcatctctt 240
tttgcccaat gtgaagcagt agataatggg tgtcagcagg tcctgtggct ctatggagag 300
gaccatcaga tcactgaagt gggaactatg aatctttttc tttactggat aaatgaagat 360
ggagaagaag aactggcaac tcctccacta gatggcatca ttcttccagg agtgacaagg 420
cggtgcattc tggacctggc acatcagt 448

<210> SEQ ID NO 68
<211> LENGTH: 523
<212> TYPE: DNA
<213> ORGANISM: Homo sapiens
<220> FEATURE:
<221> NAME/KEY: misc_feature
<222> LOCATION: (41)..(41)
<223> OTHER INFORMATION: n is a, c, g, t or u
<220> FEATURE:
<221> NAME/KEY: misc_feature
<222> LOCATION: (440)..(440)
<223> OTHER INFORMATION: n is a, c, g, t or u
<220> FEATURE:
<221> NAME/KEY: misc_feature
<222> LOCATION: (442)..(442)
<223> OTHER INFORMATION: n is a, c, g, t or u
<220> FEATURE:
<221> NAME/KEY: misc_feature
<222> LOCATION: (485)..(486)
<223> OTHER INFORMATION: n is a, c, g, t or u
<220> FEATURE:
<221> NAME/KEY: misc_feature
<222> LOCATION: (488)..(491)
<223> OTHER INFORMATION: n is a, c, g, t or u
<220> FEATURE:
<221> NAME/KEY: misc_feature
<222> LOCATION: (493)..(498)
<223> OTHER INFORMATION: n is a, c, g, t or u

<400> SEQUENCE: 68
gacaacagcc ctggagggga acagagtgag agagatgttt ngctctggta cagcctgtgt 60
tgtttgccca gtttctgata tactgtacaa aggcgagaca atacacattc caactatgga 120
gaatggtcct aagctggcaa gccgcatctt gagcaaatta actgatatcc agtatggaag 180
agaagagagc gactggacaa ttgtgctatc ctgaatggaa aatagaggat acaatggaaa 240
atagaggata ccaactgtat gctactggga cagactgttg catttgaatt gtgatagatt 300
tctttggcta cctgtgcata atgtagtttg tagtatcaat gtgttacaag agtgattgtt 360
tcttcatgcc agagaaaatg aattgcaatc atcaaatggt gtttcataac ttggtagtag 420
taacttacct taccttaccn anaaaaatat taatgtaagc catataacat gggattttcc 480
tcaannannn nannnnnncc ttttgtactt cactcagata cta 523

<210> SEQ ID NO 69
<211> LENGTH: 427
<212> TYPE: DNA
<213> ORGANISM: Homo sapiens
<220> FEATURE:
<221> NAME/KEY: misc_feature
<222> LOCATION: (207)..(207)
<223> OTHER INFORMATION: n is a, c, g, t or u

<400> SEQUENCE: 69
aacctgttct cttgtatctg aatctgattg caattactat tgtactgata gactccagcc 60
attgcaagtc tcagatatct tagctgtgta gtgattcttg aaattctttt taagaaaaat 120
tgagtagaaa gaaataaacc ctttgtaaat gaggcttggc ttttgtgaaa gatcatccgc 180
aggctatgtt aaaaggattt tagctcncta aaagtgtaat aatggaaatg tggaaaatat 240

-continued

```
cgtaggtaaa ggaaactacc tcatgctctg aaggttttgt agaagcacaa ttaaacatct    300

aaaatggctt tgttacacca gagccatctg gtgtgaagaa ctctatattt gtatgttgag    360

agggcatgga ataattgtat tttgctggca atagacacat tctttattat ttgcagattc    420

ctcatca                                                              427


<210> SEQ ID NO 70
<211> LENGTH: 397
<212> TYPE: DNA
<213> ORGANISM: Homo sapiens
<220> FEATURE:
<221> NAME/KEY: misc_feature
<222> LOCATION: (345)..(345)
<223> OTHER INFORMATION: n is a, c, g, t or u

<400> SEQUENCE: 70

aacttatatt gcatgttctc ttcctttcac ttttttcagt gtctacattt cagaccgagt     60

ttgtcagctt ttttgaaaac acatcagtag aaaccaagat tttaaaatga agtgtcaaga    120

cgaaggcaaa acctgagcag ttcctaaaaa gatttgctgt tagaaatttt ctttgtggca    180

gtcatttatt aaggattcaa ctcgtgatac accaaaagaa gagttgactt cagagatgtg    240

ttccatgctc tctagcacag gaatgaataa atttataaca cctgctttag cctttgtttt    300

caaaagcaca aaggaaaagt gaaagggaaa gagaaacaag tgacngagaa gtcttgttaa    360

ggaatcaggt tttttctacc tggtaaacat tctctat                             397


<210> SEQ ID NO 71
<211> LENGTH: 466
<212> TYPE: DNA
<213> ORGANISM: Homo sapiens

<400> SEQUENCE: 71

ccaggctgtg ctgtgcattt ttaaaaggtc taatttaatt gcttttaata tatatgtaca     60

tatatgttat tttaactgtg gagaattatt taagttaaaa gactggtttg atttgcctat    120

ggtgtgaaat cctttgttat ttttctaaaa aaataaaatt taaaaagaaa gaaaactaag    180

gaagaacaag aagctattta cccaaagtga gctttcagtt ttagttttgc atggctgttt    240

gactgccttt ccgccctatg aaaatcaaga aaatcttttt taaaaatgga gtcctgctat    300

tttccactcc ttgcagataa tacaaattca gtttgtcagg ttggatggtg agttgggagc    360

tgtgatggat ctgttggcgg gttttggatg tgtaaagaat gatatatata ttaaataggt    420

caatcagact atgacagcta tgtacgacca tttgtatgtg tatcta                   466


<210> SEQ ID NO 72
<211> LENGTH: 298
<212> TYPE: DNA
<213> ORGANISM: Homo sapiens

<400> SEQUENCE: 72

ccgatttgtg tctattattg gtgacattgt tttagatatt gggtattgta tattaaggaa     60

aaagatggtc tatattctct ttattgcata tacttaatgt ttcaaaagaa tgcagattct    120

gtgtttaagc acagggctga tagttgtggt tttgtttaca aatgttctgt tttggctgct    180

attggttttt taaagaggtt ttttatactt ttgtatttga atagttatgt ttcactgatg    240

ctgagccagt ttgtatgtgt gtgcatatat gtgaactgta actgacaaga tgaattac      298


<210> SEQ ID NO 73
<211> LENGTH: 293
```

<212> TYPE: DNA
<213> ORGANISM: Homo sapiens

<400> SEQUENCE: 73
tgaatcttcg ggtgtttccc tttagctaag cacagatcta ccttggtgat ttggaccctg 60
gttgctttgt gtctagtttt ctagaccctt catctcttac ttgatagact tactaataaa 120
atgtgaagac tagaccaatt gtcatgcttg acacaactgc tgtggctggt tggtgctttg 180
tttatggtag tagtttttct gtaacacaga atataggata agaaataaga ataaagtacc 240
ttgactttgt tcacagcatg tagggtgatg agcactcaca attgttgact aaa 293

<210> SEQ ID NO 74
<211> LENGTH: 537
<212> TYPE: DNA
<213> ORGANISM: Homo sapiens

<400> SEQUENCE: 74
tgatcatggc ctttcaaccc aacaagggcc cttccctgct cttccaccag taaaggctcc 60
tggcctctca tcaggatctg ccccccagag acccccccag acactgcagg gcctggtgat 120
gctgtcctct gtaccggaaa tggcaggcac tgtcagattt ccactcttct gcctttagga 180
aggctgggtg cttcttgctc tgacagccag tctggggaga tgactcttac gttgcttgag 240
tcttggtggc aggctgctgt ccacggggga gaagtctctg ctctggactg gacagaagag 300
agacttttac cctggggcac tcacacggcc aagcttctgc caccacttca ttagctgtat 360
tctccatagt atggtgaaat agcaggtgcg tcttctagtt tattcctcct ggggacattt 420
cctcaaagca gttttgcgcc cccgcaaggg aatggtcagc ctaagggtaa tgtacagccc 480
gtgcttggag aaccatggaa gctacacccc tacaggtgca tactgttctg cttttcc 537

<210> SEQ ID NO 75
<211> LENGTH: 533
<212> TYPE: DNA
<213> ORGANISM: Homo sapiens

<400> SEQUENCE: 75
atcctacaac ccaccttgaa ggtataactg gatccagaga gggaaggact gacaagaagg 60
aattattcag aaaaacactg acagatgttt tataaattgt acagaaaaat agttaaaaat 120
gcaataggtt gaagttttcc agatatgttt ctctctgaaa ttactgtgaa tatttaacaa 180
acacttactt gatctatgtt atgaaataag tagcaaattg ccagcaaaat gtcttgtacc 240
ttttctaaag tgtattttct gatgtgaact tccttcccct tacttgctag gtttcaataa 300
tttaaaagag tcaaacacta taaatgagta agttgacgat gttttaagat tgcacctggc 360
agtgtgcctt tttgcaacaa atatttacct ggcagtgtgc ctttttgcaa caaatattta 420
ctttgcactt ggagctgctt ttaattttag caaaatgttt tatgcaaggc acaataggaa 480
gtcagttctc ctgcacttcc tcctcatgta gtctggagta ctttctaaag ggc 533

<210> SEQ ID NO 76
<211> LENGTH: 486
<212> TYPE: DNA
<213> ORGANISM: Homo sapiens

<400> SEQUENCE: 76
gctcctgtag ctgcattatt tcttgattag aggtttgggc atataaccag attaaagtga 60
aggaactttc tgttgttttt gtagcaccgc tcagctgtct tgtaaaacag tgaacacacg 120
ctttctggtt ctagtaatcc tgggtgttta tcacgttcag agaaactcaa gctattgcat 180
gattagcccc ctatctggca aggaaacccc atacagaaga aacaacaaac ctgcgcctgc 240
accgcctctg cgtcctgggt agtctgtgct tgtaatccag catgtttcac agagtaagcc 300
tgttgtgact ttgcttttgg ggtctatgtc attggtttct gatgcttgta caaacacgca 360
cacacaaatg gataaaacag cacctctggc tgttacatta ccataaacca tatcacatgc 420
ctacatttta caaatgattt ctggtttctc ttagttcttc tctaacatag tactttcttt 480
ccagca 486

<210> SEQ ID NO 77
<211> LENGTH: 530
<212> TYPE: DNA
<213> ORGANISM: Homo sapiens

<400> SEQUENCE: 77
aagtgtgcat aatttcattt aacgttaaag aaatagatcc aattcctttc ttgcaaccaa 60
aaataaataa aatacgttgc ctcaatataa ggtttgggct attctgtgtt tctatagaag 120
caatctgttt ttggtaaaat gtacttttaa ggatccagtc atctgaagta ttttatgtag 180
agttagagat ttcacaatat tgactataca tatatttaaa atataaatta tccagctgat 240
gtttgaattt gtcttacttt cctggccacc tcgttgtcct attttataag ctggggagtt 300
aactagctta acaaaagatg cttagctttt gtaaaagaac aagtgtttca ttttacaaag 360
acactccaaa tgatagttac ttgattttct cgagaccttt aactatggtg atgaataaca 420
ggacttgctt tcaagcctta ataaatgtaa aatgcctttt aatgaagata cagctgagtg 480
ttttcctcat gaatctgaac caattaccaa tttgtgttcc agtcttgatt 530

<210> SEQ ID NO 78
<211> LENGTH: 557
<212> TYPE: DNA
<213> ORGANISM: Homo sapiens
<220> FEATURE:
<221> NAME/KEY: misc_feature
<222> LOCATION: (477)..(477)
<223> OTHER INFORMATION: n is a, c, g, t or u

<400> SEQUENCE: 78
ctaagaggca gtttacttcc ctgagaccca cagttgggct gttctggaaa cacatctgtg 60
aatcatagcc aattgccaca gagaaaacag aaccaagcct ccggtgaggc cactccaccc 120
cagagaagtc tgcagaattc caaggactcg gattggatgt tcagaattca gcaactggaa 180
agtccttaaa aacaaacagg ccaaaccaaa tcaatattgc tgtttctaga tgtcccttct 240
gtggttgagc tagttttaca gagataaata tattaagaca aggaggtggg ggtgttatat 300
gatcaatgat agccatttga aagagaggga ggagtacaga aggaaggcac ttctgggtac 360
ttaattcaga aatttcttta tatttcagca ctggattatc atataatgca agtgactatg 420
gactaagagt tagttatggt gtcttatgac tagatttatt atggtatatt aaagtancaa 480
taatattaat attaccttcc ttgttttttg gtttcaaaaa gagatctttt ccagatgttc 540
agctgttggg cttctta 557

<210> SEQ ID NO 79
<211> LENGTH: 291
<212> TYPE: DNA
<213> ORGANISM: Homo sapiens
<220> FEATURE:
<221> NAME/KEY: misc_feature
<222> LOCATION: (87)..(87)
<223> OTHER INFORMATION: n is a, c, g, t or u
<220> FEATURE:
<221> NAME/KEY: misc_feature
<222> LOCATION: (94)..(94)
<223> OTHER INFORMATION: n is a, c, g, t or u
<220> FEATURE:
<221> NAME/KEY: misc_feature
<222> LOCATION: (102)..(102)
<223> OTHER INFORMATION: n is a, c, g, t or u
<220> FEATURE:
<221> NAME/KEY: misc_feature
<222> LOCATION: (110)..(110)
<223> OTHER INFORMATION: n is a, c, g, t or u
<220> FEATURE:
<221> NAME/KEY: misc_feature
<222> LOCATION: (123)..(123)
<223> OTHER INFORMATION: n is a, c, g, t or u

<400> SEQUENCE: 79
ctttcaggtt tatctccatc cctggaagca gagttgctct ggcccaggct ctccatgaga 60
gtttggcttg aacattcatt gtctggnccc cctncctagt tnctcatctn cccaaagtca 120
agnccaatgt gtgaagaaat gaccagctca gcagccaagg cccagggtgc acaggtcttc 180
gttgggagag gcatctgcag gcctttcctt gcccactggg atccttgcct agcatagtga 240
cgatgttcag ccctggagac aaacaagaag gggaacacca acatcaatag a 291

<210> SEQ ID NO 80
<211> LENGTH: 477
<212> TYPE: DNA
<213> ORGANISM: Homo sapiens

<400> SEQUENCE: 80
gttgatgcca aaatacccac ggggtctacc agccatgggg tttgcttgct taggagtagt 60
tgtttcagag gtgattacag gcctgggttt gactgtgctt accaatgagt ggtttttgag 120
ctatgagaaa gtggatggga gtgggaggag gagagatggg tgaagacaaa agagttcttt 180
atgagcctcg atgttccctg gtaaactttt aaaaaggcct tctctcatga tctaagtctt 240
ggactggtgg catcatgtaa ctgctaacct tacagtaaaa acccaagaat gggtcaaaaa 300
tgtcttccca gtttctccaa gctgcttctg gaatgcaggt ctgtcggctg ggtgctctcc 360
agcagctgct cctgcctgat tcaactgtag cctgtaatgg gtaaaagcca catttaggag 420
gtggtctgat catagaacac cttaggaaga aagtccatga gactttctga ctaggaa 477

<210> SEQ ID NO 81
<211> LENGTH: 540
<212> TYPE: DNA
<213> ORGANISM: Homo sapiens

<400> SEQUENCE: 81
tagaacgggc atctactcca gtacttcctg ccataaaact ccagataaag taaaccatgc 60
agtactggct gttgggtatg gagaaaaaaa tgggatccct tactggatcg tgaaaaactc 120
ttggggtccc cagtggggaa tgaacgggta cttcctcatc gagcgcggaa agaacatgtg 180
tggcctggct gcctgcgcct cctaccccat ccctctggtg tgagccgtgg cagccgcagc 240
gcagactggc ggagaaggag aggaacgggc agcctgggcc tgggtggaaa tcctgccctg 300
gaggaagttg tggggagatc cactgggacc cccaacattc tgccctcacc tctgtgccca 360
gcctggaaac ctacagacaa ggaggagttc caccatgagc tcacccgtgt ctatgacgca 420
aagatcacca gccatgtgcc ttagtgtcct tcttaacaga ctcaaaccac atggaccacg 480
aatattcttt ctgtccagaa gggctacttt ccacatatag agctccaggg actgtctttt 540

<210> SEQ ID NO 82
<211> LENGTH: 503
<212> TYPE: DNA
<213> ORGANISM: Homo sapiens

<400> SEQUENCE: 82
aggactaaac tacagccgct tgttgtttgg tattcagtat ccagattctg atgttttatt 60
tagatacaaa gtgaaatctt agagaagcta aaaggaaaga aaataaatct atcaaaatta 120
ccctaaacat cctaagctca tctatttctt tttaatttct gcaaagtaat tgatttattt 180
gtttaaaaag cgctaatttc tatttgatct gatatcagtc cagtttgtcc ttagtcacaa 240
agcccatata atataaaaca ggatggtggc aggaaaatgg acatcaaaat caacttaagg 300
gtaggctcaa aacagggttg ttgttgtttt tttagtttct ccttgttgtg attttcacct 360
gttataataa atgtaccttc acaccaatag attgggcact gtggaattta aatcactcaa 420
attgttctct aatatgtaaa attacacttt gaactactag aaaattgtgc tggaaatgga 480
cacagtctaa caaattccaa att 503

<210> SEQ ID NO 83
<211> LENGTH: 375
<212> TYPE: DNA
<213> ORGANISM: Homo sapiens

<400> SEQUENCE: 83
tgggcccaag gaattcagaa gagcttgcag gcaagccagg agaccctggg agctgtggct 60
gtcttctgtg gaggaggctc cagcattccc aaagctctta attctccata aaatgggctt 120
tcctctgtct gccatcctca gagtctgggg tgggagtgtg gacttaggaa aacaatataa 180
aggacatcct catcatcacg gggtgaaggt cagagtaagg cagccttctt cacaggctga 240
gggggttcag aaccagcctg gccaaaaatt acaccagaga gacagagtcc tccccattgg 300
gaacagggtg attgaggaaa gtgaaccttg ggtgtgaggg accaatcctg tgacctccca 360
gaaccatgga agcca 375

<210> SEQ ID NO 84
<211> LENGTH: 485
<212> TYPE: DNA
<213> ORGANISM: Homo sapiens

<400> SEQUENCE: 84
gctactccag gggctgaggt gacagcattg cttaagccca gaaggtcgag gctgcagtga 60
gctgagatca cgccactgca ctccagtctg ggtgacagag agagaccata tccaaaaaaa 120
aaaaaagttg ccagagacga gtatgcccat gctccctcta cctcactgcc accactcctg 180
cttttaggag ctgagtgtgt ctccctaaaa tttctatgtt gaagtcttaa cccttggtac 240
cacagaatat cactgtattt ggagatgggg tctttagaaa ggcacttaaa ttaaaatgag 300
ctcactgata tgggccccga tgcaatataa ttggtgtcct tataagaagg ggaggttagg 360
acacgcagga aagaccacat gaaggcccag gagtgggagg gggaatagcc atcgacaaac 420
taagggggcc tcagaggaaa ccaaccctgc tgacacctca atcttagact ctggcctcaa 480
aaatt 485

<210> SEQ ID NO 85
<211> LENGTH: 566

<212> TYPE: DNA
<213> ORGANISM: Homo sapiens

<400> SEQUENCE: 85
tgaaatctta ggtgccttag gggttttttt tttttaagta ttttttaaaa acctgcaaag 60
atataaattt agccaagtta cctgacgggt gagaagaaaa gagcaggcaa aattagtgat 120
ttttttagaa gtctgctaaa tggatatatt gtgtgtgttg ctgttggaaa tagccccacc 180
ccatcctccc aatccaaaac gtaactgaaa tataatcaga aacattaaag cctgtaaaaa 240
aaaattgctg cgtttttggt aaagggtgta atttaacagt gcaatttaaa gtgaccttag 300
tgatgcagag ttcctgagtg gtgtttgtag aatgagttta tcatacattc tttctactac 360
tggaaaaaaa tggatgcagt ctggactgtt gtaaccttag gttgtaatct gatttggaaa 420
taagtacatc tttaaaagtt gctacagatt tgagttcatg attttgttaa aaattgctat 480
ggagtacttt gttatataac agaagccatc ctgaaatgaa actagtctaa aaaaattcat 540
tgttctactt agttgcagct gtacct 566

<210> SEQ ID NO 86
<211> LENGTH: 317
<212> TYPE: DNA
<213> ORGANISM: Homo sapiens

<400> SEQUENCE: 86
aaatgttgct aagtcctggt atgatggtgt gagcttcctt ggggaagtac ttcttgagtt 60
atgtaactaa caggatgttt tactacagat ctggatggct attcagataa catggcaaaa 120
aatgatagca gaagatcatt aaaaacttaa aatatatttt attagaaaac atttatctat 180
gaatgaatat ttccttgatg ctggtctctg cacacatatg cttggttact tgcatgcatt 240
cattggttgt tcaataagtg agatgattac agataatact gtattttcct tatatggaaa 300
accgttatag acccaat 317

<210> SEQ ID NO 87
<211> LENGTH: 317
<212> TYPE: DNA
<213> ORGANISM: Homo sapiens

<400> SEQUENCE: 87
gaagggagag ccatctatga tatagatggt accatttcag ttcaaagttg taataacctt 60
tggagtgtta cagtttggtt gtcaaatggt ttcagaatgt ataattgatt tttttaaatg 120
ttgcattgtt tgaatctaaa gtacagcact ataacatgct ttagcttggg ggggtggggg 180
tggggtgggg acttgcactt attctctaaa atgttgacta atccagaaag cctgatgcaa 240
cataatctgg aaaactgctt tggtacattt gtagaaatcc gtagaaatac catatccagc 300
ctcaaagcat taatctc 317

<210> SEQ ID NO 88
<211> LENGTH: 128
<212> TYPE: DNA
<213> ORGANISM: Homo sapiens

<400> SEQUENCE: 88
attgctgtaa atagggcaca agccctgtat atggattaga tggtcgatat gccaaaaact 60
acagatggtt tctaagtaga tttctcacct ttccttggag gcatattgta gcttgctaag 120
ttttatca 128

<210> SEQ ID NO 89
<211> LENGTH: 402
<212> TYPE: DNA
<213> ORGANISM: Homo sapiens

<400> SEQUENCE: 89
gcacctcgga gttgcagctg tgacactcat aggttactcc caggagtgtg ctgagcagaa 60
ggcaagctct tgctggatga aacccctcca ggtggggttg gggagacttg atattcacat 120
ccaacagttt gaaaagggag agctcaattc ccagcgtcac cccatggctt gtgttgcctg 180
ctacgcattg acttggatct ccaggagtcc cctgcacata ccttctccat cgtgtcagct 240
gtgtttctct tgattccgtg acacccggtt tattagttca aaagtgtgac accttttctg 300
ggcaaggaac agccccttta aggagcaaat cacttctgtc acagttatta tggtaatatg 360
aggcaatctg attagcttca cagactgagt ctccacaaca cc 402

<210> SEQ ID NO 90
<211> LENGTH: 475
<212> TYPE: DNA
<213> ORGANISM: Homo sapiens

<400> SEQUENCE: 90
cagggatcgg aggacgaccc gagtcccaag agtggggttt tgctttttaa aaggagagag 60
gaggggtgat ggcaggggag tggagggtgg ccgggcaggt cctgccggcg cagggagccc 120
tctgcccttc acactctcct ccaaaagagc ctccatctgt aaggaagcag gtctccgcga 180
ggggtttctt tccatgtgtt ttcctcctgt tgttaaaaga actttttttaa aaaaacagac 240 ctcgttttag atttatagca ttgactttta cacacattca cacaagaaaa aaatcctttc 300
aaaattctta aatcttctgt tcctcctttt tccaagggaa gagggcaaaa agtggcctgg 360
gctctgttgg tgtgcgtgtt ccgtggcgga gagaagaaaa tgggaaagac atctcactgg 420
tgcttttctc ttttgtttta gtgccccccg cccccatccc tataatatct gtaac 475

<210> SEQ ID NO 91
<211> LENGTH: 491
<212> TYPE: DNA
<213> ORGANISM: Homo sapiens
<220> FEATURE:
<221> NAME/KEY: misc_feature
<222> LOCATION: (314)..(314)
<223> OTHER INFORMATION: n is a, c, g, t or u

<400> SEQUENCE: 91
ggcggcaata gtttcagctt cagcagcgcc agcagtctta gtagcagcag caccagtgcg 60
ggttgcgcca gcagccttgg cggcggcggc gcctcggagc ttctccctgc aacacagccc 120
acagccagca gcgctcccaa aagccccgag ccagcccaag gcgcgcttgg ctgcttatag 180
actgtactag ggcggagggg atccgggcct tgcgtgcagc ctcccaacca tgggctgggt 240
tttgtgctta ctgtatgttg gcgacttggt agggcaggag acgcagcgtg gagcctacct 300
cccgacattc acgnttcgcc ccacgctgct ccgactggct gcagcggaca ctgcccaaag 360
cagaggggag tctcagtgtc ctgctagcca gccgaacact tctctccgga agcaggctgg 420
ttcgactgtg aggtgtttga ctaaactgtt tctctgactc gccccagagg tcgtggctca 480
aaggcactta g 491

<210> SEQ ID NO 92
<211> LENGTH: 483

```
<212> TYPE: DNA
<213> ORGANISM: Homo sapiens
<220> FEATURE:
<221> NAME/KEY: misc_feature
<222> LOCATION: (48)..(48)
<223> OTHER INFORMATION: n is a, c, g, t or u
<220> FEATURE:
<221> NAME/KEY: misc_feature
<222> LOCATION: (212)..(212)
<223> OTHER INFORMATION: n is a, c, g, t or u

<400> SEQUENCE: 92

ggaattcttg ttcaatactg gcaggagtga aaattggtag aacctttnta gaaggcaatt     60

tggcaacatg tatgaaaacc taaatgttga tacaccttta cccagcagtt tgtttaggaa    120

tttatcctaa tgaataaaag ttgtccaagt cttcaaacat gagcccaaag gtatatttca    180

tgatgtttat gatattaaaa cattggaaac anctgaaaca tccttcagta aaagatggat    240

taaataaatt ccatgcagtt gtcatttaaa aatatttaga tatatgttta ttgctatgga    300

tatatgttcc caaaatatta ttgaatcaaa aagtagacta caggatatat gttgaatatg    360

agctcattta taacattgaa tattttaaga taatgtatgt ttcatagaga gatcttcacc    420

aaatgttaag gatttttttt tctgggctgt ggtatttggg tgatctttac attcttcaga    480

ctc                                                                  483

<210> SEQ ID NO 93
<211> LENGTH: 560
<212> TYPE: DNA
<213> ORGANISM: Homo sapiens

<400> SEQUENCE: 93

tcccaaagta tatagttcca tcccaggact taaggcccta taaggtaaat atagatcctt     60

cttcagaagc tccagggcat tcttgcagga gcaggccagt ggagagcagc tgttcctcca    120

aattttcctg ggatgaatat gaacagtaca aaaaagaata aattctacca gaagataaag    180

aaaaaagcaa gtattgcata ggcacctgag cataggtatg accttgggaa gacattggct    240

ccataagcaa tgccaagaga atgatcaata gtgagtttgg gtgatgcaga taaacaatct    300

ggataattcc atttcttttt tcccaaaccc tcaaacagag tgccttaaaa aattgtttta    360

tcaggataat tgtctcatga ccaaatccac gctcaattag agccattcaa aattccttaa    420

gatcatgggt tctgacttca gccaaacaaa acaatcaaaa cctaccaaaa agggactgga    480

ttgtaatgtc ctctccatca tcctcagtgt gagtcctcag agcctccatc tgccaagaac    540

attcagttgg attccatcgt                                                560

<210> SEQ ID NO 94
<211> LENGTH: 532
<212> TYPE: DNA
<213> ORGANISM: Homo sapiens

<400> SEQUENCE: 94

gtttcttgca tatgtattta ctggtccaca gcacaaaata aagtgaccac atatacatag     60

gaaagttgaa tttgtacaca tacagcatct gaaatgtatc tgatgttcag catcaagatt    120

tcactgaaca ttgtagaaat gtgtatcttt tgcatgtata ttttacattg attttctatt    180

tatgtacatc tagaaagttt taaccctaat aaatagtttt gtaattttga ataatagtgt    240

cagtttatat gtgagggagt agagacagag aggttagcac tggataataa ttagtaaggc    300

caaaggagaa aatttcatag aaaatattgt tgttgtcata atgagtacag catgaaaggc    360
```

ttcctctaca agacactagt caaagagttg agagctgcgg tttctaatct ttgtccatta 420
ctcccttact ccctatgaga ctgtggacct gtcacttggc ctctctggtc ttcagttttc 480
tcaccagtaa aacaaggaac ttgaaccaaa tgacctctag tgttcccctt gg 532

<210> SEQ ID NO 95
<211> LENGTH: 311
<212> TYPE: DNA
<213> ORGANISM: Homo sapiens

<400> SEQUENCE: 95
gttttgtttt tactacggtg ctgatgtata tgtaatgtct aaaaaaagtt atttgtacat 60
aagtttttac aatactgcag atatcactgg gtctactatc tgtaaaaaat atacatataa 120
atatatatat actgtttgtt taaaatagag tatttttatt tcattcctta actcatcatc 180
acagcagtgg tattgcactt cagatgacat ctaattacta atttgtactg tatgacctct 240
ggcaacttgc tccattttat tcagattttt ctagttttct gtttttactt tgtacattga 300
gcattgctta t 311

<210> SEQ ID NO 96
<211> LENGTH: 546
<212> TYPE: DNA
<213> ORGANISM: Homo sapiens

<400> SEQUENCE: 96
acacgtgttg actccattgt tttacatgta gcaaagtctg ccatctgtgt ctgctgtatt 60
ataaacagat aagcagccta caagataact gtatttataa accactcttc aacagctggc 120
tccagtgctg gttttagaac aagaatgaag tcattttgga gtctttcatg tctaaaagat 180
ttaagttaaa aacaaagtgt tacttggaag gttagcttct atcattctgg atagattaca 240
gatataataa ccatgttgac tatgggggag agacgctgca ttccagaaac gtcttaacac 300
ttgagtgaat cttcaaagga ccctgacatt aaatgctgag gctttaatac acacatattt 360
tatcccaagt ttataatggt ggtctgaaca aggcacctgt aaataaatca gcatttatga 420
ccagaagaaa aataatctgg tcttggactt tttattttta tatggaaaag ttttaaggac 480
ttgggccaac taagtctacc cacacgaaaa aagaaatttg ccttgtccct ttgtgtacaa 540
ccatgc 546

<210> SEQ ID NO 97
<211> LENGTH: 457
<212> TYPE: DNA
<213> ORGANISM: Homo sapiens

<400> SEQUENCE: 97
cagtccctgc ttttgactgg gttcctattt taagcacaaa tgagagctct ggagccagaa 60
tgccagggtt ctaacttcag cattcactta ctagctgtat gatcttggcc aagtcacttc 120
acctccctga gccccaattc ccaagtttgt gaaatggcaa caatacctat gtgtcactgg 180
attattggtt aaaacagaat gagattcctt gtgtgaaaat agctattata cctgacacac 240
tcatcgtatg ggctctgcaa agggatattc cccaacctgt ccttcccgac aggaagcata 300
gggcactgca gatggggaag catgtcacct tggcagtgac tcggtggctt cccaagcagg 360
agtgtcaggg gaaccatgag agagagtcta ggagccaaac acatcaccac cctgagcaga 420
tacaggagtg gggagggggc tgtaactcag tgagtgg 457

<210> SEQ ID NO 98
<211> LENGTH: 530
<212> TYPE: DNA
<213> ORGANISM: Homo sapiens

<400> SEQUENCE: 98
tcaaagaacg cgtactgcag accccaaatg accttctggc tgctggcttt gaggagcaca 60
agttcagaaa cttcttcaat gctttttaca gtgtggtgga actggtagag aaggacggct 120
cagtgtccag cctgctgaag gtgttcaacg accagagtgc ctcggaccac atcgtgcagt 180
tcctgcgcct gctcacgtcg gccttcatca ggaaccgagc agacttcttc cggcacttca 240
ttgatgagga gatggacatc aaagacttct gcactcacga agtagagccc atggccacgg 300
agtgtgacca catccagatc acggcgttgt cgcaggccct gagcattgcc ctgcaagtgg 360
agtacgtgga cgagatggat accgccctga accaccacgt gttccctgag gccgccaccc 420
cttccgttta cctgctctat aaaacatccc actacaacat cctttatgca gccgataaac 480
attgattaat tttaggccat gcagtggaac ctgtcaccta atgggactgc 530

<210> SEQ ID NO 99
<211> LENGTH: 510
<212> TYPE: DNA
<213> ORGANISM: Homo sapiens

<400> SEQUENCE: 99
atggcctctg tgaataatgt aactccagtt acacggtgac ttttaatagc atacagtgat 60
ttgatgaaag gacgtcaaac aatgtggcga tgtcgtggaa agttatcttt cccgctcttt 120
gctgtggtca ttgtgtcttg cagaaaggat ggccctgatg cagcagcagc gccagctgta 180
ataaaaaata attcacacta tcagactagc aaggcactag aactggaaaa gaccacagaa 240
aacaaagaat ccaacccttt catcttacag gtgaacaaac tgtgatgatg cacatgtatg 300
tgttttgtaa gctgtgagca ccgtaacaaa atgtaaattt gccattatta ggaaagtgct 360
ggtggcagtg aagaagcacc caggccactt gactcccagt ctggtgccct gtctacacca 420
gacaacacag gagctgggtc agattcccct cagctgctta acaaagttcc tcgaacagaa 480
agtgcttaca aagctgcctt ctcggatact 510

<210> SEQ ID NO 100
<211> LENGTH: 560
<212> TYPE: DNA
<213> ORGANISM: Homo sapiens

<400> SEQUENCE: 100
agctgccttc tcggatactg aaaggtcgag ttttctgaac tgcactgatt ttattgcagt 60
tgaaaaaccc aaagctattc caaagatttc aagctgttct gagacatctt ctgatggctt 120
tacttcctga gaggcaatgt ttttacttta tgcataattc attgttgcca aggaataaag 180
tgaagaaaca gcaccttttt aatatatagg tctctctgga agagacctaa atttagaaag 240
agaaaactgt gacaattttc atattctcat tcttaaaaaa cactaatctt aactaacaaa 300
agttcttttg agaataagtt acacacaatg gccacagcag tttgtcttta atagtatagt 360
gcctatactc atgtaatcgg ttactcacta ctgcctttaa aaaaaaccag catatttatt 420
gaaaacatga gacaggatta tagtgcctta accgatatat tttgtgactt aaaaaataca 480
tttaaaactg ctcttctgct ctagtaccat gcttagtgca aatgattatt tctatgtaca 540
actgatgctt gttcttattt 560

<210> SEQ ID NO 101
<211> LENGTH: 392
<212> TYPE: DNA
<213> ORGANISM: Homo sapiens

<400> SEQUENCE: 101
atcggccatg ccatcctgag atgaatgaac acattggcca tgctgtcttg agatgaatga 60
acacctgggc catgctgtct tgagatgaat gaacacctgg gccatgctgt cctgagacga 120
atgaacacct gggccatgct gtcttgagat gaatgaacac atcagccatg ctctcctgag 180
agggatgaac acctgggcct tgccgtcctg agatgaatga acacattgac catgctgtcc 240
tgagatgatt gtcctggtta tgcagacatt tctttatatt atttgcttaa ctttaatgcc 300
ctcctaggaa gatttcccat actttcctcc cttcaatcaa aatatcccaa gttcaacagg 360
tctggctcac tcctctctat tcatctaagg tc 392

<210> SEQ ID NO 102
<211> LENGTH: 348
<212> TYPE: DNA
<213> ORGANISM: Homo sapiens

<400> SEQUENCE: 102
tgaagctgag ctccgacggc agtttgagga gcgacagcag gagatggagc atgtttatga 60
gctcttggag aataagatgc agcttctgca ggaggaatcc aggctagcaa agaatgaagc 120
tgcgcggatg gcagctctgg tggaagcaga gaaggagtgt aacctggagc tctcagagaa 180
actgaaggga gtcaccaaaa actgggaaga tgtaccagga gaccaggtca agcccgacca 240
atacactgag gccctggccc agagggacaa gatctaaaaa aaataatgct gggaagtcct 300
aaccacatca agaatgcctc agatcagtga cccaaggacc ttccagaa 348

<210> SEQ ID NO 103
<211> LENGTH: 460
<212> TYPE: DNA
<213> ORGANISM: Homo sapiens

<400> SEQUENCE: 103
cttgggccac aaaatatcag tttaatcaga tggtttatgt taacaagtat gatttatggc 60
aaacatagat ctctaatctc catttctctc tcatatatct atatttatct atccatatat 120
atgtacctat atatatcaaa tataaagata tgtttatagc aattgtatat acgtagagag 180
ataatatgta gtatgaagag agacatagat attattcttc attttagaat gttatcttgg 240
tatgtttaaa aggaaaaact taagatgtgt tgcaattgca gtatgagttt caggtatgta 300
catgttatgt gtgtgtgtga gagacacaca caaacacatt tcaaacatgt tttatgttta 360
agctcaatat tcaaacacag aaatataaca tctattctta atatgtttta tgtaagtaca 420
gcagcagcat tattaaatac tgtatttcta tggtgattga 460

<210> SEQ ID NO 104
<211> LENGTH: 601
<212> TYPE: DNA
<213> ORGANISM: Homo sapiens

<400> SEQUENCE: 104
ccttggctat cttgatgacc caagtgagga cattcaggat ccagtgagtg acaaattctt 60
caaggaggtg tgggtttcaa cagcagctcg aaatgctaca atttatgaca aggttttccg 120
gtgccttccc aatgatgaag tacacaattt aattcagctg agagacttta taaacaagcc 180
cgtattagct aaggaagatc ccattcgagc tgaggaggaa ctgaagaaga tccgtggatt 240
tttggtgcaa ttccccttt atttcttgtc tgaagaaagc ctactgcctt ctgttgggac 300
caaagaggcc atagtgccca tggaggtttg gacttaagag atattcattg gcagctcaaa 360
gacttccacc ctggagacca cactgcacac agtgacttcc tggggatgtc atagccaaag 420
ccaggcctga cgcattctcg tatccaaccc aaggaccttt tggaatgact ggggagggct 480
gcagtcacat tgatgtaagg actgtaaaca tcagcaagac tttataattc cttctgccta 540
acttgtaaaa agggggctgc attcttgttg gtagcatgta ctctgttgag taaaacacat 600
a 601

<210> SEQ ID NO 105
<211> LENGTH: 381
<212> TYPE: DNA
<213> ORGANISM: Homo sapiens

<400> SEQUENCE: 105
accggcggag gaaatgctct acaggcaatc atgcacttca actacagaac catgtgcaga 60
ggagaaaatt ccatccttgg acagttaaaa gcagagcttg gtaatcagtg gataaattac 120
atatcattct gtggtcttag aacacatgca gagctcgaag gaaacctagt aactgagctt 180
atctatgtcc acagcaagtt gttaattgct gatgataaca ctgttattat tggctctgcc 240
aacataaatg accgcagcat gctgggaaag cgtgacagtg aaatggctgt cattgtgcaa 300
gatacagaga ctgttccttc agtaatggat ggaaaagagt accaagctgg ccggtttgcc 360
cgaggacttc ggctacagtg c 381

<210> SEQ ID NO 106
<211> LENGTH: 409
<212> TYPE: DNA
<213> ORGANISM: Homo sapiens

<400> SEQUENCE: 106
aactggctct tgattttcag caccctactc tcatgaaaaa agcctgaaag gaccctttcc 60
cttataagta atttaatcca atttctcccc attttataga tgaggaaact gaggctcaga 120
tcagatgaga actcacttaa atccactcaa tgtgtagatg gtagagctgg gactagcaac 180
attgctgcag cccattgttg gcctctctct tcactttatc attgcccaag aatgaggata 240
tgcagtaaac agaattcagg caagatacct ctaagctgtt ttgaaccctc tgatattttg 300
tatttatgtg tttgtctgtc tccccctact agaatgtaag ctccatgggg cagggacttc 360
actgtatttt gttcatagtg tatccccaga gcctggacca gtgcttggc 409

<210> SEQ ID NO 107
<211> LENGTH: 564
<212> TYPE: DNA
<213> ORGANISM: Homo sapiens

<400> SEQUENCE: 107
catctttcag ggctgccagt ttcgctccgt ggaggctgtg caggagatca cagagtatgc 60
caaaagcatt cctggttttg taaatcttga cttgaacgac caagtaactc tcctcaaata 120
tggagtccac gagatcattt acacaatgct ggcctccttg atgaataaag atggggttct 180
catatccgag ggccaaggct tcatgacaag ggagtttcta aagagcctgc gaaagccttt 240
tggtgacttt atggagccca agtttgagtt tgctgtgaag ttcaatgcac tggaattaga 300

-continued

```
tgacagcgac ttggcaatat ttattgctgt cattattctc agtggagacc gcccaggttt    360

gctgaatgtg aagcccattg aagacattca agacaacctg ctacaagccc tggagctcca    420

gctgaagctg aaccatcctg agtcctcaca gctgtttgcc aagctgctcc agaaaatgac    480

agacctcaga cagattgtca cggaacacgt gcagctactg caggtgatca agaagacgga    540

gacagacatg agtcttcacc cgct                                           564
```

<210> SEQ ID NO 108
<211> LENGTH: 370
<212> TYPE: DNA
<213> ORGANISM: Homo sapiens
<220> FEATURE:
<221> NAME/KEY: misc_feature
<222> LOCATION: (140)..(140)
<223> OTHER INFORMATION: n is a, c, g, t or u
<220> FEATURE:
<221> NAME/KEY: misc_feature
<222> LOCATION: (166)..(166)
<223> OTHER INFORMATION: n is a, c, g, t or u
<220> FEATURE:
<221> NAME/KEY: misc_feature
<222> LOCATION: (200)..(200)
<223> OTHER INFORMATION: n is a, c, g, t or u

<400> SEQUENCE: 108

```
ggtttagcat ttagttctct ttattatagt ggatctttat tgttcattta tgtatgaaac     60

ctgtgctagg gattatagaa gatacaaatt tgaataaaat atttgatcta ggagctctta    120

tctaaaatgc cataaccatn tgcttaatta taaaatgaaa gaaggnctat aaaatgatac    180

atagtaaaaa ttttaacagn ctatgagagt ttaaaggaaa aggatacaaa ttatgactgc    240

attgaaaaat agcactttga agctgagcat ggtgatgcat gcctttagtc ccagctactc    300

aggaggctga gatgggagga ctacttgagc ctgggaggtc gaggctgtag tgaggcatga    360

ttgcaccact                                                           370
```

<210> SEQ ID NO 109
<211> LENGTH: 456
<212> TYPE: DNA
<213> ORGANISM: Homo sapiens

<400> SEQUENCE: 109

```
atacaaagta cttctgttgg tcacagaaac atgaccagat tttgcatatc tccaggtagg     60

gaactaagta gactacctta tcaccggcta agaaaacttg ctactaaact attaggccat    120

caatggcttg aataaaaacc agagaaggtt tttcccagga cgtctcatgt ttggcccttt    180

agaattgggg tagaaatcag aaatgagatg aggggaagaa gcaaggagtc taaggcccta    240

gcgatttggg catctgccac attggttcat attcagaaag tgttatctca ttgattatat    300

tcttgttaag caaatctcct taagtaatta ttattcaaat aagattatac tcatacatct    360

atatgtcact gttttaaaga gatatttaat ttttaatgtg tgttacatgg tctgtaaata    420

tttgtattta aaaatgccat gcattaggct ttggaa                              456
```

<210> SEQ ID NO 110
<211> LENGTH: 257
<212> TYPE: DNA
<213> ORGANISM: Homo sapiens

<400> SEQUENCE: 110

```
atttgttttt tgactaatgt gctataaaaa ggattatatt tgtgagaaaa gatactgatc     60

gccaatattt caaataccgt cttgcaatgt atagttttta gtgacattgt agtataaagc    120
```

tgtaatttga aattttactt tggaatgtaa agtagaaaat attagctatg tcaatgatat 180
cttgcaaagt gttcccattt ataattattt atattgtaaa tagctttctg aagtaaattc 240
gaagttaatg tgcataa 257

<210> SEQ ID NO 111
<211> LENGTH: 474
<212> TYPE: DNA
<213> ORGANISM: Homo sapiens

<400> SEQUENCE: 111
gtttattgca actttgctgc atgggacttt gctttcataa atctatatgg ggttggggtt 60
aatttgccct aatttgctga cctgggacac atgtaatcac tgttaaactt acacccggta 120
accctgatgt gtttacattt caaaagaaat gaaattggcc tggaaaaaaa ttttggaagt 180
actgtaagtc ttttttcttt ttttttccga agggaaatat ttcaaaaaag gaaacattat 240
gagtagacac ttcaaaaaag ataaaatatt ttacatttgt tttttgacta atgtgctata 300
aaaaggatta tatttgtgag aaaagatact gatcgccaat atttcaaata ccgtcttgca 360
atgtatagtt tttagtgaca ttgtagtata aagctgtaat ttgaaatttt actttggaat 420
gtaaagtaga aaatattagc tatgtcaatg atatcttgca aagtgttccc attt 474

<210> SEQ ID NO 112
<211> LENGTH: 501
<212> TYPE: DNA
<213> ORGANISM: Homo sapiens
<220> FEATURE:
<221> NAME/KEY: misc_feature
<222> LOCATION: (116)..(116)
<223> OTHER INFORMATION: n is a, c, g, t or u

<400> SEQUENCE: 112
gtattccaag tttactccat tacatgtcgg ttgtctggtt gccattgttg aactaaagcc 60
tttttttgat tacctgtagt gctttaaagt atatttttaa aagggaggaa aaaaantaac 120
aagaacaaaa cacaggagaa tgtattaaaa gtatttttgt tttgttttgt ttttgccaat 180
taacagtatg tgccttgggg gaggagggaa agattagctt tgaacattcc tggcgcatgc 240
tccattgtct tactatttta aaacatttta ataattttg aaaattaatt aaagatggga 300
ataagtgcaa aagaggattc ttacaaattc attaatgtac ttaaactatt tcaaatgcat 360
accacaaatg caataataca atacccccttc caagtgcctt tttaaattgt atagttgatg 420
agtcaatgta aatttgtgtt tatttttata tgattgaatg agttctgtat gaaactgaga 480
tgttgtctat agctatgtct a 501

<210> SEQ ID NO 113
<211> LENGTH: 536
<212> TYPE: DNA
<213> ORGANISM: Homo sapiens
<220> FEATURE:
<221> NAME/KEY: misc_feature
<222> LOCATION: (54)..(57)
<223> OTHER INFORMATION: n is a, c, g, t or u
<220> FEATURE:
<221> NAME/KEY: misc_feature
<222> LOCATION: (60)..(71)
<223> OTHER INFORMATION: n is a, c, g, t or u
<220> FEATURE:
<221> NAME/KEY: misc_feature
<222> LOCATION: (73)..(76)
<223> OTHER INFORMATION: n is a, c, g, t or u
<220> FEATURE:

<221> NAME/KEY: misc_feature
<222> LOCATION: (79)..(83)
<223> OTHER INFORMATION: n is a, c, g, t or u
<220> FEATURE:
<221> NAME/KEY: misc_feature
<222> LOCATION: (85)..(87)
<223> OTHER INFORMATION: n is a, c, g, t or u
<220> FEATURE:
<221> NAME/KEY: misc_feature
<222> LOCATION: (89)..(91)
<223> OTHER INFORMATION: n is a, c, g, t or u
<220> FEATURE:
<221> NAME/KEY: misc_feature
<222> LOCATION: (93)..(94)
<223> OTHER INFORMATION: n is a, c, g, t or u
<220> FEATURE:
<221> NAME/KEY: misc_feature
<222> LOCATION: (96)..(96)
<223> OTHER INFORMATION: n is a, c, g, t or u

<400> SEQUENCE: 113
ggagaggctt cttgctgaat tttgattctg cagctgaaat ttaggacagt tgcnnnngtn 60
nnnnnnnnnn nannnntcnn nnntnnncnn ntnnantgtt taaaaattgt acaaaaggaa 120
aaaattagaa taagtactgg cgaaccatct ctgtggtctt gtttaaaaag ggcaaaagtt 180
ttagactgta ctaaatttta taacttactg ttaaaagcaa aaatggccat gcaggttgac 240
accgttggta atttataata gcttttgttc gatcccaact ttccattttg ttcagataaa 300
aaaaaccatg aaattactgt gtttgaaata ttttcttatg gtttgtaata tttctgtaaa 360
tttattgtga tattttaagg ttttcccccc tttattttcc gtagttgtat tttaaaagat 420
tcggctctgt attatttgaa tcagtctgcc gagaatccat gtatatattt gaactaatat 480
catccttata acaggtacat tttcaactta agtttttact ccattatgca cagttt 536

<210> SEQ ID NO 114
<211> LENGTH: 356
<212> TYPE: DNA
<213> ORGANISM: Homo sapiens

<400> SEQUENCE: 114
gactatttcc cctgagtggc cgtgttgtcc cagtgccctg gttcagtgtc tcctgagtgg 60
atgacaggtc ttcattctct atcttgaatg tattatggtt actaatagtt ttataatgga 120
ggtctaagaa ttaaagttgt gtgggagttt caggacaaag gaaggctaaa agtttgtcaa 180
gacgttgagc gtattttggt tacctatgag aagggttgtg acagtgtaca gtggcagctg 240
ttggccacgc tgcagaaatg agctggagct catgggtttt cagctacatt tttcataact 300
ttgtagtaca tccatcttga gtaaattaag ccacaatttg gtacctaggg tctcaa 356

<210> SEQ ID NO 115
<211> LENGTH: 498
<212> TYPE: DNA
<213> ORGANISM: Homo sapiens

<400> SEQUENCE: 115
ccctgtcagt gtcggagtgt ataagaatgc ttgtaaatac tgtaatatat ttattaatat 60
ttgaaaggca ttcattcagt ggacagtggg aattaactct cccaaggcaa gtgaaaatga 120
atgattgacg tacgttgatt taacaatctt actagatttt aattcttaag gatttcaaat 180
gaaaccagaa ggtggttatg taagaggctt aaaatgatct tatgtttaaa gagattctgt 240
tattagcacc atgaactcgt actatgaaat ttttaagcct tttatttttc taactatatt 300
actgtaggac tggatattag gtgtcatata ggaaacacaa aagttattgc tgtttgctaa 360
agcaaaatag cagaaaattt tgtatatgca aaactgttga aggaccatag agaaatgtgt 420
actactgacg gggcttttac taggcttcct gcgtgtgtaa aagtcgaggt attgctggca 480
ttcagggtga catgatgg 498

<210> SEQ ID NO 116
<211> LENGTH: 487
<212> TYPE: DNA
<213> ORGANISM: Homo sapiens
<220> FEATURE:
<221> NAME/KEY: misc_feature
<222> LOCATION: (257)..(257)
<223> OTHER INFORMATION: n is a, c, g, t or u

<400> SEQUENCE: 116
gccacaattt ggtacctagg gtctcaaact aaaatttatt tttataaatg aattttaaaa 60
gaaaaaatat ctacttcttt taaagttaga agaaaattaa cctgctgaca ggcaacattt 120
ttggggtgct ttctgcacta gttttccttg taaatgattt gagtgagtag gtttggtttc 180
tgacgaaagt agactggagg gtagcattgt atgcctcaaa tgtctcagtg tgtttggctc 240
atacgtgggc tatactntat tattttggta tgcttacaaa tgactaacca atcaaattgt 300
cattaatgtt tggaaaatct gttaatgcac atgcacaata atttcctgaa agccatagga 360
catgtctgta gtcagcacca cgatagcacc gtttcatgaa aggcatggcg gctgcatttc 420
ataccacatc aaaatacagt aacatttcta tactaaatta acagtaatac ctcaaaactg 480
ctccggt 487

<210> SEQ ID NO 117
<211> LENGTH: 411
<212> TYPE: DNA
<213> ORGANISM: Homo sapiens

<400> SEQUENCE: 117
acaacactta agcacactat ttctgttagt gtatatagtt ttcaaactaa caagcctgcg 60
atccttgtta gtgtagtgac tgcctcttta ggagtatggg gccctagggt gtccatatat 120
ttttacccca tgggtcattc tagtctaagg actactagta gaaccctcaa aaggtaattg 180
ctattatagg gacttactta ttggagactg gtaatataat aaaatattga aggagtggcc 240
atggtcttag caggttttag aatgaccttt taactccagt aactacttcc ttggtattgg 300
tatccttgat agagggaata taacatctgg cagtaatctc attcaggtta tactacctga 360
ctaaatttaa tcatactttc atgtatttgt ttcctcagtt ggacctaagt t 411

<210> SEQ ID NO 118
<211> LENGTH: 461
<212> TYPE: DNA
<213> ORGANISM: Homo sapiens

<400> SEQUENCE: 118
aaagtgaacc tgagtgccca gtctctgctg cacgatggca gccccctgtc cccattctgg 60
caggacacag cgttcatcac actctctcct aaagaagcaa agacctaccc ctgcaaaatc 120
tcctattccc agtacagcca gtacctgtca acagacaagc tgatccgcat cagtgccctg 180
ggtgaagaga aaagcagtcc tgagaaaatc ctggtgaaca agatcatcac cttatcttat 240
ccaagcatca cgattaatgt tctaggagca gccgttgtga accagccact ctccatacag 300
gtgatatttt caaacccccct ctcggagcag gttgaggact gtgtgctgac tgtggaagga 360

-continued agtggcctct tcaagaaaca gcagaaagtc ttccttggag tcctcaaacc ccaacaccaa 420
gcaagcatca ttctggagac cgtccccttc aagagtggac a 461

<210> SEQ ID NO 119
<211> LENGTH: 484
<212> TYPE: DNA
<213> ORGANISM: Homo sapiens

<400> SEQUENCE: 119
gcttcgggca tccaacgcaa tgatgaacaa caatgacctt gtgaggaaga ggaggcttgc 60
ggacctgact gggcccatca ttcccaagtg ccggagtggt gtctagtgtg tggcggtgga 120
gtccatgcct ttgaactgga tgtgttctat tgatgacctg tgctctgcag gggaaaccag 180
aaggcaaaat gctggcagca tgaaaccctt ttgtggttca gttctttatg cactaaggtt 240
ttaggttgac tagtggttgt agttgaaaat tttataaaat accgttaatg tgaagttttt 300
ctttagtcac agaagttgaa tctggttatt atttaaaaac tagaagcccc caaaccagca 360
gatcttactg aagatgatgt tccagcagca gcgacttagc cccaggagcc cagtttcaat 420
ggccttgctg tgtggtgttt caagtgcatt taaaatgtgt gacacagaaa cggcacactc 480
ttcc 484

<210> SEQ ID NO 120
<211> LENGTH: 504
<212> TYPE: DNA
<213> ORGANISM: Homo sapiens

<400> SEQUENCE: 120
agacaaattg ctgctgacct tacgcctgta tattaagcct ccgcaggatg ccggacaatg 60
gtgaagaaac tccagatatc aaggaattgg gaaatcctgg ccaaaccacc ccaagatgat 120
tacactgaaa tgtagtatta gtactgctgc cagatctctt tttaacatca tgtgcgtctc 180
ttgggatcca gcaaaagtgt taagccacaa tgcccttgtg ccttttaata taccacagtg 240
ccagttaaac taatattttt gtttgttgct tttgggagtt attttcatta gtgatttcag 300
caaatctcat gataaaggac aaggtcaaga actccagagc actgagcaga gaggctggtg 360
atgaaaaggt gaaggcctgc gcactgaact gtaaggcagt gggcagtaca gggtaactgg 420
aggcggggcc agggcctcag cgctatggaa gagtgtccac tgaggctgca catggcccag 480
gagtggcacc atgttgcagg gaca 504

<210> SEQ ID NO 121
<211> LENGTH: 389
<212> TYPE: DNA
<213> ORGANISM: Homo sapiens

<400> SEQUENCE: 121
gatagtcgga atagagccgc cccaactcag atcctacaac acgcaagttc cttcttgaac 60
cctggtgcct cctaccctat ggccctgaat ggtgcactgg tttaattgtg ttggtgtcgg 120
cccctcacaa atgcagccaa gtcatgtaat tagtcatctg gaacaaagac taaaaacagc 180
agagaattgc gggttctacc cagtcagaag atcacaccat ggagactttc tactagagga 240
cttgaaagag aactgagggg ccacaaaata aacttcacct tccattaagt gttcaagcat 300
gtctgcaaat taggagggag ttagaaacag tctttttcat cctttgtgat gaagcctgaa 360
attgtgccgt gttgccttat atgaatatg 389

<210> SEQ ID NO 122
<211> LENGTH: 427
<212> TYPE: DNA
<213> ORGANISM: Homo sapiens
<220> FEATURE:
<221> NAME/KEY: misc_feature
<222> LOCATION: (81)..(81)
<223> OTHER INFORMATION: n is a, c, g, t or u
<220> FEATURE:
<221> NAME/KEY: misc_feature
<222> LOCATION: (86)..(86)
<223> OTHER INFORMATION: n is a, c, g, t or u
<220> FEATURE:
<221> NAME/KEY: misc_feature
<222> LOCATION: (117)..(117)
<223> OTHER INFORMATION: n is a, c, g, t or u
<220> FEATURE:
<221> NAME/KEY: misc_feature
<222> LOCATION: (176)..(176)
<223> OTHER INFORMATION: n is a, c, g, t or u
<220> FEATURE:
<221> NAME/KEY: misc_feature
<222> LOCATION: (258)..(258)
<223> OTHER INFORMATION: n is a, c, g, t or u
<220> FEATURE:
<221> NAME/KEY: misc_feature
<222> LOCATION: (274)..(274)
<223> OTHER INFORMATION: n is a, c, g, t or u
<220> FEATURE:
<221> NAME/KEY: misc_feature
<222> LOCATION: (359)..(359)
<223> OTHER INFORMATION: n is a, c, g, t or u
<220> FEATURE:
<221> NAME/KEY: misc_feature
<222> LOCATION: (382)..(382)
<223> OTHER INFORMATION: n is a, c, g, t or u

<400> SEQUENCE: 122
ctgtgggtcg tggataagga gcttattcag gtttcctgcc ctagctatta gctccacttc 60
acatgctgga gaccggcgta nggacngatg tattcatcct ggtgttactg aaaaacnggt 120
gtgatcctgt tactgatact ataagtgacc taaaatgtca ctgttcaaat tagccngtgt 180
tctaacaaac taaactcttc aaatgcttgg aaagatacta caaagccaat ctttatagaa 240
ttgggccaag ataaatcnat gttgttttgc atgnctattg ttaagctcca aaggttcact 300
gtgtttctgc cgctgtcctg gagttgtcac cactgactgg gcaaggcttc ttgggcatng 360
atgtagaact gttgtccttt tnccactaac agttatcttt gactctcttg cctgttatgc 420
ttacaaa 427

<210> SEQ ID NO 123
<211> LENGTH: 241
<212> TYPE: DNA
<213> ORGANISM: Homo sapiens

<400> SEQUENCE: 123
accatcgctg gtggtatccc agggtccctg ctcaagtttt ctttgaaaag gagggctgga 60
atggtacatc acataggcaa gtcctgccct gtatttaggc tttgcctgct tggtgtgatg 120
taagggaaat tgaaagactt gcccattcaa aatgatcttt accgtggcct gccccatgct 180
tatggtcccc agcatttaca gtaacttgtg aatgttaagt atcatctctt atctaaatat 240
t 241

<210> SEQ ID NO 124
<211> LENGTH: 392
<212> TYPE: DNA
<213> ORGANISM: Homo sapiens

<400> SEQUENCE: 124

```
ggggctatac tccatccaaa tatgcagtgg aaggtttcaa tgacagctta agacgggaca     60

tgaaagcttt tggtgtgcac gtctcatgca ttgaacgtct agacaaactg aaaggcaata    120

aatcctatgt gaacatggac ctctctccgg tggtagagtg catggaccac gctctaacaa    180

gtctcttccc taagactcat tatgccgctg gaaaagatgc caaaattttc tggatacctc    240

tgtctcacat gccagcagct ttgcaagact ttttattgtt gaaacagaaa gcagagctgg    300

ctaatcccaa ggcagtgtga ctcagctaac cacaaatgtc tcctccaggc tatgaaattg    360

gccgatttca agaacacatc tccttttcaa cc                                  392
```

<210> SEQ ID NO 125
<211> LENGTH: 512
<212> TYPE: DNA
<213> ORGANISM: Homo sapiens

<400> SEQUENCE: 125

```
ggggctatac tccatccaaa tatgcagtgg aaggtttcaa tgacagctta agacgggacc     60

tgaaagcttt tggtgtgcac gtctcatgca ttgaaccagg attgttcaaa acaaacttgg    120

cagatccagt aaaggtaatt gaaaaaaaac tcgccatttg ggagcagctg tctccagaca    180

tcaaacaaca atatggagaa ggttacattg aaaaaagtct agacaaactg aaaggcaata    240

aatcctatgt gaacatggac ctctctccgg tggtagagtg catggaccac gctctaacaa    300

gtctcttccc taagactcat tatgccgctg gaaaagatgc caaaattttc tggatacctc    360

tgtctcacat gccagcagct ttgcaagact ttttattgtt gaaacagaaa gcagagctgg    420

ctaatcccaa ggcagtgtga ctcagctaac cacaaatgtc tcctccaggc tatgaaattg    480

gccgatttca agaacacatc tccttttcaa cc                                  512
```

<210> SEQ ID NO 126
<211> LENGTH: 502
<212> TYPE: DNA
<213> ORGANISM: Homo sapiens
<220> FEATURE:
<221> NAME/KEY: misc_feature
<222> LOCATION: (224)..(224)
<223> OTHER INFORMATION: n is a, c, g, t or u
<220> FEATURE:
<221> NAME/KEY: misc_feature
<222> LOCATION: (238)..(238)
<223> OTHER INFORMATION: n is a, c, g, t or u
<220> FEATURE:
<221> NAME/KEY: misc_feature
<222> LOCATION: (269)..(269)
<223> OTHER INFORMATION: n is a, c, g, t or u

<400> SEQUENCE: 126

```
aagcaggctt gtgctttata ccccatttga tttcgatgta cagtctcaat tttgtattta     60

atgatttttg tgtatccagt atgcacgtta acagcgtgtc aactttcatt tgaaagtggg    120

tttcaattta ctttttaaac agtgtttatg acgagacctc agatgtgttg acgtaagctc    180

tatctgcaat gtttttgtgt agagtggcga ttgaatgctg cccngggtca gtgtatcnta    240

attccccgag accctcgttt gatagtgcnt cttgtaatat ttcttcaagt gagtggcatg    300

tgggttgtga tattgaccat gtgattatgg acatcgatat gaaaaataaa taaataaaac    360

taaggaaccc tggaaactac cagtgggcat gtattagcca gtcattgtaa cctcgtgtct    420

agtagaacaa tgtacaaggt atgtacagtt cataaatttg ttgtcatgtg tatgagaagt    480

actttgtgct gatcgcctta tt                                             502
```

<210> SEQ ID NO 127
<211> LENGTH: 536
<212> TYPE: DNA
<213> ORGANISM: Homo sapiens
<220> FEATURE:
<221> NAME/KEY: misc_feature
<222> LOCATION: (26)..(26)
<223> OTHER INFORMATION: n is a, c, g, t or u
<220> FEATURE:
<221> NAME/KEY: misc_feature
<222> LOCATION: (64)..(64)
<223> OTHER INFORMATION: n is a, c, g, t or u
<220> FEATURE:
<221> NAME/KEY: misc_feature
<222> LOCATION: (124)..(124)
<223> OTHER INFORMATION: n is a, c, g, t or u

<400> SEQUENCE: 127
aaaatgctat tagtccgtcg tgcttnattt gtttttgtcc ttgaataagc atgttatgta 60
tatngtctcg tgtttttatt tttacaccat attgtattac acttttagta ttcaccagca 120
taancactgt ctgcctaaaa tatgcaactc tttgcattac aatatgaagt aaagttctat 180
gaagtatgca ttttgtgtaa ctaatgtaaa aacacaaatt ttataaaatt gtacagtttt 240
ttaaaaacta ctcacaacta gcagatggct taaatgtagc aatctctgcg ttaattaaat 300
gcctttaaga gatataatta acgtgcagtt ttaatatcta ctaaattaag aatgacttca 360
ttatgatcat gatttgccac aatgtcctta actctaatgc ctggactggc catgttctag 420
tctgttgcgc tgttacaatc tgtattggtg ctagtcagaa aattcctagc tcacatagcc 480
caaaagggtg cgagggagag gtggattacc agtattgttc aataatccat ggttca 536

<210> SEQ ID NO 128
<211> LENGTH: 304
<212> TYPE: DNA
<213> ORGANISM: Homo sapiens

<400> SEQUENCE: 128
cttttctgta atctgtttat ctcccactta atggaaaggc aaaggggtac cccaaatcca 60
gaggtgccta catttcaggc agccttggag tattttaaaa ggaaaacatt ctttactttt 120
atatgacatt cttatactgc tgtctcaaat cctttttcat ttcagagctc ttgtctcaga 180
gatgtgtgtt ctttttgtca gagatatggt tgatgagaat cttaaatgct tgttttgcac 240
tatcacttag tacctgtttg accaaggtgt taagggatag tacctcccat cagcagagaa 300
actg 304

<210> SEQ ID NO 129
<211> LENGTH: 408
<212> TYPE: DNA
<213> ORGANISM: Homo sapiens

<400> SEQUENCE: 129
gatcaatgct tcgaacttct actttaacaa aaccaagggc ttttactgcc tgcgggacag 60
cggccgggac cgctgcttac atgagtccaa aggccgggcg cacccccaag tcgatcccaa 120
actactcaat aaactgcacg aatattttca tgagccaaat aagaagttct tcgagcttgt 180
tggcagaaca tttgactggc actgatttgc aataagctaa gctcagaaac tttcctactg 240
taagttctgg tgtacatctg aggggaaaaa gaattttaaa aaagcattta aggtataatt 300
tatttgtaaa atccataaag tacttctgta cagtattaga ttcacaattg ccatatatac 360
tagttatatt tttctacttg ttaaatggag ggcattttgt attgtttt 408

<210> SEQ ID NO 130
<211> LENGTH: 399
<212> TYPE: DNA
<213> ORGANISM: Homo sapiens

<400> SEQUENCE: 130
ggatgtcaaa tagtcacagt tctaagtagt tggaaacaaa attgacgcat gttaatctat 60
gcaaagagaa aggaaaggat gaggtgatgt attgactcaa ggttcattct tgctgcaatt 120
gaacatcctc aagagttggg atggaaatgg tgatttttac atgtgtcctg gaaagatatt 180
aaagtaattc aaatcttccc caaaggggaa aggaagagag tgatactgac ctttttaagt 240
catagaccaa agtctgctgt agaacaaata tgggaggaca aagaatcgca aattcttcaa 300
atgactatta tcagtattat taacatgcga tgccacaggt atgaaagtct tgccttattt 360
cacaatttta aaaggtagct gtgcagatgt ggatcaaca 399

<210> SEQ ID NO 131
<211> LENGTH: 268
<212> TYPE: DNA
<213> ORGANISM: Homo sapiens
<220> FEATURE:
<221> NAME/KEY: misc_feature
<222> LOCATION: (172)..(173)
<223> OTHER INFORMATION: n is a, c, g, t or u
<220> FEATURE:
<221> NAME/KEY: misc_feature
<222> LOCATION: (176)..(176)
<223> OTHER INFORMATION: n is a, c, g, t or u

<400> SEQUENCE: 131
cagtggctct attctacctg taagaaaatg atacaaaacc acctaagata ttttgaagcc 60
tgacaaatca gcttcatgga aaaaggtaaa aaatgcattt ttcaaccgaa agggcagatc 120
caatagaaga cccgctcctt aaataaacat aaaatgtaaa aagttggaaa annaanagta 180
atgttccatc tggaaactga acttttgtcc ttgaacttgt gttggcacca agcctcatac 240
acagtgagct caataactgt tgggacaa 268

<210> SEQ ID NO 132
<211> LENGTH: 433
<212> TYPE: DNA
<213> ORGANISM: Homo sapiens

<400> SEQUENCE: 132
ggcttattga cttgcacggt tgggcagata atccagattt acctaagatt gggtaaaaaa 60
gtcatctgtg actttgctgg cagggcattt gctaagtgga gtacaggatc taaaagggtt 120
ttcttagaaa gggcaatatt gtccaatgaa gtaagcagaa ggactctggg ttagaagcat 180
ctgcacaaaa actggtgaga cctactctcc actgctctgc agctggatgg ctgatggcag 240
gctgagcagt ggggaagcag gttttaacaa cagggagtcc ttccaggtca ctgtatattg 300
agaagaaaca taaaactatt gtctgttaca ttccgaggtc agccttcttc ttaacgtttt 360
ataatatgca aatgccagct tctggaaagc aagtatcatc atgtaccaaa tgctttatac 420
accatcacat tca 433

<210> SEQ ID NO 133
<211> LENGTH: 497
<212> TYPE: DNA
<213> ORGANISM: Homo sapiens

<400> SEQUENCE: 133

```
cttttattt ctatgtgtgc cacacacaat gcagtattaa tggcaaccag gtaaatattg     60

atttattttt taaagctttt cttcagtgtt ttgtcaacca tttcaaagtg tctcccaaaa    120

aaggatgctg aagagcaatt gctcccttaa gcaacagatt catatttacc ctgggttaat    180

acaacaaaag gcctgtataa ttgtcttttc attgttaaca cccaaaatag catctatcta    240

gacagtatcc ccaaagaatt tggaaaatct gatggtgtga gcagcagccg ttagtatcag    300

ggtttcccat tcttggacag tccgaggctg tgacctgtta gataattaga ttatacttga    360

actggaccag agtttgtttt ttgaatttat gagaaaaacc aaaacactaa gttaagtttg    420

aacttgtaaa gtattgaaat ttgttgagtg tcctataaat tgtcactact tttcctgatc    480

tgtataactg actgcaa                                                   497
```

<210> SEQ ID NO 134
<211> LENGTH: 533
<212> TYPE: DNA
<213> ORGANISM: Homo sapiens

<400> SEQUENCE: 134

```
ctgccttaga ttccgtgggt catgagccat gagtcctggg acatctgagg attgggattc     60

tttgttcacc ccgcagatag ttaatgaatg gtctgccctg ggcaagatgg aggtgggggc    120

tgggggaata tgcatgttgc agaagccggc gtttttatta gcggtcctga gtaatttccc    180

ttggcaaaat tcccagtttt gccactcgct ggagccagat cctgggagct gtcagcaagg    240

agcaggtaag tgagcagtta tggacagcac tttccatgtg gtgcttccga ccctggctgt    300

cagagtgaaa tgtaaagtca gggctctgta cagttttgcc atttcactgt tctgctttaa    360

gcttagctta ttagaactct tggtggaggg tgcgtacaca cattccagaa aaggcttcac    420

tcgctgggaa cgtcaaccca gcgagaaagg aggggaagcc ccttctccgg ggaccttatc    480

tgtggactca gggatgatgg tgtttattgc aaatgcacaa tctttttccc att           533
```

<210> SEQ ID NO 135
<211> LENGTH: 485
<212> TYPE: DNA
<213> ORGANISM: Homo sapiens
<220> FEATURE:
<221> NAME/KEY: misc_feature
<222> LOCATION: (55)..(55)
<223> OTHER INFORMATION: n is a, c, g, t or u
<220> FEATURE:
<221> NAME/KEY: misc_feature
<222> LOCATION: (57)..(83)
<223> OTHER INFORMATION: n is a, c, g, t or u
<220> FEATURE:
<221> NAME/KEY: misc_feature
<222> LOCATION: (123)..(123)
<223> OTHER INFORMATION: n is a, c, g, t or u
<220> FEATURE:
<221> NAME/KEY: misc_feature
<222> LOCATION: (173)..(173)
<223> OTHER INFORMATION: n is a, c, g, t or u
<220> FEATURE:
<221> NAME/KEY: misc_feature
<222> LOCATION: (213)..(231)
<223> OTHER INFORMATION: n is a, c, g, t or u
<220> FEATURE:
<221> NAME/KEY: misc_feature
<222> LOCATION: (380)..(380)
<223> OTHER INFORMATION: n is a, c, g, t or u
<220> FEATURE:
<221> NAME/KEY: misc_feature
<222> LOCATION: (382)..(383)

<223> OTHER INFORMATION: n is a, c, g, t or u
<220> FEATURE:
<221> NAME/KEY: misc_feature
<222> LOCATION: (417)..(417)
<223> OTHER INFORMATION: n is a, c, g, t or u

<400> SEQUENCE: 135
tccgagctaa aatcccaggg accggagccc tggcctctgc agcagccgca gtctncnnnn 60
nnnnnnnnnn nnnnnnnnnn nnnacggtgt ctctgcccgc aggacgcctg cccccagccc 120
ccngcagccc tctggccccc tccatctctt gtccgttccc acccaccccc ctncctcggc 180
ccgagccttt tcccggtggg tgtcaggatc acnnnnnnnn nnnnnnnnnn nctaattacc 240
tgagcgacca ggactacatt tcccaagagg ctctgctcca ggagtccagg aaagacgagg 300
caccttggcc gcggggcctg ctgggacttg tagttgccta gacagggcac caccctgcac 360
ttccggaccc gccgctggan gnnccgtgag gcgttggtgt ctcctggatg ctactanccc 420
caacgccggg gctttgcatg gggcccaggg gaggcctgag cttggattta cactgtaata 480
aagac 485

<210> SEQ ID NO 136
<211> LENGTH: 287
<212> TYPE: DNA
<213> ORGANISM: Homo sapiens

<400> SEQUENCE: 136
gattctgtgg tagactcagt gctttcagag tccagagctt gacttgggtt agtggcctta 60
atgaagtgct aaatttgctc tttaccgcga gactgatcag aagaagcaaa aggggaaagg 120
gggctagagg tccactcgca ccttttacat cagacaagag gaggactgtg ccagaaatct 180
gtgcatgaaa caccatctgc tcttcatgca gggaggggtc aaccgtgtga acgtgcagag 240
attactcgag ccttctttgc caaaaatatg cattcttccc agctgta 287

<210> SEQ ID NO 137
<211> LENGTH: 508
<212> TYPE: DNA
<213> ORGANISM: Homo sapiens

<400> SEQUENCE: 137
tgaagtgcca gcactcatcc atcaatcaat cacccacaag gaaaaatagc aacagtacaa 60
cggggtggct tttatgggat ttactcatgg gcatagggaa tagcggctca aatgtagttc 120
tgacatgaaa agcaaggtgc tgatattatt ttttatgatg ggaggatcat aaagtgaatt 180
gagaacagtg aggtctgtct ttgcttaacc tattcaacca gaaatgaatg gagctcgact 240
ggaaaggaac agtcttcaga tgggttaaga ttgaagggtg gactggactc tactgagcac 300
cgtccttcaa caaggaaatt ctattaaagg aaaatcaatg cattagtatt ggggttcttg 360
tagcttgtta aaaattgtct gctccaatcc agggttatta ggccaaagtt acataattca 420
gatctcactg caaccatcca aaagtggatt ctcgagccct tgctccaatg gggggaggag 480
atcaatacaa ttccccaatt tccatgga 508

<210> SEQ ID NO 138
<211> LENGTH: 515
<212> TYPE: DNA
<213> ORGANISM: Homo sapiens
<220> FEATURE:
<221> NAME/KEY: misc_feature
<222> LOCATION: (382)..(382)
<223> OTHER INFORMATION: n is a, c, g, t or u
<220> FEATURE:
<221> NAME/KEY: misc_feature
<222> LOCATION: (393)..(393)
<223> OTHER INFORMATION: n is a, c, g, t or u
<220> FEATURE:
<221> NAME/KEY: misc_feature
<222> LOCATION: (402)..(402)
<223> OTHER INFORMATION: n is a, c, g, t or u

<400> SEQUENCE: 138
aagtcttgca tacctagtgc acagtttgga gacgcaagga tagatctgtt tactctagtt 60
gaacattttc tatacaattg aaagcaacct ataatagata aatccatcat tgcatttaaa 120
caatgaattt ccttattctc aaaggacaaa tacgtctgga ttatgtggta aattgctact 180
cagctatggt gaaatattta tactattcta ggcacaacac taggaactag gtgattctga 240
aacaaaagga atattttctg ttgttgcttt aattaccaag gttatttttt tttaatctca 300
acactgacaa aatgaaacca aatatctctt cctcaccatt tctcaaggag gctgcctgtt 360
ggaattgttt tggaaatttt gnacatgatc ccntaaattc ancattggga ttaaaaaaaa 420
aaaaaacttc ttatttacct cctaagggaa ggttgccctt atgccacata taataccaaa 480
ttgctttttt atgggctgcc ataacctgaa gggaa 515

<210> SEQ ID NO 139
<211> LENGTH: 388
<212> TYPE: DNA
<213> ORGANISM: Homo sapiens

<400> SEQUENCE: 139
tgcagatttt attctcacct gggccatttg cagatgagac tgtagtttgc agatgagact 60
gtagtttgca gatggcgtgg aagcattcat caggggagat aaccataaag gatttggcct 120
aattaccata ctcaattgtc agtttacgtg gttttgtgaa tactggcaaa agcaattgtt 180
tttaaattaa caatggagag aatgataaga tgagggaagg aaaaggcatt cattattgac 240
ttacatgtca gtaaggtctg cttttatttc tatgtactcc tgtttgccaa gctcaataat 300
ggacaaagga tacaaacaca cacacatcta ctattttaga taaatgtact gttatatata 360
tatgtaaact actattgctc tctttata 388

<210> SEQ ID NO 140
<211> LENGTH: 544
<212> TYPE: DNA
<213> ORGANISM: Homo sapiens

<400> SEQUENCE: 140
taggctttac tgtcttatgc ttatggacat tgtatatttg tattttatga ccaagtagac 60
caagtcagaa agatctctct cgagcgcacc ataaacctgc agagagaagt ctcgaaaggc 120
tccaccaagg taccaagggc agctgctttt cctgtctttt gtgcatgggc gacccattac 180
agtatgagat aagattgagt tctgatgcgt taaacggagg tggcagaaat ttgtcaagaa 240
ggccttatcc atttcgattg tgtgacagat tgaaatttat tgtttacatt ggggaatgta 300
tctcaaattt ttaaatagaa gagtaataaa cagactttaa agcaaatatt aagattttta 360
ctcattcaag gcaagtaaat gaatggaatt atctgagctc tatggcactg gttgtttaga 420
gtgactgatg aagtgcacct ttcaaaaaca tttttgatgc catcaccagc ctactgcaga 480
agtgcagggc acagtaaaca ccatgtatta ttgaagatga tctgttttgt atgtatcctt 540
gtca 544

<210> SEQ ID NO 141
<211> LENGTH: 392
<212> TYPE: DNA
<213> ORGANISM: Homo sapiens
<220> FEATURE:
<221> NAME/KEY: misc_feature
<222> LOCATION: (198)..(198)
<223> OTHER INFORMATION: n is a, c, g, t or u

<400> SEQUENCE: 141
atgtttcttg ttagccatga ccctataaga aataaactgc actgcaaaat gataaacatg 60
atatcaatca ttacatggga aggcactata taaagaataa taccttaggt taaggccaca 120
taaatattta tcaggtgcct tttctgcgga ggactctgaa gggatactaa actgcattta 180
gctgcatgca actgaaanta cttttaccta cattgtctct tataaacatt ataactactc 240
tttgagaaag tgtttactat ggactgaatt gtctccccat ccccccaaat tcatatattg 300
aagccataaa ccccaatatg actctattcc tagacaggac ttataagagg taattaaggt 360
taaatgaggt cattaggatg ggttcctaac tg 392

<210> SEQ ID NO 142
<211> LENGTH: 508
<212> TYPE: DNA
<213> ORGANISM: Homo sapiens

<400> SEQUENCE: 142
ttcctttctc actgccttga gagtgaccca aagatgagat ggaccgccag ccagctcctc 60
gaccattcgt ttgtcaaggt ttgcacagat gaagaatgaa gcctagtaga atatggactt 120
ggaaaattct cttaatcact actgtatgta atatttacat aaagactgtg ctgagaagca 180
gtataagcct ttttaacctt ccaagactga agactgcaca ggtgacaagc gtcacttctc 240
ctgctgctcc tgtttgtctg atgtggcaaa aggccctctg gagggctggt ggccacgagg 300
ttaaagaagc tgcatgttaa gtgccattac tactgtacac ggaccatcgc ctctgtctcc 360
tccgtgtctc gcgcgactga gaaccgtgac atcagcgtag tgttttgacc tttctaggtt 420
caaaagaagt tgtagtgtta tcaggcgtcc cataccttgt ttttaatctc ctgtttgttg 480
agtgcactga ctgtgaaacc tttacctt 508

<210> SEQ ID NO 143
<211> LENGTH: 502
<212> TYPE: DNA
<213> ORGANISM: Homo sapiens

<400> SEQUENCE: 143
ctggagtctg ggtgtgttg tcatagagat ggtgactggc aaggtttgca cagatgaaga 60
atgaagccta gtagaatatg gacttggaaa attctcttaa tcactactgt atgtaatatt 120
tacataaaga ctgtgctgag aagcagtata agccttttta accttccaag actgaagact 180
gcacaggtga caagcgtcac ttctcctgct gctcctgttt gtctgatgtg gcaaaaggcc 240
ctctggaggg ctggtggcca cgaggttaaa gaagctgcat gttaagtgcc attactactg 300
tacacggacc atcgcctctg tctcctccgt gtctcgcgcg actgagaacc gtgacatcag 360
cgtagtgttt tgacctttct aggttcaaaa gaagttgtag tgttatcagg cgtcccatac 420
cttgttttta atctcctgtt tgttgagtgc actgactgtg aaacctttac ctttttttgtt 480 gttgttggca agctgcaggt tt 502

<210> SEQ ID NO 144
<211> LENGTH: 500
<212> TYPE: DNA
<213> ORGANISM: Homo sapiens
<220> FEATURE:
<221> NAME/KEY: misc_feature
<222> LOCATION: (299)..(299)
<223> OTHER INFORMATION: n is a, c, g, t or u
<220> FEATURE:
<221> NAME/KEY: misc_feature
<222> LOCATION: (456)..(456)
<223> OTHER INFORMATION: n is a, c, g, t or u

<400> SEQUENCE: 144

```
ttgtgtgtaa tttcatggtg gcctagtgtt gtggtgcttc tggtaatggt aatagaagct     60

caactatttt tttgtggatt tcagttttta tcatcagaag tcctagacag tgacatttct    120

taatggtggg agtccagctc atgcatttct gattatacaa aacagtttgc agtaggttat    180

ttgtcatttc agtttttac tgaaatttga gctaaacatt tttacatgta aatacttgta    240

tttaccaaag atttaaatca gttgattaat taattaactc aaatactgtg aactatctnt    300

aaaacactag aaaaaagaaa tgttagtatc tcaattacac caactgtgca aatgaacttt    360

gataaaatag aaataatcta cattggcctt tgtgaaatct ggggaagagc tttaggattc    420

tagtagatgg atactgaata ctcaggccca cttaanttat taatgtatac attgtgtttt    480

tgtctttatg ctatgtacag                                                500
```

<210> SEQ ID NO 145
<211> LENGTH: 450
<212> TYPE: DNA
<213> ORGANISM: Homo sapiens

<400> SEQUENCE: 145

```
gctggtatca gaacagcttc cctcactgtg tacagaacgc aagaagggaa taggtggtct     60

gaacgtggtg tctcactctg aaaagcagga atgtaagatg atgaaagaga caatgtaata    120

ctgttggtcc aaaagcattt aaaatcaata gatctgggat tatgtggcct taggtagctg    180

gttgtacatc tttccctaaa tcgatccatg ttaccacata gtagttttag tttaggattc    240

agtaacagtg aagtgtttac tatgtgcaag ggtattgaag ttcttatgac cacagatcat    300

cagtactgtt gtctcatgta atgctaaaac tgaaatggtc cgtgtttgca ttgttaaaaa    360

tgatgtgtga aatagaatga gtgctatggt gttgaaaact gcagtgtccg ttatgagtgc    420

caaaaatctg tcttgaaggc agctacactt                                     450
```

<210> SEQ ID NO 146
<211> LENGTH: 386
<212> TYPE: DNA
<213> ORGANISM: Homo sapiens

<400> SEQUENCE: 146

```
gtagcatgtt gtcagtggcc aaggctacac agaaggctcc ctgctgcccg gagcaggtac     60

atccaccaga gcaaagggaa ccacttttat tttgcatgag tttggtaact gattactctc    120

ccctcaaaga aaagacattc aggtgtttct caacgacatc ttctgtccag caagctcggt    180

ttgaatacgt cacttaccag tgccattgca ggacccaaat tcacagttca taaaagatgt    240

gaccactaca tgtaaaaata gcattctact tgatcttaca gtatgtatgt atgtatgtat    300

ggagacatat gtgtgtgtgt ggatgtctac atggttaatg gaaagcactg tgctctgaag    360

tggatcagtc tcaagtgtct ggtaac                                         386
```

<210> SEQ ID NO 147
<211> LENGTH: 487
<212> TYPE: DNA
<213> ORGANISM: Homo sapiens
<220> FEATURE:
<221> NAME/KEY: misc_feature
<222> LOCATION: (296)..(296)
<223> OTHER INFORMATION: n is a, c, g, t or u

<400> SEQUENCE: 147
tataaggtaa ctctttagtc ctccatttag cacattttaa atcctccaaa gaataagtat 60
catgtgatta ttttagcttt acaaaaaaaa agttgaatgg cgttttattt tcatggccta 120
taagcaggta ccttagtagg gcagatatag gaaaaacaaa ttagagcaaa acaaatcctc 180
tacaaatcca aggcaggaaa agtggtggca gagtgactca ttctcctgtc cctcccatca 240
ggtcaaatca ggaggctgca gtgaatgcct gttctttgaa tgtgtagcag ttgttncctg 300
taactcttta aaacttggct ataggctgtt tagcacagta cagattaaag atacagttac 360
gtaaacagca aagtaatttt atagtgcttc atccatttat catgctttgg tttgctaatt 420
ttttcacata cctttttcta tcacagtctg ttgcttttgt acacatttct catattgggg 480
ttcgaca 487

<210> SEQ ID NO 148
<211> LENGTH: 400
<212> TYPE: DNA
<213> ORGANISM: Homo sapiens
<220> FEATURE:
<221> NAME/KEY: misc_feature
<222> LOCATION: (120)..(120)
<223> OTHER INFORMATION: n is a, c, g, t or u
<220> FEATURE:
<221> NAME/KEY: misc_feature
<222> LOCATION: (373)..(375)
<223> OTHER INFORMATION: n is a, c, g, t or u

<400> SEQUENCE: 148
gcagtatgag tttcaggtat gtacatgtta tgtgtgtgtg tgagagacac acacaaacac 60
atttcaaaca tgttttatgt ttaagctcaa tattcaaaca cagaaatata acatctattn 120
cttaatatgt tttatgtaag tacagcagca gcattattaa atactgtatt tctatggtga 180
ttgaaaatta gtaggcagag aatttttgta atggttctta ataatttttg taatagtaaa 240
tgattacttt ttgtttagta tagttttata atctatacat gaataaagtg gatatttcta 300
ttcatataga aatgtgattt actctcatgt acttatctac atgctaaaac cataagttat 360
caattttagt tcnnngccaa ggcactttta ctgaataaaa 400

<210> SEQ ID NO 149
<211> LENGTH: 518
<212> TYPE: DNA
<213> ORGANISM: Homo sapiens
<220> FEATURE:
<221> NAME/KEY: misc_feature
<222> LOCATION: (199)..(199)
<223> OTHER INFORMATION: n is a, c, g, t or u

<400> SEQUENCE: 149
gtatcctata actatcaact tcccaggttg aagacgatgt gttgagtttc ctactgattg 60
attgattcct gtcctcccca gtgtttccgt cactggttca ctaaaacagt atttatatag 120
ctccactggc tctaaagctc ttagtccttc taatattttg gattttacaa gtaaaaatgg 180
aaaaaaaata gaaaagagnc aatcaaatgc ctggagctta aaacaaagta tgtgcaacct 240

```
accatctcac ttgaaattta ataaaataat aagtaattat gtaaatataa catagagtta    300

tagatttata ttttgttcat aacacatagt gtaatataag ttgtatattt tcatgttttt    360

ggttttatgt tatcattcat gccacaataa aaataaaaca ggagtttatg tgctcttaaa    420

aaaaagatgt gggttgccac caacctgttt ttcgtttttg ttttttgttt attttatttt    480

atttttttgc attctccttt ttcagtatta ctgccatg                            518


<210> SEQ ID NO 150
<211> LENGTH: 343
<212> TYPE: DNA
<213> ORGANISM: Homo sapiens

<400> SEQUENCE: 150

gtttcagtca atgatgggcc acatgtagat ggtggtcccg taagattata ataccttatt     60

ttaactgtac cttttctatg tttagatgtg tttagatacc attgtgttac aatggcctga    120

agcattcagt acagtcacat gcgagcaggt atgcagccta ggagcaatag gccacaccac    180

acagcctagg tgtgcggcag gtgtagcgca ctctgatgcc tgcacgacga caaaatcaac    240

taacagcaaa ctcctcagac cgtatcccca tcattaagca acacatgact gcagtttctt    300

tctttgcttc taggctcagc ctacaaaagc ttgctgctca tgc                      343


<210> SEQ ID NO 151
<211> LENGTH: 388
<212> TYPE: DNA
<213> ORGANISM: Homo sapiens
<220> FEATURE:
<221> NAME/KEY: misc_feature
<222> LOCATION: (172)..(172)
<223> OTHER INFORMATION: n is a, c, g, t or u

<400> SEQUENCE: 151

gcctgatagt gctgaatttc tgaattgacc ttcatcttat ttactcaata atattcattt     60

gacaaatact tattaagtgc atatatgtgt caggaactgt actagatgct gaggatatag    120

cagtaagcgc aacagaccaa gctaacagct tagtaaaggg tgaggtaaaa cnaaaacaaa    180

aaagtattca aaaaaataaa ctaattttta tcttaattta aaaaattaca aatttttaaa    240

aatcacaaat tggtatccat gtataattca tttccgtgca ttttcttgtg tgaagaaagc    300

tcagtaaaag tatttcttag gtttctgtaa ttctagttct ctactcgatt ttcttctgca    360

attttctgag ccagaaccct tcttagaa                                       388


<210> SEQ ID NO 152
<211> LENGTH: 493
<212> TYPE: DNA
<213> ORGANISM: Homo sapiens

<400> SEQUENCE: 152

cccccatgtt acctggactg gaacagactg tgaatatagc agaaggttcc aagaactctg     60

gtgtctgacc tagaagaggc acagttctct ctactggaaa gaaaacgatg tagccgattg    120

cacaagggtg ccaagggaag acccaggatg gcccatcaaa ggaacctggg ggaggatgca    180

ggaggctgaa gggatgcacc tggcatttct ctcactgtgc tcttaccgca tcagcaaccc    240

ccaacttttg ggcctactct gccccccatg cgtgaatacc ctgcttggat gctgtgcttt    300

tccggtttgt ctctaagccc ctttctccag ggcatgttgg tttccctggc ctctcagtgt    360

cctaactgga gcccagagtg ccttgttctg agccaggaga cggctgagca ctggccctcc    420
```

acacctaagc gtcctttaca ttaacttatt ggtcttgtat aacacctggt gccattgcca 480
agtggctgtg tcc 493

<210> SEQ ID NO 153
<211> LENGTH: 398
<212> TYPE: DNA
<213> ORGANISM: Homo sapiens
<220> FEATURE:
<221> NAME/KEY: misc_feature
<222> LOCATION: (141)..(141)
<223> OTHER INFORMATION: n is a, c, g, t or u

<400> SEQUENCE: 153
gggtcaaccc caggagtatt tgcagaaggc ccagcacagt ggggggtatt ggctgcaggg 60
cagggaaggc attgccgact agataaccgt gtgagcttgg actgagcgtt ggtggttctt 120
cccaaaggaa aggaatttct ncccggcctg ccaggtctct gggccttcag cgcgggtcct 180
ggtgctgcgg ccacaccacc ctggggtgct cattgacaga gctgccataa tgaacttgaa 240
aggacgggaa tcacgaggga agctggggct cccctgccca caggagagga tccccgttct 300
tcaagcttct ctgctcagtg tctactaacg accgacattt gctaatgtaa ataatagtaa 360
attattgaga attctaattc ttttacacag tctgtttt 398

<210> SEQ ID NO 154
<211> LENGTH: 380
<212> TYPE: DNA
<213> ORGANISM: Homo sapiens
<220> FEATURE:
<221> NAME/KEY: misc_feature
<222> LOCATION: (161)..(161)
<223> OTHER INFORMATION: n is a, c, g, t or u
<220> FEATURE:
<221> NAME/KEY: misc_feature
<222> LOCATION: (173)..(173)
<223> OTHER INFORMATION: n is a, c, g, t or u

<400> SEQUENCE: 154
gtaatgtaca tatgcatatt gtctatgtac tatatacaca ttgtttataa tattgttatt 60
acagtttgtc attcacctga aaggagaagg aaaagtacga aaggtttctc tgcttgggaa 120
aaggtgaatg ttgttatatc aagaacgatt acacacatgg ntctcataca tgnttttaga 180
acattgttct tctgattgaa gaagtctgat gctcctgaaa aatcttaaaa tatctgactt 240
gtattgaaga aaattattta attaaatttt taaaggctgg ttgaaaaagt ctgacagttc 300
tgagaatttt ttaaatgtct gaattgtaat aaaaaaatgg tttactttaa acttctaaaa 360
actaatgacc ttgtgactaa 380

<210> SEQ ID NO 155
<211> LENGTH: 495
<212> TYPE: DNA
<213> ORGANISM: Homo sapiens

<400> SEQUENCE: 155
cttttgcgaa cctttcagtc tccgctagct ctttcctaat gagctttaca gcagaagctg 60
ttttatcgtt aagtgcccca cagagacact ttaccaggag gctgggagag ttctccagat 120
ttgggagagg cgcagagaca gtgtgtgagc cgagccctgt ctcagcaatc cacctggagg 180
agctagagta tcctcctccc tttaccattc agaccgagag aaaaagccca gcttgtgtgc 240
accctcgtgg ggttaaggcg agctgttcct ggtttaaagc ctttcagtat ttgttttgat 300
gtaaggctct gtggtttggg ggggaacatc tgtaaacatt attagttgat ttggggtttg 360
tctttgatgg tttctatctg caattatcgt catgtatatt taagtgtctg ttatagaaaa 420
cccacaccca ctgtcctgta aacttttctc agtgtccaga ctttctgtaa tcacatttta 480
attgccacct cgtat 495

<210> SEQ ID NO 156
<211> LENGTH: 540
<212> TYPE: DNA
<213> ORGANISM: Homo sapiens
<220> FEATURE:
<221> NAME/KEY: misc_feature
<222> LOCATION: (111)..(111)
<223> OTHER INFORMATION: n is a, c, g, t or u
<220> FEATURE:
<221> NAME/KEY: misc_feature
<222> LOCATION: (333)..(334)
<223> OTHER INFORMATION: n is a, c, g, t or u
<220> FEATURE:
<221> NAME/KEY: misc_feature
<222> LOCATION: (344)..(344)
<223> OTHER INFORMATION: n is a, c, g, t or u
<220> FEATURE:
<221> NAME/KEY: misc_feature
<222> LOCATION: (354)..(354)
<223> OTHER INFORMATION: n is a, c, g, t or u
<220> FEATURE:
<221> NAME/KEY: misc_feature
<222> LOCATION: (392)..(392)
<223> OTHER INFORMATION: n is a, c, g, t or u

<400> SEQUENCE: 156
aaatattcac aaacgtgcac acttctgcag agacaaagca tttcactgca cgtgtaccag 60
gttattgatt ttatcttttc ctttcagggt tttgtcctcc caaaccagag ncatatgctg 120
ctagtagaat tttttatttg atcctgcgaa cttttcttat aggaaaagta aggcaaagga 180
tgtgtagtgc aaccatctga taaactagtg tgattgtatt tatcctctgt tctgtgtatt 240
tctgtaatgg aatctttaca attcccaaaa cggtatttta gacctactgg aaatctgtat 300
cgaaacagct atgtgattct gccactgaga aannaaaatt tttnaattcg tttntcttat 360
gctggtttgt ttttctttaa tgaagaaatt gntctcatat ggcatcatag atgctaaata 420
aataaaagca tcatacttct ctagtttgcc tgcattcagt ggctaacatt atgagcattg 480
tgtaagataa acacatggtc agtatcaatg taaatgttag agccatgatt aattcctatg 540

<210> SEQ ID NO 157
<211> LENGTH: 460
<212> TYPE: DNA
<213> ORGANISM: Homo sapiens

<400> SEQUENCE: 157
gatcagttga aagcccttca gtgatagagg aagactggga gttttaaatg tttgaatact 60
ttttaatgaa ttcaatgaga cattttcttt gcttcttcaa agccagaaat aagatatagg 120
gggactatca aacatattat gatagaataa atatatttta tatggtcttg agaaatagta 180
agcttatttt atttatttat ttatttattt ttttacttct tgcatcgtat tctatgaact 240
cactttcaag agagagagac gttgtctatc cacaggtttt ctgcagtcct aattaaaaag 300
aactgcagtg agaagttttt catttcaact tccaacccaa gcttgagggc atagcagtaa 360
ctgcagagta tattgtgttc attttgctgt ttgagtagtt caggaaaaag gagttgcctt 420
tcaaacacca aacaactaat atgattccct gcggacactg 460

<210> SEQ ID NO 158

<211> LENGTH: 543
<212> TYPE: DNA
<213> ORGANISM: Homo sapiens

<400> SEQUENCE: 158
gttgattatt ctcctagctc atatctcctt gatgtgcatg agggagcact gggtctaatt 60
tttgggggct gagaaggtaa gaaggtgagg tcagtttttc ccaggagtcc taaaaaattc 120
tggtacctta cattgagggt gtgggagaaa gggtgtcata gttctgaaaa taggcagtag 180
catgaagcac cagacctgtc tcattcctta ttagatgtct atctcaaatg acagagtttg 240
aaaaatattg gttttatcat ttgatatttc catgcctgac tcgggaaaat aacattttct 300 gactttttc tattttcttg ccctgcacag accctacctg gtacaatttt ctatttctta 360
gctcaaagtg tctatacaat gggttgcctg gtatgtcagc tgccctcact cttgtgtaat 420
agaaatatat tgccaggctg gggacgtgga ggagacgaac tggattcctc cctcctcctg 480
ttgccaggcc tctctgcatt ggcactttat cctttcagtg tttctggctg tgttgggttc 540
att 543

<210> SEQ ID NO 159
<211> LENGTH: 431
<212> TYPE: DNA
<213> ORGANISM: Homo sapiens
<220> FEATURE:
<221> NAME/KEY: misc_feature
<222> LOCATION: (136)..(136)
<223> OTHER INFORMATION: n is a, c, g, t or u

<400> SEQUENCE: 159
ctctcggacc ttagggctgt tggagaaggc ttcagcagca gaactgatgg tgaaggctcg 60
tgttctccat cctcaacttt ctttgcttcg atcatacaca agaatacatt tggaagggca 120
aaaaatgaac actgtngttc attgcagccg tgttttgtga cacagatgca cagtctgctg 180
tgaagacctt ctctcaagtg gcatttggga gtccatgcca gatcatggtg cttcatgaga 240
gactgacagc tatcaggggt tgtggcactt agtgaggact ctcctccccc agtgtgtgct 300
gatgacacat acacacctga caatagcttg agtcttctct gttcctttta ctctgtagcc 360
aacatacaca tgatttaaaa ccctttctaa atatctatca tggttcatcc ttgtccaaat 420
gcagagtcag a 431

<210> SEQ ID NO 160
<211> LENGTH: 396
<212> TYPE: DNA
<213> ORGANISM: Homo sapiens

<400> SEQUENCE: 160
ggtgggacaa acctggactg ggtggagctg gggccccagc agtgggctct gccatagcag 60
gcgccataag ctggaatttg tgcctccagg cctggaggga cgcaaggcgt ttctgatgaa 120
gccgatacat tcagaattgg ggtccaaata ggaaataatg cccttttcag gctagtgaaa 180
atgttgaact ctaagagata agtttattta gagactggat tgagcttttg tttaagattt 240
cccacctgcg taaaattcct ttcagcccat aggattcttg attctgaagt ccagacagaa 300
gcctgtgttc tgtagctgct gaacaaagat gagagatcac tggggctgct gtttgtccga 360
agtttgtgtg ggtatcatga tgaaccctct tctaag 396

<210> SEQ ID NO 161
<211> LENGTH: 393

<212> TYPE: DNA
<213> ORGANISM: Homo sapiens

<400> SEQUENCE: 161
tggaacacca caggtttagt tgggaaaata ttttgcagct gagttagaaa cttgaaagtt 60
aggcttataa tcaagatgct gattttcaac cttagcatcg gggaaggtaa tgatagttta 120
gttggcaaag actttttgca gcaaactgta tttgagacag cagaatccaa ggatatcttt 180
caagattcac ttatactaca ttctttttag ccccctctct aggggtggag ggggtggctt 240
agaaaaacca aaggtaatct ggtttcaatt acatgctgta aaaatagaat ttgtggccag 300
aaattaattt ggaatatttt ttatgggggc aacattgtgg gttgtatgag tctttcacca 360
actttattgc ttttctttgg ttctggatct aaa 393

<210> SEQ ID NO 162
<211> LENGTH: 519
<212> TYPE: DNA
<213> ORGANISM: Homo sapiens
<220> FEATURE:
<221> NAME/KEY: misc_feature
<222> LOCATION: (297)..(297)
<223> OTHER INFORMATION: n is a, c, g, t or u

<400> SEQUENCE: 162
ggaggtttaa tacggccaat ggatcttgta taaagtctac gtaagtttta atttaccaga 60
gctataagat ggttaaggta gactagtggg gactgctaca gataaaatga gatacaaaga 120
acatttgcaa ataaatgcca taaaattaca gtagcttgga attttagtga atcatggccc 180
ttgtgttatc tagaatgcta attattcaag ctgttcctaa acttaagtat gacatataag 240
attaaaatct tggggggaaa aactgttcag atgaaaagtc aagtcaagaa gtttccncaa 300
aagaaaagaa aaatcctaaa aaccatctag ctgttgttac attaaattta tttctcacct 360
ccattaaaag ggtttttgct ttggagtttt gttaactttc gttctttgga gtaataatat 420
ttctcttgtg tatggcgctg aatacatttg tcaataatac gtcaaaaaaa aaaacacttg 480
gcttcttaat acttggaaat acgtacatat tccttacta 519

<210> SEQ ID NO 163
<211> LENGTH: 503
<212> TYPE: DNA
<213> ORGANISM: Homo sapiens

<400> SEQUENCE: 163
gaggatgtac ttgcatactg ttgaagttga gtgctgtttt gctgttaatg ctgctgcttt 60
gccaatgaag aatgaaataa atttatctga atgtatcaat aactttaaaa tggaatgctg 120
cacttttaaa atatggtaga ttattgacat ttgcaagaag aatgtattga ggtctttgga 180
aatgcccaaa ttctttgcca cctataatta aaaattgtct gaattttctc ctcagtataa 240
aggagtgaat gccctactta gtgtaattgt atcaagtgaa gtcaaacatc aacaaaagaa 300
cagtaaagtc tcattgcaaa gcagatactg ggcctcaagg gtgggcttag gcttaaacta 360
gattatctgc tttcatatac taatgttttc atttcaaaat catgtgtccc caaaatattg 420
caacttactg aatattttag atctcttggg ttacttaaat atgtgtgaaa aaatcaacat 480
tgcattgcaa atcccagtgt tta 503

<210> SEQ ID NO 164
<211> LENGTH: 519
<212> TYPE: DNA

<213> ORGANISM: Homo sapiens
<220> FEATURE:
<221> NAME/KEY: misc_feature
<222> LOCATION: (100)..(100)
<223> OTHER INFORMATION: n is a, c, g, t or u
<220> FEATURE:
<221> NAME/KEY: misc_feature
<222> LOCATION: (219)..(219)
<223> OTHER INFORMATION: n is a, c, g, t or u

<400> SEQUENCE: 164
gacactcact ctttgattcg gatgtggaca tggatgacta tacagaccac gaacagtgca 60
agtgacgtcc agcctcactg accctcttcc ttgggacctn ccactccctg ggtcggtcca 120
ttttcccagg tagcaatcca tccgagctgg gaggagatct tcgtgcttgg cagagttttc 180
acatgctaac tggactatag cagccttatt tcttttttng tacaaacaaa acacagaacc 240
attcagatga ctccattgaa aacaaacagg caaaaaataa tgtcagcatg gttcctgaaa 300
tccatttttg ttttcattag aaaactatta ataatattgt gtggtagagc aggtgtaaga 360
gctggttgtc agctgatagt ttttatgatg atcctcttca accctgaggt cttaattgtg 420
agatggattc ttgaacctcc ttcctccacc aggatttgaa gtaatgagag atatcatcag 480
aaaaatgttt tacggtggct gcttgtactt tatgtgtgt 519

<210> SEQ ID NO 165
<211> LENGTH: 470
<212> TYPE: DNA
<213> ORGANISM: Homo sapiens

<400> SEQUENCE: 165
acttgaatga ttatgtgacc ctgttatatt tcagtgttgt gacaaatgtg taaactagcg 60
ggggaagaca gtattgtatc ataaatgaga tgcgtagttt gttttctttc atgggaagta 120
gagataaaaa tatatacatt tctctaattg agttgtttag agaaagaact aatgtctcat 180
atgatgtatt tacttatttt aaaaaaaaga ataggaatga gatgtccctg agctgtactt 240
ttctattatt ataaggcctt taggcatcag tgcatctggg ttatcaacat tttctcaaat 300
gctgtcaata ttttactgta atttatgttc ttatatttat gtatatttgt taaaactgta 360
aaaaaatttc acagattttt ttccaatacc tgtgcaagat acatgtgtag ctcaaaacta 420
tttgtgatct actgtttgca tgtaagagac caggatatgt aactcttata 470

<210> SEQ ID NO 166
<211> LENGTH: 458
<212> TYPE: DNA
<213> ORGANISM: Homo sapiens

<400> SEQUENCE: 166
gaacatgcca gggcccagat gagggcccag atgaatatcg gggatgaagc gctgattgga 60
cggtggagct gggatgacat acaagtcgag ctcctgacct gggatgagga cggagatttt 120
ggcgatgcct gggccaggat ccccctttgct ttctgggcca gataccatca gtacattctg 180
aatagcaacc gtgccaacag gagggccacg tggagagctg gcgtcagcag tggcaccaat 240
ggaggggcca gcaccagcgt cctagatggc cccagcacca gctccaccat ccggaccaga 300
aatgctgcca gagctggcgc cagcttcttc tcctggatcc agcaccgttg acgaactgca 360
gcgatcttac tggccaagcc agagcgcctc ctctcagatt ccttctcgac acagcaccct 420
aggcggcttc ttcctgtcag tcggaggtgg catgcaag 458

<210> SEQ ID NO 167
<211> LENGTH: 131
<212> TYPE: DNA
<213> ORGANISM: Homo sapiens

<400> SEQUENCE: 167
gaattgacag tgattccgtt ttcaaagcat ttattgaata gtatcttcca aacagtatgc 60
tggcttttag acaggttata caggtgaatg taggggtcta tccttaaaaa gcctataagg 120
cagttgttct c 131

<210> SEQ ID NO 168
<211> LENGTH: 338
<212> TYPE: DNA
<213> ORGANISM: Homo sapiens

<400> SEQUENCE: 168
gtccctggtg ccaaatctgt gggagatcac tggcttagaa tcttcaaaag agtattgccc 60
ccaatgtaaa ctatggactt tgtgtgataa tgacatgtca atgtaagttc atcaactgta 120
acaaatgtgc cattctggag agagatgttg atagtctagg aggctatgca tgtgtggagg 180
cagggggtat atgggaactt tctgtacttc ctgctcaatt ttgctgtgaa tctgaaacta 240
ctctaaaaaa taaggtctat tttcttaaag gtcattttgc ctccatagtg ggaaagaaaa 300
tagcagttga ctaatagctg ctcttatcct gcctaaaa 338

<210> SEQ ID NO 169
<211> LENGTH: 459
<212> TYPE: DNA
<213> ORGANISM: Homo sapiens

<400> SEQUENCE: 169
gaagtgaacc ttctagatcc tgctgactca tacaatgagt tttgtgtgga ccatcagaca 60
aaagggctgg ctggtgaagg tggctgttgt ctggaaattc ctcccagctc tcctctaatt 120
atgtcataag gactggaggc cccttagcct gcttgtgata acacgcaagg aaatatgggc 180
caactcttca catgaacaca agatatttcc atgctagcct tttgcaagta acaacagaga 240
gagctctgtg cagttttcac tggaatgcct gtggattgct tgtgtcataa ctgtaatcta 300
aagagttgtc catttgttga ttcctttgta tttgtattgg tagaattgcc actatcaaac 360
caagatcttt agctgccttt gtatcaactt ctttggagct tatgtgattt tccagaaaat 420
ttccaaggca tagttttgtc cctaagtccc atgaatatg 459

<210> SEQ ID NO 170
<211> LENGTH: 484
<212> TYPE: DNA
<213> ORGANISM: Homo sapiens
<220> FEATURE:
<221> NAME/KEY: misc_feature
<222> LOCATION: (42)..(42)
<223> OTHER INFORMATION: n is a, c, g, t or u
<220> FEATURE:
<221> NAME/KEY: misc_feature
<222> LOCATION: (81)..(81)
<223> OTHER INFORMATION: n is a, c, g, t or u
<220> FEATURE:
<221> NAME/KEY: misc_feature
<222> LOCATION: (144)..(144)
<223> OTHER INFORMATION: n is a, c, g, t or u
<220> FEATURE:
<221> NAME/KEY: misc_feature
<222> LOCATION: (260)..(260)
<223> OTHER INFORMATION: n is a, c, g, t or u
<220> FEATURE:

<221> NAME/KEY: misc_feature
<222> LOCATION: (263)..(263)
<223> OTHER INFORMATION: n is a, c, g, t or u

<400> SEQUENCE: 170
ctcctgtatc ttattcccta gggccacttg cacctttcaa antggataaa ttaaattccc 60
ctgctcccct tctaccaact ntaacatcat atccttggtg tatgatgccc tacttttcat 120
tgttttgcct aaataagagt atgnttggga attttaggct tagggctggg aaaagatggg 180
atatggaatc gtcagctata gattgccgga caagaaattt taggagcagt agacctttca 240
accgccctca ataggatggn acntgactgt ccccacaacc tatttccctt tcagtggctt 300
gctccagcca aggcccctta tttaagagat ctttgtgcgc tctgaaaacc atgcatatgc 360
cagaactagg tgctctgttt catgaaggca gtttgataac tgaatggact ttggaagtgc 420
ccagtgtttg actattaccc tggtgcgatg atcacactgg gcgtatcatt gtcacatgat 480
ccca 484

<210> SEQ ID NO 171
<211> LENGTH: 536
<212> TYPE: DNA
<213> ORGANISM: Homo sapiens
<220> FEATURE:
<221> NAME/KEY: misc_feature
<222> LOCATION: (60)..(61)
<223> OTHER INFORMATION: n is a, c, g, t or u

<400> SEQUENCE: 171
acatgccctt agaatgtgca ttttttaacc tattaaattt gccaatcttg caaactattn 60
nttacttgta ttgcataatt agatactcat attaacatat tgaattcaga aaaagttagc 120
aagccaagat gacattctct gtagcactat tttaaattat aatgaatgat cacataaaac 180
tctttagtat ttatctaaag taattattac tctacttcat ttgtttatct aaatcagtga 240
tcattgatgt ttgaactttt tggcttaaat gtttattttg tttatactac ttgctagagt 300
aaaataaatt taatacatga aaaactctac acaatttaaa ataggttata atttgtcaat 360
acttatgttt taaaatattt ttagaaggag gagtgctgta tattattaaa acaattttct 420
gaaattgttt aatattatct ttgattttaa aatgacatat atgtggattt acaatgaatc 480
aaattgtcct aaaagatgtc agataagaaa tgcaagtgct ttgcaagtct aatact 536

<210> SEQ ID NO 172
<211> LENGTH: 311
<212> TYPE: DNA
<213> ORGANISM: Homo sapiens

<400> SEQUENCE: 172
aaacacagtc catgctattc taccactggc tgtgtcttag aaggcctcag aggccactcc 60
aaaaacaatg ctctgtgctt ttataatatt ttaatgtccc tggttatatc agtaagcata 120
cattagaaag tattagctta aaacattcta caccaaaatg aagtacattc acatattttg 180
tgctgcatct tacaggtctt ctagtacctt ctatcccctt ctatgattgg tcgtacacat 240
agtacgtaag agcctcttcc catatagaag aaggggaaa gctaagctgc tttcagctat 300
caacccagga c 311

<210> SEQ ID NO 173
<211> LENGTH: 370
<212> TYPE: DNA
<213> ORGANISM: Homo sapiens
<220> FEATURE:
<221> NAME/KEY: misc_feature
<222> LOCATION: (92)..(92)
<223> OTHER INFORMATION: n is a, c, g, t or u

<400> SEQUENCE: 173
aaccatgcct ctttataaca tttagatcac cgtccttata atgcgccttt ctgtctcttt 60
ttaaaccttg agcaccttga aggcaaaaat tncaactttc tttccctagt gtcttgcact 120
ccctggtatc tagcacatag agagctcaat aaatgttttt tgaatgagta aatcattgca 180
cgaatttata acttcatgaa cccatggaac ccattgactg gtctgccctc atctccgatc 240
cttggctgaa aagcctaaca agccattatc tgtccgtact gaaacactcc tcctgatgtc 300
aagaaccttc taaacataaa accacctggt gcacggatca tttcttcttc caagatgtat 360
ctgccattga 370

<210> SEQ ID NO 174
<211> LENGTH: 463
<212> TYPE: DNA
<213> ORGANISM: Homo sapiens
<220> FEATURE:
<221> NAME/KEY: misc_feature
<222> LOCATION: (384)..(388)
<223> OTHER INFORMATION: n is a, c, g, t or u
<220> FEATURE:
<221> NAME/KEY: misc_feature
<222> LOCATION: (390)..(390)
<223> OTHER INFORMATION: n is a, c, g, t or u

<400> SEQUENCE: 174
aattaacctt agcattattc ctgtgcttta ttattcactg ataggttctt attcaactaa 60
tgtttatttc ttgcctaata tgtgccagaa accgtgaagt gtttaggata tgcagtgagt 120
ggttaatgag acaagtatga tccaacttgt gtttgcaatt aagcagggat acaggtactg 180
aataaatact gaaaataatt aaaatggtaa taagtgattt gttaatactg atgcatgtag 240
atctaattca ttttaaatgt tacaaaataa gttacaaaat ggtatatgcc atatgatgct 300
atttttgtac atctataata aactttatga gacacaaata tgcaatgtag ttactaataa 360
aactataaga acaagaacac caannnnnan ataaagctta ctgccaggag ggaatggaat 420
ggatgcagag agcatggtta gctgtatctt taatgtttca ttt 463

<210> SEQ ID NO 175
<211> LENGTH: 263
<212> TYPE: DNA
<213> ORGANISM: Homo sapiens
<220> FEATURE:
<221> NAME/KEY: misc_feature
<222> LOCATION: (28)..(28)
<223> OTHER INFORMATION: n is a, c, g, t or u
<220> FEATURE:
<221> NAME/KEY: misc_feature
<222> LOCATION: (30)..(30)
<223> OTHER INFORMATION: n is a, c, g, t or u
<220> FEATURE:
<221> NAME/KEY: misc_feature
<222> LOCATION: (50)..(50)
<223> OTHER INFORMATION: n is a, c, g, t or u
<220> FEATURE:
<221> NAME/KEY: misc_feature
<222> LOCATION: (54)..(54)
<223> OTHER INFORMATION: n is a, c, g, t or u
<220> FEATURE:
<221> NAME/KEY: misc_feature
<222> LOCATION: (77)..(77)
<223> OTHER INFORMATION: n is a, c, g, t or u

<400> SEQUENCE: 175
catgtaagaa ttcccgggag ctccatgncn ttttaatttt agccattctn ctgncctcat 60
ttcttaaaat tagagantta aggtcccgaa ggtggaacat gcttcatggt cacacataca 120
ggcacaaaaa cagcattatg tggacgcctc atgtattttt tatagagtca actatttcct 180
ctttattttc cctcattgaa agatgcaaaa cagctctcta ttgtgtacag aaagggtaaa 240
taatgcaaaa tacctggtag taa 263

<210> SEQ ID NO 176
<211> LENGTH: 421
<212> TYPE: DNA
<213> ORGANISM: Homo sapiens

<400> SEQUENCE: 176
gcttcagagg taacacttgg ccaagatatg agatctgaat tacctttccc tctttccaag 60
aaggaaggtt tgactgagta ccaatttgct tcttgtttac ttttttaagg gctttaagtt 120
atttatgtat ttaatatgcc ctgagataac tttggggtat aagattccat tttaatgaat 180
tacctacttt attttgtttg tctttttaaa gaagataaga ttctgggctt gggaatttta 240
ttatttaaaa ggtaaaacct gtatttattt gagctattta aggatctatt tatgtttaag 300
tatttagaaa aaggtgaaaa agcactatta tcagttctgc ctaggtaaat gtaagataga 360
attaaatggc agtgcaaaat ttctgagtct ttacaacata cggatatagt atttcctcct 420
c 421

<210> SEQ ID NO 177
<211> LENGTH: 170
<212> TYPE: DNA
<213> ORGANISM: Homo sapiens

<400> SEQUENCE: 177
cccctcggaa gttgtacagg cccagtgtag gaacttgggc tgcatcaatg ctcaaggaaa 60
ggaagacatc tccatgaatt ccgttcccat ccagcaagag accctggtcg tccggaggaa 120
gcaccaaggc tgctctgttt ctttccagtt ggagaaggtg ctggtgactg 170

<210> SEQ ID NO 178
<211> LENGTH: 439
<212> TYPE: DNA
<213> ORGANISM: Homo sapiens

<400> SEQUENCE: 178
gggaagccaa actccatcat gatgggtgga ttccaaatga acccctgcgt tagttacaaa 60
ggaaaccaat gccacttttg tttataagac cagaaggtag actttctaag catagatatt 120
tattgataac atttcattgt aactggtgtt ctatacacag aaaacaattt attttttaaa 180
taattgtctt tttccataaa aaagattact ttccattcct ttaggggaaa aaacccctaa 240
atagcttcat gtttccataa tcagtacttt atatttataa atgtatttat tattattata 300
agactgcatt ttatttatat cattttatta atatggattt atttatagaa acatcattcg 360
atattgctac ttgagtgtaa ggctaatatt gatatttatg acaataatta tagagctata 420
acatgtttat ttgacctca 439

<210> SEQ ID NO 179
<211> LENGTH: 529
<212> TYPE: DNA
<213> ORGANISM: Homo sapiens

<400> SEQUENCE: 179
ggaatctaca aagccatcag tgaactggat attcttcttt cctggattaa aaaattattg 60
gaaagcagtc agtaaaccaa agccaagtac attgatttta cagttatttt gaaatacaat 120
aagaactgct agaaatatgt ttataacagt ctatttcttt taaaaacttt ttaacataat 180
actgacggca tgttaggtga ttcagaatag acaagaagga tttagtaaat taacgttttg 240
gatataagtt gtcactaatt tgcacatttt ctgtgttttc aaataatgtt tccattctga 300
acatgttttg tcattcacaa gtacattgtg tcaacttaat ttaaagtatg taacctgaat 360
taactcgtgt aatatttgtg tgtggagtgg gatgtggggg gtggaggggg aatgacagat 420
ttctggaatg caatgtaatg ttactgagac ttaaatagat gttatgtata tgattgtctg 480
tttaagtgtt tgaaaattgt taattatgcc cagtgtgaac ttagtactt 529

<210> SEQ ID NO 180
<211> LENGTH: 335
<212> TYPE: DNA
<213> ORGANISM: Homo sapiens
<220> FEATURE:
<221> NAME/KEY: misc_feature
<222> LOCATION: (216)..(216)
<223> OTHER INFORMATION: n is a, c, g, t or u

<400> SEQUENCE: 180
ggcaagatca gatcctggag gactttcctg gcctgcccgc cagccctgct cttgttgtgg 60
agaaggaagc agatgtgatc acatcacccc gtcattgggc accgctgact ccagcatgga 120
ggacaccagg gagcagggcc tgggcctgtt tccccagctg tgatcttgcc cagaacctct 180
cttggcttca taaacagctg tgaaccctcc cctganggat taacagcaat gatgggcagt 240
cgtggagttg ggggggttgg gggtgggatt gtgtcctcta aggggacggg ttcatctgag 300
taaacataaa ccccaacttg tgccattctt tataa 335

<210> SEQ ID NO 181
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 181
tctccctcgc tcgaaattac a 21

<210> SEQ ID NO 182
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 182
cagaatatcc ccgtacatgt ccat 24

<210> SEQ ID NO 183
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 183
tccttgaaca tctttggctc ttc 23

<210> SEQ ID NO 184
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 184
tccatgtgcc gtttctgaac 20

<210> SEQ ID NO 185
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 185
agaggagcag tatcaggact ttgaa 25

<210> SEQ ID NO 186
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 186
agcggtcgtg cacactca 18

<210> SEQ ID NO 187
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 187
cggcttgcac cagtttcttc 20

<210> SEQ ID NO 188
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 188
gctccttctt ctatcggttt catc 24

<210> SEQ ID NO 189
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 189
tcggagggca gagctctaac 20

<210> SEQ ID NO 190
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 190
cctcgatgtt catcccgatt 20

<210> SEQ ID NO 191
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 191
gatcagcccc actctccaaa 20

<210> SEQ ID NO 192
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 192
gatggatccc cactgatgat g 21

<210> SEQ ID NO 193
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 193
catgatgcta agagtcctgg gtaa 24

<210> SEQ ID NO 194
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 194
ttctgcaact gagaagcaca tatg 24

<210> SEQ ID NO 195
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 195
caaggagggc cagtgcaa 18

<210> SEQ ID NO 196
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 196
gaagccccac ccttctcttc 20

<210> SEQ ID NO 197
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 197
gggcatccct gtgaacagta a 21

<210> SEQ ID NO 198
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 198
ggtacccgtt cctccctaca c 21

<210> SEQ ID NO 199
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 199
tgcatgttaa tggtgagtga atcc 24

<210> SEQ ID NO 200
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 200
ttgatccaac aaatgcccta atac 24

<210> SEQ ID NO 201
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 201
ggtcaaactc ctcatcgaca tg 22

<210> SEQ ID NO 202
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 202
ccccttcact caaacatctc gta 23

<210> SEQ ID NO 203
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 203
ccagtggaaa aacaatggag tca 23

<210> SEQ ID NO 204
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 204
acagcaattg tcctggagca t 21

<210> SEQ ID NO 205
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 205
ctgctcatcg ctgtcatcgt 20

<210> SEQ ID NO 206
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 206
cgggacacag ccatgca 17

<210> SEQ ID NO 207
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 207
agagtttgag aagcaaggga tttact 26

<210> SEQ ID NO 208
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 208
ggccggtgca gtcactctt 19

<210> SEQ ID NO 209
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 209
gcccacagac ttagccatca 20

<210> SEQ ID NO 210

<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 210
tcccggcgac aatgc 15

<210> SEQ ID NO 211
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 211
tgccaccacc tattactggt aca 23

<210> SEQ ID NO 212
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 212
agtttaagcc cccactttca gaa 23

<210> SEQ ID NO 213
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 213
tccatagctg ggtctggtgt aga 23

<210> SEQ ID NO 214
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 214
ttcttgattg agacccagga ttc 23

<210> SEQ ID NO 215
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 215
gagaggctcc agcactacat ca 22

<210> SEQ ID NO 216
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 216
ctacaccaac ccattccagg at 22

<210> SEQ ID NO 217
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 217
ttcagttcct ggattctcct gagt 24

<210> SEQ ID NO 218
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 218
cagtgagggt tacctgaaaa atgc 24

<210> SEQ ID NO 219
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 219
tcagggacca accaccaaga 20

<210> SEQ ID NO 220
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 220
caggacaggt gtgtaggcag ttt 23

<210> SEQ ID NO 221
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 221
ccaccacatt ccctgtaacc a 21

<210> SEQ ID NO 222
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 222
tccgtctaca cttttgttga caca 24

<210> SEQ ID NO 223
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 223

ctcagtctct tctccagtgt gttca                                           25

<210> SEQ ID NO 224
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 224

ggagcttctc ctggcatgtg                                                 20

<210> SEQ ID NO 225
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 225

gggcggcaaa aaactgaga                                                  19

<210> SEQ ID NO 226
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 226

ccgcgatgca gctgttct                                                   18

<210> SEQ ID NO 227
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 227

caattgtatg tgactgccca aga                                             23

<210> SEQ ID NO 228
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 228

tgggtatctc aggcatctcc tt                                              22

<210> SEQ ID NO 229
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 229

tgctccccac ccccttta                                                   18
```

<210> SEQ ID NO 230
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 230
ctgctttgtt tgctctgcaa gt 22

<210> SEQ ID NO 231
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 231
cctgagccac tgccaacatt 20

<210> SEQ ID NO 232
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 232
aggtgtcaga ttttccctca gaat 24

<210> SEQ ID NO 233
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 233
catgcctcac atcgcttcag 20

<210> SEQ ID NO 234
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 234
ccacactatc ttcatcccaa tgac 24

<210> SEQ ID NO 235
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 235
cttgccctca ctgcaacaga 20

<210> SEQ ID NO 236
<211> LENGTH: 20
<212> TYPE: DNA
<213> ORGANISM: Artificial Sequence
<220> FEATURE:

<223> OTHER INFORMATION: synthetic oligonucleotide

<400> SEQUENCE: 236
tctgcagatg agccctcaga 20

<210> SEQ ID NO 237
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 237
gatgcgccag gaagtttca 19

<210> SEQ ID NO 238
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 238 gacgcccccct tgttgtttg 19

<210> SEQ ID NO 239
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 239
gcgggctcta tcacaaaatg a 21

<210> SEQ ID NO 240
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 240
gccttcgctt gggcttaat 19

<210> SEQ ID NO 241
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 241
cacctggctg ggaaaatgg 19

<210> SEQ ID NO 242
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 242
ggagcccttg tcggatgat 19

<210> SEQ ID NO 243
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 243
ggcagttctc caggctattt gt 22

<210> SEQ ID NO 244
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 244
ggaggccaaa gacacagatc a 21

<210> SEQ ID NO 245
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 245
ccaaggctca gtcatgagaa ca 22

<210> SEQ ID NO 246
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 246
gcggaagaag cccttgca 18

<210> SEQ ID NO 247
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 247
ccaacgcaaa gcaatacatg a 21

<210> SEQ ID NO 248
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 248
cgaaacagca tctgactcct ttt 23

<210> SEQ ID NO 249
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 249
tgggtctcac ctcccaactg 20

<210> SEQ ID NO 250
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 250
gccggcacat gctagca 17

<210> SEQ ID NO 251
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 251
cccaaaaggt cctcagatta ctaca 25

<210> SEQ ID NO 252
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 252
cattgcggtg gagattcca 19

<210> SEQ ID NO 253
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 253
acccactcct ccacctttga 20

<210> SEQ ID NO 254
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 254
ttgctgtagc caaattcgtt gt 22

<210> SEQ ID NO 255
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 255
cagcagatgt ggatcagcaa g 21

<210> SEQ ID NO 256
<211> LENGTH: 18

-continued

```
<212> TYPE: DNA
<213> ORGANISM: Artificial Sequence
<220> FEATURE:
<223> OTHER INFORMATION: synthetic oligonucleotide

<400> SEQUENCE: 256

gcatttgcgg tggacgat                                                18


<210> SEQ ID NO 257
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 257

tgctgtctcc atgtttgatg tatct                                        25


<210> SEQ ID NO 258
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 258

tctctgctcc ccacctctaa gt                                           22


<210> SEQ ID NO 259
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 259

gtcgcagccg ggatttg                                                 17


<210> SEQ ID NO 260
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 260

gcattgtcaa gtgacgatca ca                                           22
```